United States Patent [19]

Ueno et al.

[11] Patent Number: 5,377,682
[45] Date of Patent: Jan. 3, 1995

[54] ULTRASONIC PROBE FOR TRANSMISSION AND RECEPTION OF ULTRASONIC WAVE AND ULTRASONIC DIAGNOSTIC APPARATUS INCLUDING ULTRASONIC PROBE

[75] Inventors: Shinichiro Ueno, Sagamihara; Masahiko Hashimoto, Tokyo; Akihisa Adachi, Kawasaki; Haruo Ohmori, Yokohama; Toshiharu Sato, Kawasaki, all of Japan

[73] Assignee: Matsushita Electric Industrial Co., Ltd., Osaka, Japan

[21] Appl. No.: 941,580

[22] Filed: Sep. 4, 1992

[30] Foreign Application Priority Data

| | | |
|---|---|---|
| Sep. 5, 1991 | [JP] Japan | 3-225907 |
| Sep. 18, 1991 | [JP] Japan | 3-237709 |
| Oct. 15, 1991 | [JP] Japan | 3-265886 |
| Oct. 24, 1991 | [JP] Japan | 3-277430 |
| Dec. 27, 1991 | [JP] Japan | 3-346034 |
| Dec. 27, 1991 | [JP] Japan | 3-346035 |
| Feb. 17, 1992 | [JP] Japan | 4-028767 |
| Mar. 13, 1992 | [JP] Japan | 4-055150 |
| Mar. 19, 1992 | [JP] Japan | 4-062990 |

[51] Int. Cl.[6] ............................ A61B 8/12
[52] U.S. Cl. ........................ 128/660.1; 128/662.06
[58] Field of Search .......... 128/660.03, 660.09, 128/660.10, 662.03, 662.06

[56] References Cited

U.S. PATENT DOCUMENTS

| | | | |
|---|---|---|---|
| 5,000,185 | 3/1991 | Yock | 128/662.06 |
| 5,090,414 | 2/1992 | Tokono | 128/662.06 |
| 5,115,814 | 5/1992 | Griffith et al. | 128/660.03 |
| 5,203,338 | 4/1993 | Jong | 128/662.06 |
| 5,243,988 | 9/1993 | Sieben et al. | 128/661.04 X |

*Primary Examiner*—Francis Jaworski
*Attorney, Agent, or Firm*—Lowe, Price, LeBlanc & Becker

[57] ABSTRACT

An ultrasonic probe to be used for an ultrasonic diagnostic apparatus for obtaining an ultrasonic image. The ultrasonic probe comprises a catheter having a hollow tubing structure, a joint having a tubing structure and arranged to be at its one end portion connected to a tip portion of said catheter, a bearing connected to the other end portion of the joint, a rotating shaft inserted into the bearing to be rotatable and arranged so that a portion of the rotating shaft contacts with one end portion of the bearing, and a rotator connected to the rotating shaft and arranged so that one end portion of the rotator contacts with the other end portion of the bearing so that the bearing is interposed and supported between the portion of the rotating shaft and the rotator. An ultrasonic transducer is inserted into the rotator for transmitting and receiving an ultrasonic wave, a torque transmission shaft having a hollow structure is at its one end portion connected to the rotating shaft, and a guide wire is inserted into the hollow of the torque transmission shaft. A rotating force generated by a drive section is applied through the torque transmission shaft to the ultrasonic transducer whereby the ultrasonic transducer rotationally driven to perform a radial scanning operation. This arrangement allows a free movement of the guidewire within the catheter so that the catheter can easily be lead along the guidewire up to a target portion within a blood vessel.

18 Claims, 51 Drawing Sheets

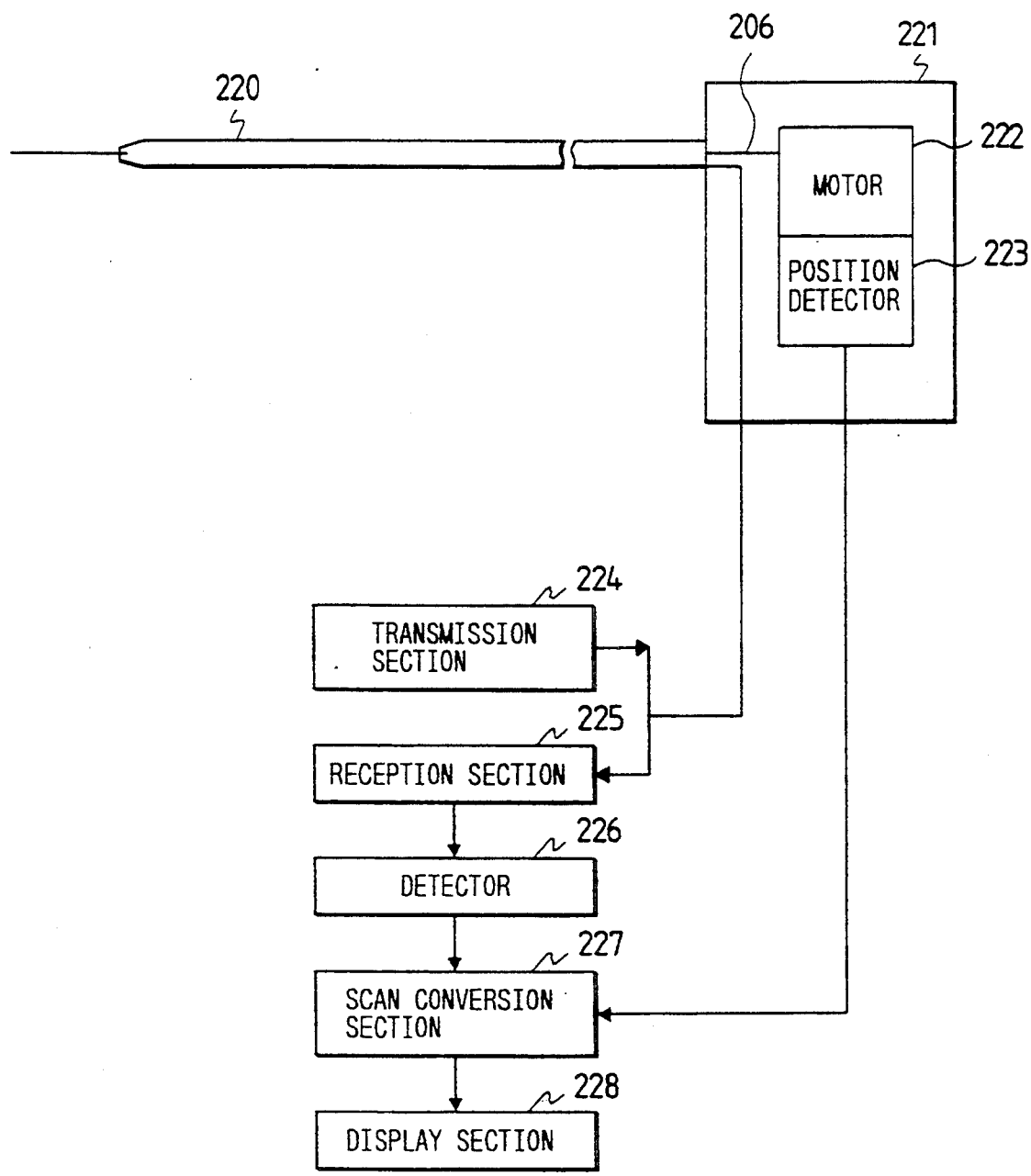

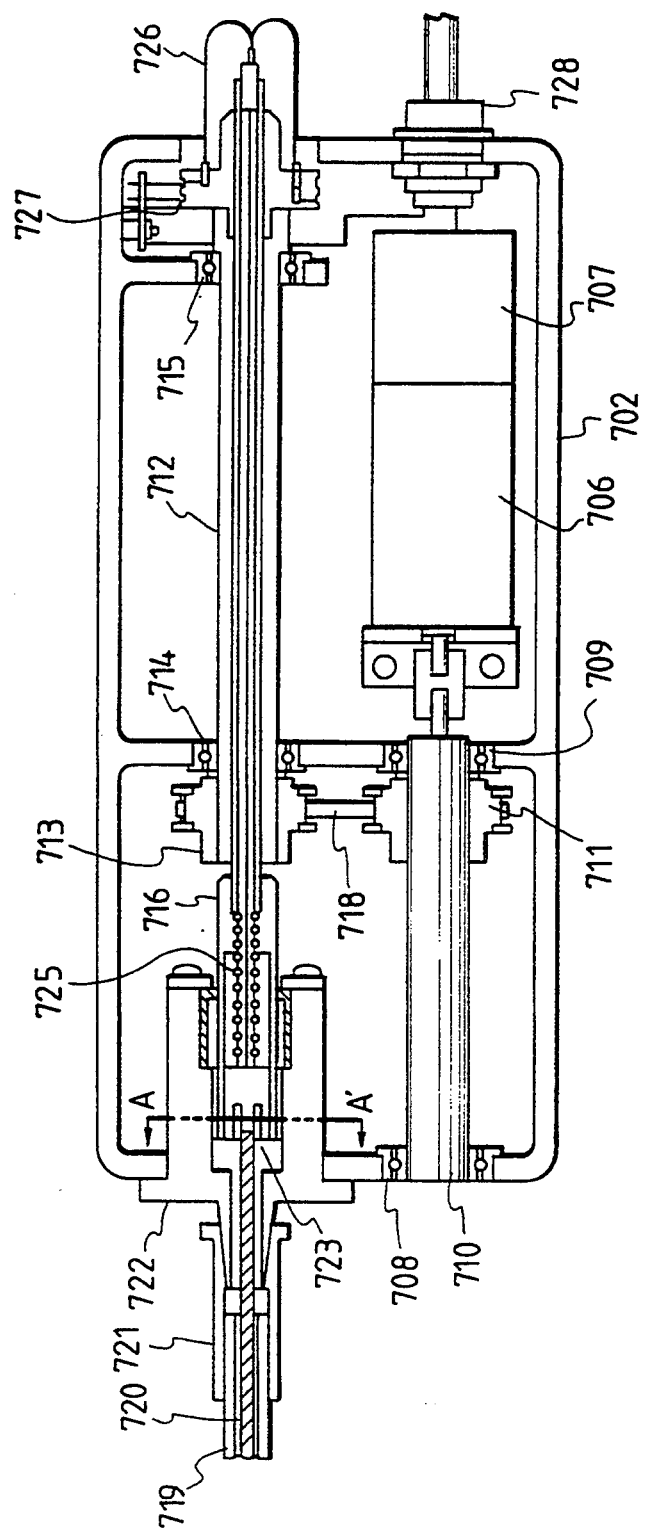
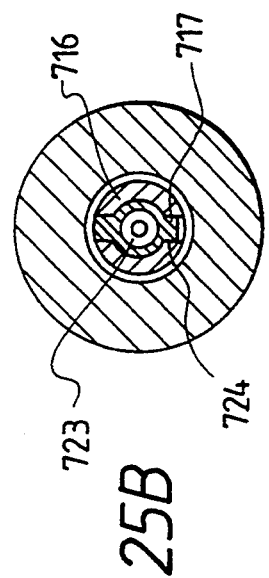
FIG. 25A
FIG. 25B

FIG. 30A
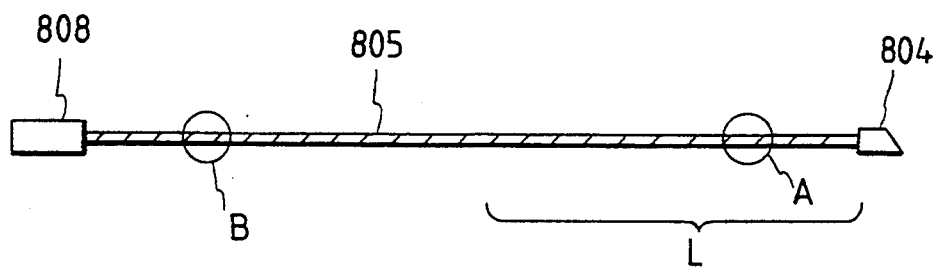
FIG. 30B
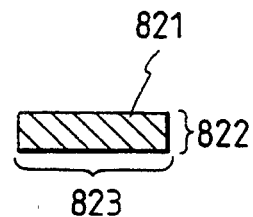
FIG. 30C
FIG. 30D
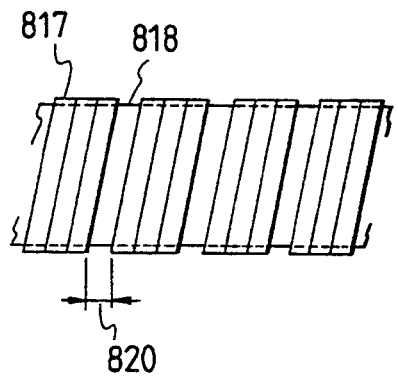
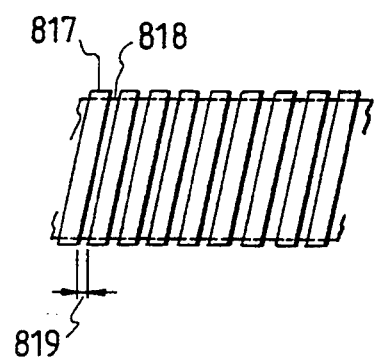

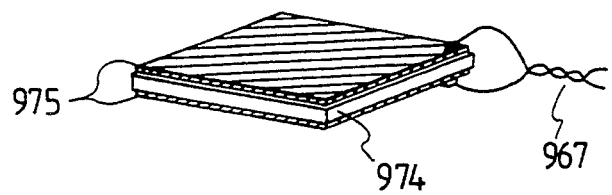
FIG. 47
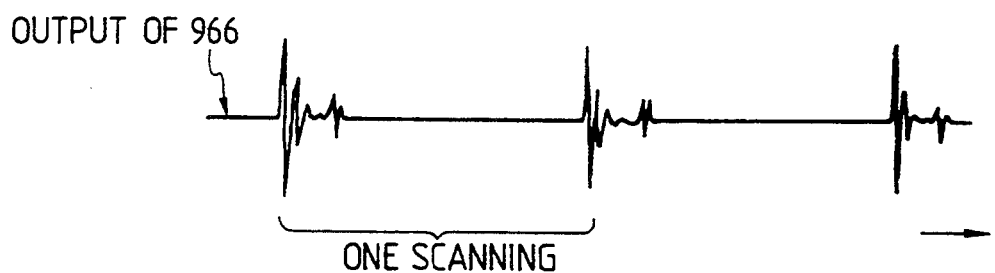
FIG. 48A
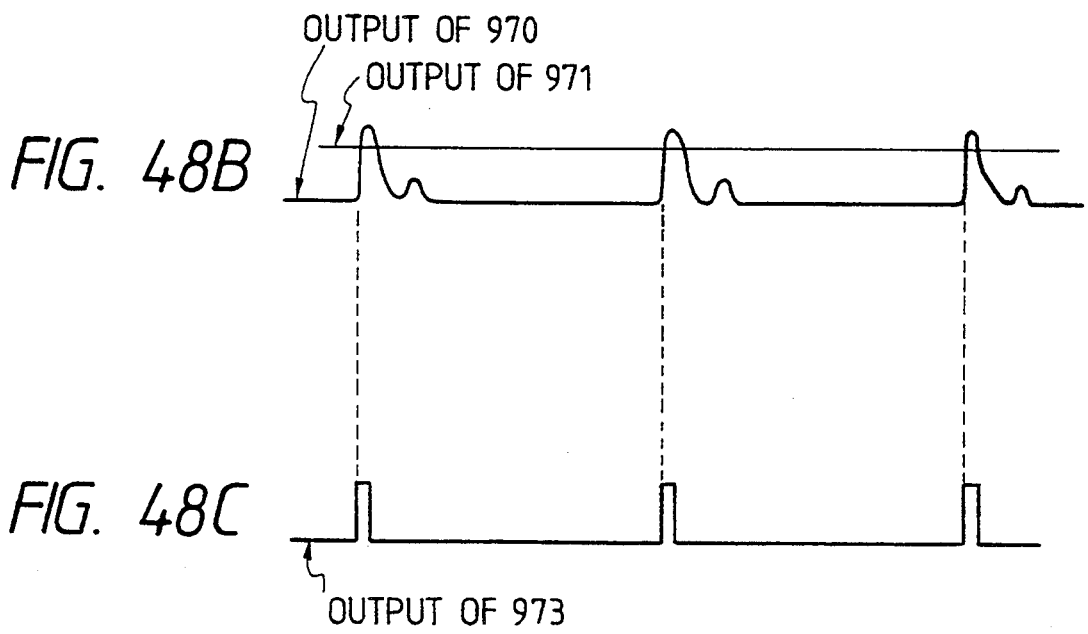

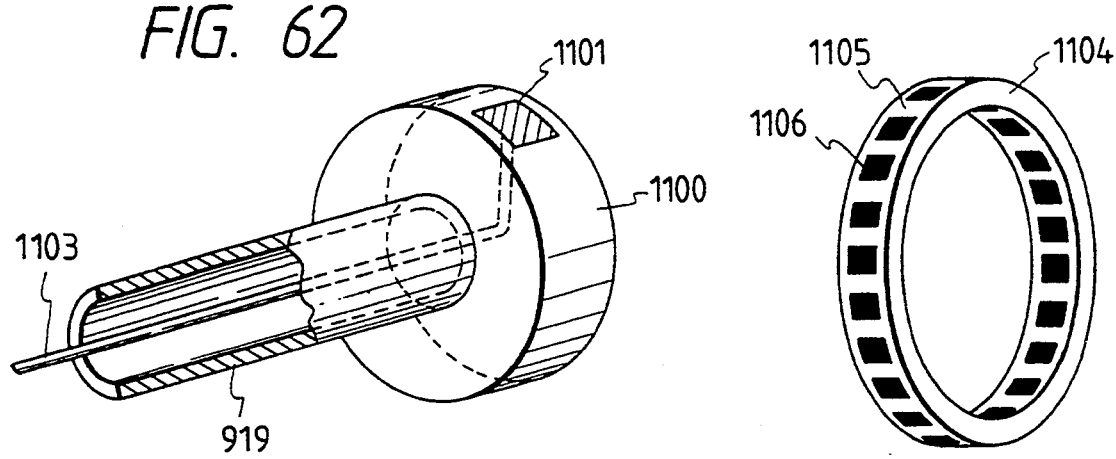
FIG. 62
FIG. 63
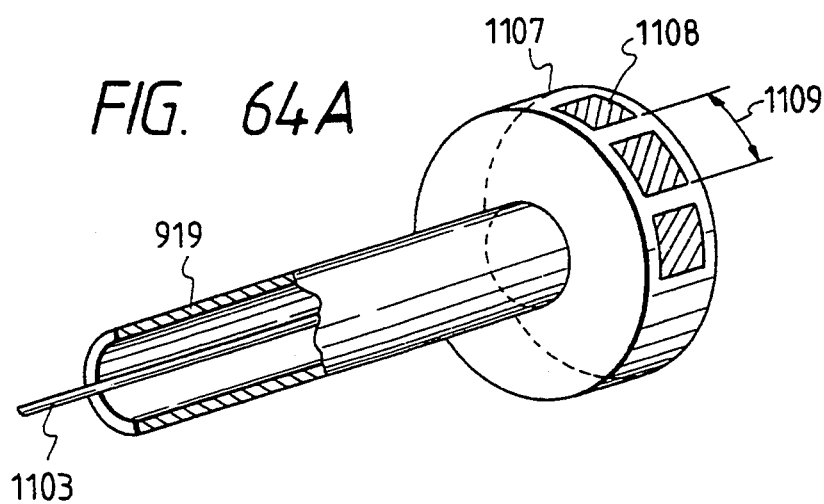
FIG. 64A
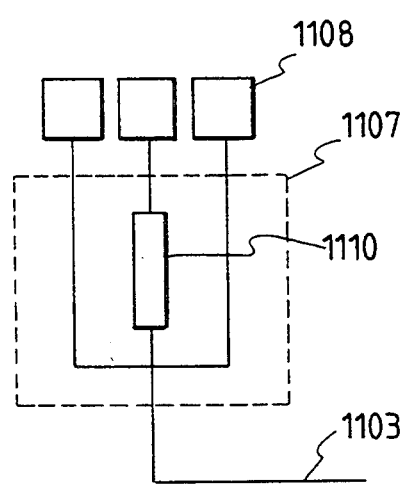
FIG. 64B

5,377,682

ULTRASONIC PROBE FOR TRANSMISSION AND RECEPTION OF ULTRASONIC WAVE AND ULTRASONIC DIAGNOSTIC APPARATUS INCLUDING ULTRASONIC PROBE

BACKGROUND OF THE INVENTION

The present invention relates to ultrasonic probes for transmitting and receiving an ultrasonic wave signal into and from an object such as a blood vessel having an extremely small diameter with the ultrasonic transmission direction being mechanically changed, and is applicable particularly, but not exclusively, to an ultrasonic diagnostic apparatus which is for obtaining an ultrasonic cross-sectional image of the object, and further relating to ultrasonic diagnostic apparatus equipped with an ultrasonic probe.

Recently, noted is an operation technique that a trouble such as a stricture and imperformation within a blood vessel is diagnosed and treated through a catheter such as disclosed in the document U.S. Pat. No. 5,000,185. However, since in conventional arrangements a guidewire is connected to a tip portion of the catheter, in the case of searching a narrow blood vessel, the entire catheter is required to operate within the blood vessel, and in addition, although the guidewire is required to move in accordance with the top of the catheter being moved toward a target portion within the blood vessel, difficulty is encountered to move the catheter when an extremely narrow blood vessel exists which does not allow the passage of the guidewire.

Moreover, for example, for inserting the catheter into a coronary artery of a heart, the outer diameter of the catheter is required to be reduced up to a predetermined value and hence the ultrasonic transducer is required to be extremely small and thin. However, the reduction of the thickness of the ultrasonic transducer tends to increase the oscillation frequency, thereby making it difficult to construct an ultrasonic probe which can transmit an ultrasonic wave having a desired frequency. According to the conventional ultrasonic probes, since there are a number of parts having complicated configurations, difficulty is encountered to reduce the dimension of the ultrasonic probe up to a desired degree. In addition, according to the conventional probes, the ultrasonic image (ultrasonic cross-sectional image) is limited to a two-dimensional ultrasonic image in the radial direction.

SUMMARY OF THE INVENTION

It is therefore an object of the present invention to provide an ultrasonic probe which is capable of being free in movement and having a simple structure and scanning an ultrasonic wave in a forward sector direction concurrently with the radial direction.

An ultrasonic probe according to the present invention to be used for an ultrasonic diagnostic apparatus comprises a catheter having a hollow tubing structure, a joint having a tubing structure and arranged to be at its one end portion connected to a tip portion of said catheter, a bearing connected to the other end portion of the joint, a rotating shaft inserted into the bearing to be rotatable and arranged so that a portion of the rotating shaft contacts with one end portion of the bearing, and a rotator connected to the rotating shaft and arranged so that one end portion of the rotator contacts with the other end portion of the bearing so that the bearing is interposed and supported between the portion of the rotating shaft and the rotator. An ultrasonic transducer is inserted into the rotator for transmitting and receiving an ultrasonic wave, a torque transmission shaft having a hollow structure is at its one end portion connected to the rotating shaft, and a guide wire is inserted into the hollow of the torque transmission shaft. A rotating force generated by a drive section is applied through the torque transmission shaft to the ultrasonic transducer whereby the ultrasonic transducer rotationally driven to perform a radial scanning operation. This arrangement allows a free movement of the guidewire within the catheter so that the catheter can easily be lead along the guidewire up to a target portion within a blood vessel.

Further, in accordance with this invention, there is provided an ultrasonic diagnostic apparatus comprising: an ultrasonic probe including: an ultrasonic transducer for transmission and reception of an ultrasonic wave to and from an object; a catheter having a hollow structure; a first torque transmission shaft having a hollow structure, the first torque transmission shaft being inserted into the catheter and connected to the drive section for receiving the driving force from the drive section; a second torque transmission shaft having a hollow structure, the second torque transmission shaft being inserted into the first torque transmission shaft and connected to the drive section for receiving the driving force from the drive section; a bearing having a hollow structure and fixedly connected to a tip portion of the catheter; a joint having a hollow structure and fixedly connected to a tip portion of the second torque transmission shaft, the joint having at its tip portion a thread portion and rotatable together with the second torque transmission shaft; a rotating shaft fixedly connected to a tip portion of the first torque transmission shaft so as to be rotatable together with the first torque transmission shaft, the joint being rotatably inserted in the rotating shaft; a mirror holder fixedly connected to the rotating shaft so as to be rotatable together with the rotating shaft, the mirror holder having a groove formed in directions of a longitudinal axis of the ultrasonic probe; a reflection mirror fixed to a tip portion of the mirror holder for changing a propagation direction of the ultrasonic wave from the ultrasonic transducer; and a transducer holder for holding the ultrasonic transducer, the transducer holder having a thread portion engaged with the thread portion of the joint and having a pin engaged with the groove of the mirror holder so as to limit a rotational direction of the mirror holder; an ultrasonic transducer for transmission and reception of an ultrasonic wave toward and from an object; a transmission and reception section connected to the ultrasonic transducer for supplying an ultrasonic signal transmission signal to the ultrasonic transducer whereby the ultrasonic transducer transmits the ultrasonic wave and for receiving a reflection signal from the ultrasonic transducer due to a reflected ultrasonic wave from the object; a signal processing section coupled to the transmission and reception section for receiving and processing an output of the transmission and reception section; a display section connected to the signal processing section for displaying an ultrasonic image in accordance with an output of the signal processing section; a control section for outputting first and second control signals in accordance with an instruction by an operator; a drive section for generating a drive force in accordance with the first control signal from the control section; and a lock section coupled to the drive section and the first and second torque transmission shafts, and further coupled to the second control signal from the control section so as to simultaneously rotate the first and second torque transmission shafts or rotate only the first torque transmission shaft in accordance with the second control signal from the control section.

Moreover, according to this invention, there is provided an ultrasonic diagnostic apparatus comprising: a catheter having a flexible hollow structure and having a plurality of microlumens; a shaft having a hollow structure and fixed to a tip portion of the catheter; a bearing having a hollow structure and made of a material having a small frictional coefficient; a rotating shaft inserted into the hollow portions of the shaft and the bearing; a rotator which is fixed to a tip portion side of the rotating shaft and in which a peripheral direction ultrasonic transducer and an ultrasonic wave reflecting mirror are disposed in opposed relation to each other, the rotator having a tubing structure and having an opening for emitting an ultrasonic wave generated by the peripheral direction ultrasonic transducer and reflected by the reflecting mirror; an eccentric shaft fixed to a tip portion side of the rotator; a transducer holder rotatably supported by a pivot shaft and having at its rear end portion a groove engaged with the eccentric shaft so as to be sectrally movable about the pivot shaft; a forward direction ultrasonic transducer provided within the transducer holder; a cap fixed to the bearing, the pivot shaft being fixed to the cap; a torque transmission shaft fixed to a rear end portion of the rotating shaft and having a flexible multi-layered structure for transferring a rotating force; a first signal line passing through the lumen of the catheter and electrically connected to the forward direction ultrasonic transducer; a second signal line passing through the inside of the torque transmission shaft and electrically connected to the peripheral direction ultrasonic transducer; a probe side connector fixed to a rear end portion of the torque transmission shaft; a main body side connector engageable with the probe side connector; a signal contact portion electrically connected to the second signal line disposed within the torque transmission shaft; a second rotating shaft connected to the main body side connector; a motor for rotating the second rotating shaft; a position detector for detecting a rotating state of the motor; and an image forming section for forming ultrasonic images, corresponding to ultrasonic wave generated from the ultrasonic transducers and returned to the ultrasonic transducers, on the basis of an output signal of the position detector.

BRIEF DESCRIPTION OF THE DRAWINGS

The object and features of the present invention will become more readily apparent from the following detailed description of the preferred embodiments taken in conjunction with the accompanying drawings in which:

FIG. 10 is a block diagram showing an arrangement of an ultrasonic diagnostic apparatus including the FIGS. 9A and 9B ultrasonic probe;

FIGS. 25A and 25B are cross-sectional views showing an arrangement of a drive section of an ultrasonic diagnostic apparatus according to a sixteenth embodiment of this invention;

FIGS. 30A to 30D are detailed illustrations of a torque transmission shaft of an ultrasonic probe of the FIG. 29 ultrasonic diagnostic apparatus;

FIG. 47 shows an arrangement of a position sensor to be used in the FIG. 46 ultrasonic diagnostic apparatus;

FIG. 48A shows an output of the FIG. 47 position sensor;

FIG. 48B shows an output of a reception section obtained on the basis of the position sensor output;

FIG. 48C shows a position signal of a position signal generating section;

FIG. 62 is an enlarged illustration of the disc-like electrode of the FIG. 59 ultrasonic probe;

FIG. 63 is an illustration of a ring-like electrode which can be used for the FIG. 59 ultrasonic diagnostic apparatus;

FIG. 64A shows an arrangement of a disc-like electrode of an ultrasonic probe to be used for an ultrasonic diagnostic apparatus according to a thirty second embodiment of this invention;

FIG. 64B is a block diagram showing an electric connection between electrodes of the disc-like electrode and a signal line;

DETAILED DESCRIPTION OF THE INVENTION

Figure 1:
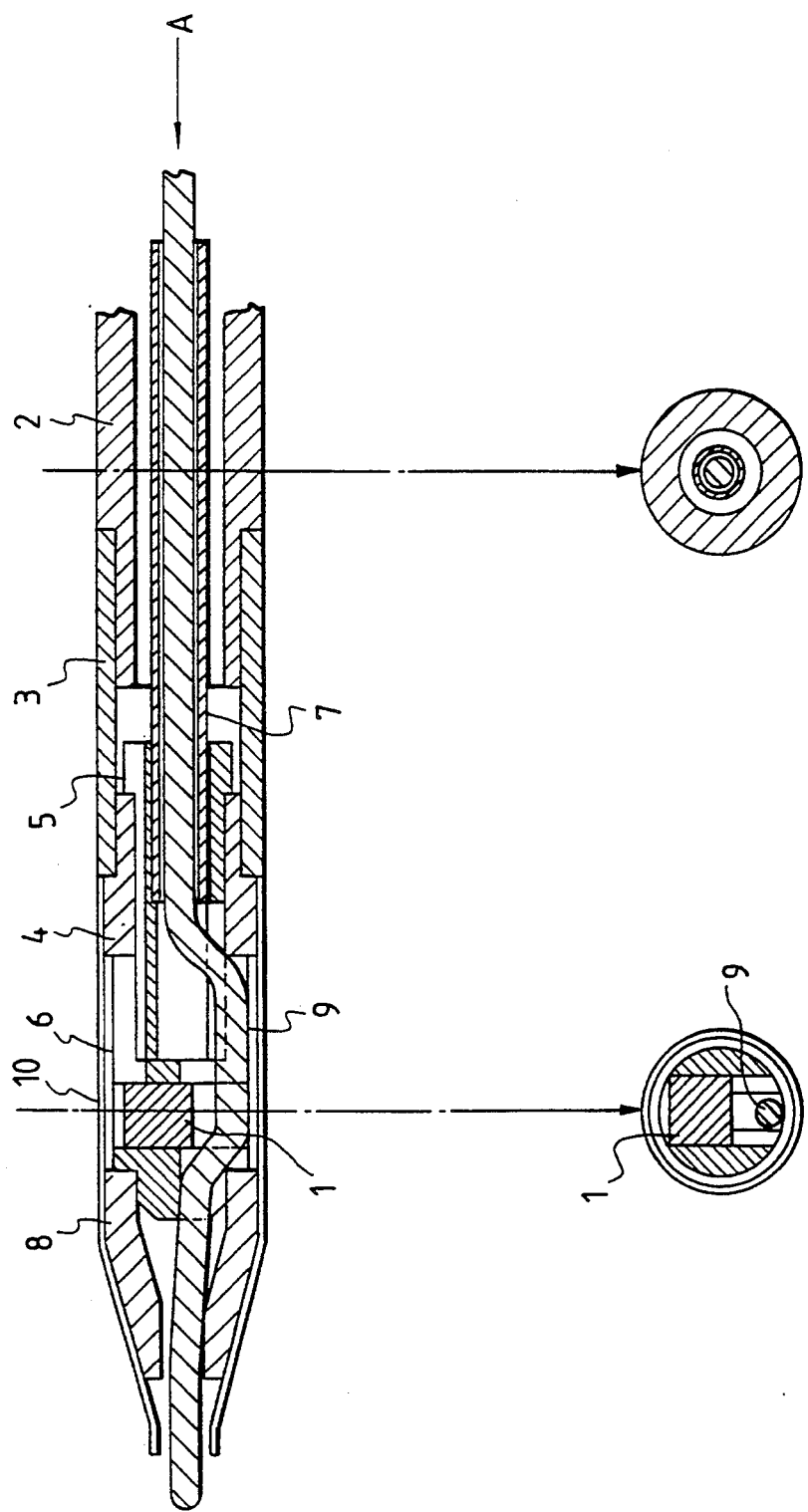
FIG. 1 is a cross-sectional view showing an arrangement of an ultrasonic probe according to a first embodiment of the present invention.

FIG. 1 is a cross-sectional view showing an arrangement of an ultrasonic probe according to a first embodiment of the present invention. In FIG. 1, numeral 1 represents an ultrasonic transducer for transmitting and receiving an ultrasonic wave, 2 designates a catheter, 3 denotes a joint connected or joined to a tip portion of the catheter 2, 4 depicts a bearing connected to the joint 3, 5 indicates a rotating shaft which contacts with the inner surface of the bearing 4 to rotationally operates, and 6 is a rotator for holding the bearing 4 in cooperation with the rotating shaft 5. The ultrasonic transducer 1 is inserted into a cylindrical transducer insertion hole formed in the rotator 6. Further, 7 represents a torque transmission shaft, 8 designates a cap, 9 denotes a guidewire, 10 indicates a protective coat for covering the bearing 4 and the cap 8.

More specifically, the joint 3 made of a hard material and having a hollow (tubing) structure is at its one end portion secured fixedly to the tip portion of the catheter 2 made of a resin such as a Teflon and polyethylene and having a hollow structure. The bearing 4 is inserted into the other end portion of the joint 3 and fixed. That is, the catheter 2 and the bearing 4 are coupled to each other through the joint 3. Before the connection between the bearing 4 and the joint 3, the rotating shaft 5 is inserted into the bearing 4, having a hollow structure, from a direction indicated by an arrow A in FIG. 1. The rotating shaft 5 can be arranged to freely rotates with respect to the bearing 4, and the tip portion of the rotating shaft 5 is protruded from the bearing 4 and is inserted into a rotating-shaft guiding hole 32 formed in the rotator 6 and fixed after inserted thereinto. That is, the bearing 4 is held by both the rotating shaft 5 and the rotator 6 whereby the rotator 6 is rotatable together with the rotating shaft 5 without being disconnected from the bearing 4.

Figure 2:
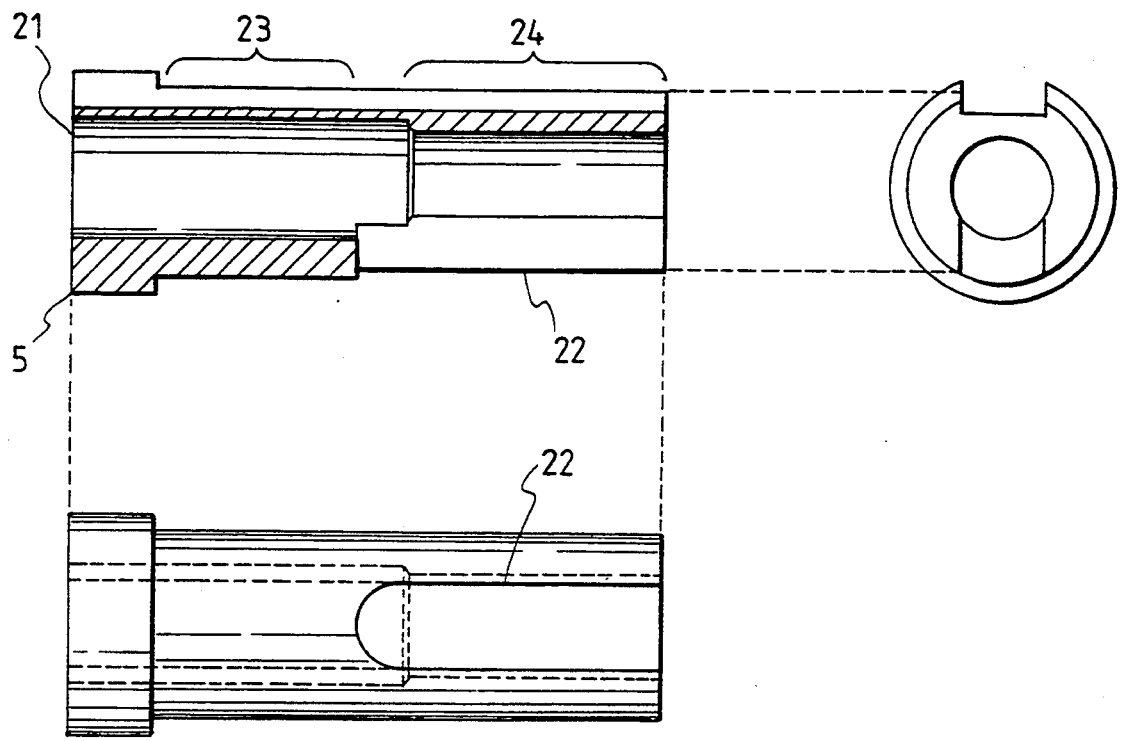
FIG. 2 shows an arrangement of a rotating shaft of the FIG. 1 ultrasonic probe.
Figure 3:
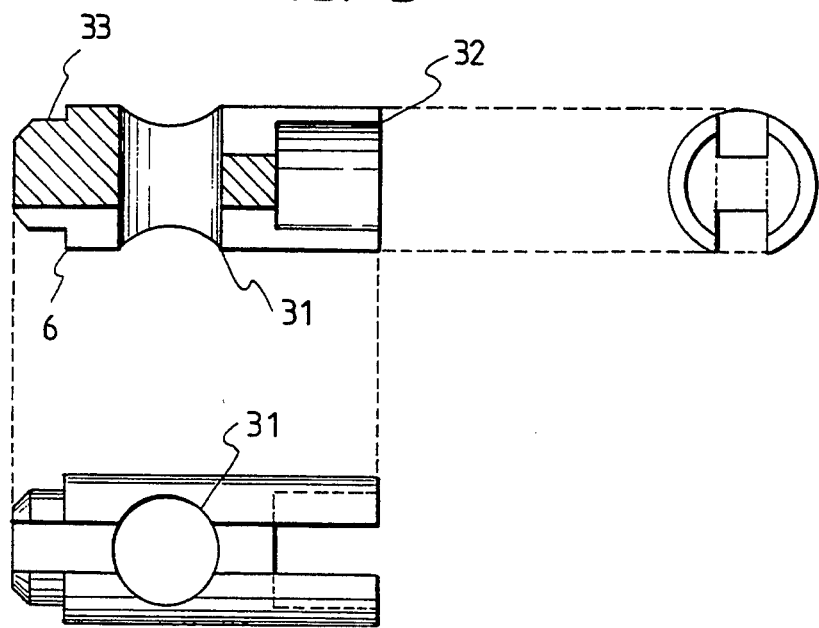
FIG. 3 shows an arrangement of a rotator of the FIG. 1 ultrasonic probe.

FIG. 2 shows an arrangement of the rotating shaft 5. In FIG. 2, numeral 21 represents a spring insertion hole, 22 designates a guidewire clearance (escaping) groove, 23 indicates a bearing contact portion, and 24 is a rotator insertion hole. Further, FIG. 3 shows an arrangement of the rotator 6. In FIG. 3, numeral 31 is a transducer insertion hole, 32 designates a rotating-shaft guide hole and 33 indicates a cap contact portion. The bearing 4 is inserted up to the bearing contact portion 23 of the rotating shaft 5 and then the rotator insertion portion 24 of the rotating shaft 5 is fixed to the rotating-shaft guide hole 32 of the rotator 6, whereby the bearing 4 is held or interposed between the rotating shaft 5 and the rotator 6 to allow the rotating shaft 5 and the rotator 6 to rotate with respect to the bearing 4. The bearing 4 held by the rotating shaft 5 and the rotator 6 is connected to the joint 3.

The ultrasonic transducer 1 is fixed to the transducer insertion hole 31 of the rotator 6 and coupled to a signal line, not shown. The torque transmission shaft 7 passes through the inside of the catheter 2 and further passes through the hollows of the joint 3 and the bearing 4 so as to be inserted into the spring insertion hole 21 of the rotating shaft 5. The guidewire 9 passes through the hollow of the torque transmission shaft 7 and further passes through the spring insertion hole 21 and the guidewire of the rotating shaft 5 and once direct to the lower side of the rotator 6 and again direct through a cavity (space) at the tip portion of the rotator 6 to the tip portion of the catheter 2 as illustrated in FIG. 1. Since the guidewire 9 are not fixed at the portions through which the guidewire 9 passes, only the guidewire 9 is freely movable. The cap contact portion 33 of the rotator 6 is inserted into the inside of the cap 8 so as to prevent the axis of the rotator 6 from being deflected or vibrated during the rotation of the rotator 6. The cap 8 is configured to be tapered toward its tip portion so as to make easy the insertion of the catheter 2 into the blood vessel. The cap 8, together with the bearing 4, is covered by the protective coat having an extremely thin thickness. The protective coat 10 may be made of a material having a heat contraction characteristic whereby the protective coat 10 can adequately cover the cap 10 even if being tapered toward its tip portion. This protective coat can prevent the bearing 4 and others from damaging the inner wall of the blood vessel irrespective of the movement of the catheter 2 in the blood vessel.

In operation, first, for moving the catheter 2 up to the target diseased part, the guidewire 9 having a diameter extremely smaller than the outer diameter of the catheter 2 is inserted into the blood vessel and moved up to a position beyond the diseased part. Then, the catheter 2 is moved along the guidewire 9 so as to reach the target diseased part. When the catheter 2 is positioned at the vicinity of the diseased part, the tip portion of the guidewire 9 is once brought back to the rear side of the rotating-shaft guide hole 32 of the rotator. In this state, the torque transmission shaft 7 is rotated by means of a driving section positioned at the rear end portion of the catheter 2. This rotation driving force rotates the rotating shaft 5 and the rotator 6 through the torque transmission shaft 6. Due to the rotation of the rotator 6, the ultrasonic transducer 1 rotated in the radial direction. Here, an ultrasonic wave transmission signal is supplied through the signal line, not shown, to the ultrasonic transducer 1. In response to the ultrasonic wave transmission signal, the ultrasonic transducer 1 generates an ultrasonic wave which in turn passes through the protective coat 10 so as to propagate within the blood vessel and reflect at various portions due to the difference between the acoustic impedances to again return to the ultrasonic transducer 1. The ultrasonic transducer 1 converts the returned ultrasonic wave into an electric signal. This reflection signal is supplied through the signal line to a main body disposed at the rear end portion of the catheter 2 so as to display an ultrasonic image on a display apparatus. The unshown signal line is disposed to extend from the ultrasonic transducer 1 to the inside of the rotator 6 and then direct in the space (gap) between the torque transmission shaft 7 and the guidewire 9 or along the outer surface of the torque transmission shaft 7, whereby the signal line can be prevented from being twisted due to the rotation of the torque transmission shaft 7. The space between the rotator 6 and the protective coat 10 is filled with a liquid such as a physiological salt water which can effectively propagate the ultrasonic wave and which does not impair the human body. It is also appropriate that the blood is injected from the top portion thereinto.

Although, when the target portion is a coronary artery, the outer diameter of the catheter 2 is required to be below φ2, the parts of the ultrasonic probe according to this invention can be arranged in order to several hundred microns and can be manufactured by means of the electric discharge machining or the like. Further, although the inner diameter of the catheter 2 is about φ1, the torque transmission shaft 7 to be provided within the catheter 2 is constructed with a plurality of elongated members (wires) each having a dimension of several times of ten microns being arranged in parallel to each other and coiled to form a spring-like layer, whereby it is possible to ensure a sufficient space to pass the guidewire 9 concurrently with transmitting the rotationally driving force. In addition, for the ultrasonic transducer 1 to be inserted into the insertion hole 31 of the rotator 6, it is possible to insure a space close to the diameter of the insertion hole in the thickness direction.

As described above, the joint 3 having a hollow structure is connected and fixed to the tip portion of the catheter 2, the bearing 4 is inserted into the opposite side of the joint 3 to be fixedly secured therein, the rotating shaft 5 is inserted into the inside of the bearing 4, and the rotator 6 is provided at the opposite side of the bearing 4 so as to be fixed to be freely rotatable with respect to the inner surface of the bearing 4. Thus, with an extremely simple structure and a small number of parts, a mechanism for allowing rotation of the ultrasonic transducer 1 in the radial direction can be constructed with respect to the small-diameter catheter 2. In addition, with the guide wire 9 passing through the inside of the torque transmission shaft 7 and the inside of the rotator 6 to advance ahead of the catheter 2, the guidewire 9 can be arranged to be movable independently of the catheter 2.

Figure 4:
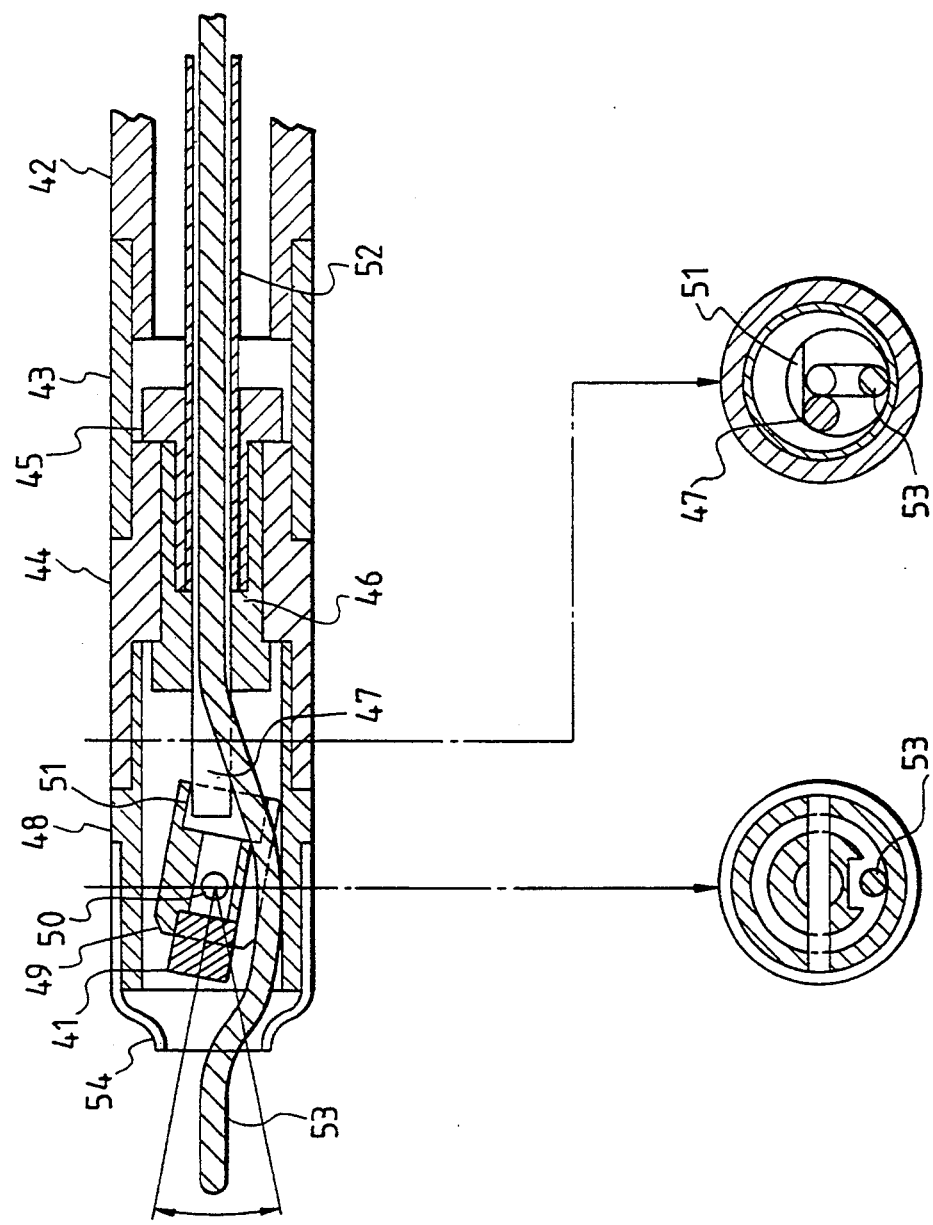
FIG. 4 is a cross-sectional view showing an arrangement of an ultrasonic probe according to a second embodiment of this invention.

Further, a second embodiment of this invention will be described hereinbelow with reference to FIG. 4. In FIG. 4, numerals 41 represents an ultrasonic transducer for transmission and reception of an ultrasonic wave, 42 designates a catheter, 43 depicts a first joint connected to the tip portion of the catheter 42, 44 denotes a bearing connected to the first joint 43, 45 indicates a rotating shaft which contacts with the inner surface of the bearing 44 to rotate, 46 is a rotatable head portion which, together with the rotating shaft 45, holds the bearing 44 and which is equipped with an eccentric shaft 47 having a semicylindrical configuration, 48 represents a second joint coupled to the bearing 44, 49 designates a transducer holder into which the ultrasonic transducer 41 is inserted, and 50 denotes a pivot shaft which acts as a sectral scanning central shaft provided on the transducer holder 49. Further, numeral 51 is groove which is provided on the transducer holder 49 to come into contact with the eccentric shaft 47, 52 depicts a torque transmission shaft connected to the rotating shaft, 53 is a guidewire, and 54 is a protective coat which covers the second joint 48.

More specifically, the first joint 43 made of a hard material and having a hollow structure is connected and secured fixedly to the tip portion of the catheter 42 made of a resin such as a Teflon and polyethylene and having a hollow structure, and the bearing 44 is inserted into the other end portion of the first joint 43, which is opposite to the connection side to the catheter 42, and fixed thereto. That is, the catheter 42 and the bearing 44 are coupled to each other through the first joint 43. As well as in the above-described first embodiment, the rotating shaft 45 is inserted into the inside of the; bearing 44, having the hollow structure, before the connection between the bearing 44 and the first joint 43. The rotating shaft 45 is freely rotatable with respect to the bearing 44 and the tip portion of the rotating shaft 45 protrudes beyond the bearing 44 and inserted into the rotatable head portion 46 and fixed thereto. That is, the bearing 44 is interposed between the rotating shaft 45 and the rotatable head portion 46 whereby the rotatable head portion 46, together with the rotating shaft 45, is rotatable without being disconnected to the bearing 44. On the tip portion of the rotatable head portion 46 the eccentric shaft 47 is provided at a position shifted from the rotation center axis, and the eccentric shaft 47 is brought into contact with the groove 51 formed in the transducer holder 49. The transducer holder 49 can take a sector action by the pivot shaft 50 with respect to the front side of the catheter 42. The pivot shaft 50 is fixedly secured to the second joint 48. The torque transmission shaft 52 having a hollow structure passes through the inside of the catheter 42 and is inserted into the rotating shaft 45 which is inserted into the bearing 44. The guidewire 53 passes through the hollow portion of the torque transmission shaft 52 and further passes through the insides of the rotating shaft 45 and the rotatable head portion 46 and then extends from the tip portion of the catheter 42 up to the outside of the catheter 42 along the passage shown in FIG. 4. The protective coat 54 covers the second joint 48 and the tip portion of the protective coat 54 is tapered to thereby make easy the insertion into the blood vessel. Here, it is desired that the ultrasonic wave propagation area portion of the ultrasonic transducer 41 is opened to form an opening for the sectral scanning due to the transducer holder 49. As well as in the above-described first embodiment, the ultrasonic transducer 42 is connected to a signal line, not shown, and is responsive to an electric signal.

In operation, first, in order for moving the catheter 42 up to the target diseased part, the guidewire 53 having a diameter extremely smaller than the inner diameter of the catheter 42 is inserted into the blood vessel and then moved up to a position ahead of the tip portion of the diseased part. The catheter 42 is moved along the guidewire 53 so as to reach the target diseased part. When the catheter 42 is positioned at the vicinity of the diseased part, the tip portion of the guidewire 53 is once returned up to a rear position of the rotatable head portion 46. In this state, the torque transmission shaft 52 is rotated by means of a drive section positioned at the read side of the catheter 42. This rotating force is transferred through the torque transmission shaft 52 to the rotating shaft 45 and the rotatable head portion 46 which are in turn rotated. Due to the rotation of the rotatable head portion 46, the eccentric shaft 47 rotates with respect to the rotation center axis of the rotatable head portion 46. This eccentric shaft 47 is disposed so as to be brought into contact with the groove 51 of the transducer holder 49. Since the operating direction of the transducer holder 49 is limited by the pivot shaft 50, only the up and down (vertical) operation of the rotating operation of the eccentric shaft 47 is transferred to the transducer holder 49. Accordingly, the ultrasonic transducer 42 inserted into the transducer holder 49 can be sector-operated with respect to the front side of the catheter 42. During this sector-operation, an ultrasonic wave transmission signal is supplied through the unshown signal line to the ultrasonic transducer 41. In response to the ultrasonic wave transmission signal, the ultrasonic transducer 41 transmits an ultrasonic wave which is in turn outputted from the opening portion of the protective coat 54 to propagate within the blood vessel and reflect at various portions due to the difference between the impedances to again return to the ultrasonic transducer 41. The returned ultrasonic wave is converted into an electric signal. This reflection signal is supplied through the signal line to a main body positioned at the rear side of the catheter 42 so as to display a two-dimensional ultrasonic image on a display apparatus. The unshown signal line is disposed to extend from the ultrasonic transducer 41 to the rotatable head portion 46 and direct within the space between the torque transmission shaft 52 and the guidewire 53 or direct along the outside of the torque transmission shaft 52, thereby preventing the signal line from being twisted irrespective of the rotation of the torque transmission shaft 52.

As described above, according to this embodiment, the first joint 43 having a hollow structure is connected to the tip portion of the catheter 42, the bearing 44 is inserted and fixed to the opposite side of the first joint 43, the rotating shaft 45 is inserted into the inside of the bearing 44 and the rotatable head portion 46 is inserted into the opposite side of the bearing 44 so as to be freely rotatable with respect to the inner surface of the bearing 44. In addition, the eccentric shaft 47 is provided on the rotatable head portion 46 and hence, due to the rotatable head portion 46 and the groove 51 of the transducer holder 49, the ultrasonic transducer 41 can be sector-operated about the pivot shaft 50 with respect to the front side of the catheter 42. Moreover, the guidewire 53 passes through the torque transmission shaft 52 and the rotatable head portion 46 to advance ahead of the catheter 42, and therefore the guidewire 53 can be arranged to be movable independently of the catheter 42.

Figure 5:
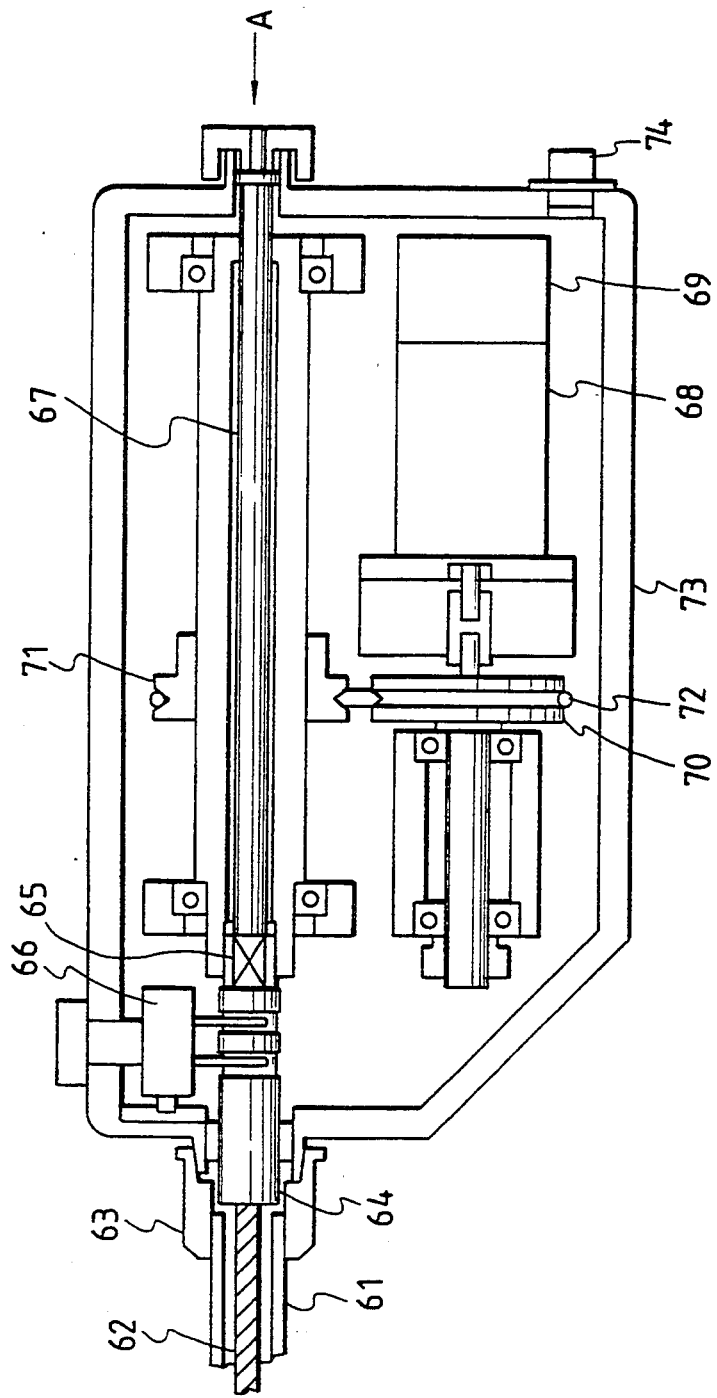
FIG. 5 is a cross-sectional view showing an arrangement of an ultrasonic probe according to a third embodiment of this invention.

A third embodiment of this invention will be described hereinbelow with reference to FIG. 5. In FIG. 5, numeral 61 represents a catheter, 62 designates a torque transmission shaft, 63 depicts a probe side fitting portion, 64 is a probe side connector, and 65 denotes a contact hole provided in the probe side connector 64. These portions correspond to the rear end portions of the ultrasonic probe described in the first and second embodiments. Further, numeral 66 represents a signal contact portion, 67 indicates a guide tube, 68 is a motor, 69 designates an encoder connected to the rotating shaft of the motor 68, 70 denotes a first pulley connected to the motor 68, 71 is a second pulley connected to the guide tube 67, 72 is a drive belt for transferring the rotating force of the first pulley 70 to the second pulley 71, 73 represents a drive section, and 74 is a connector provided in the drive section 73 for the connection to a main body.

In operation, the catheter 61 is at its rear end portion connected to the probe side fitting portion 63. The probe side connector 64 is connected and fixed to the torque transmission shaft 62 within the catheter 61. In order to sufficiently deriving the drive transmission of the torque transmission shaft 62, this connection is made so as to prevent the occurrence of a deflection. The rear end portion of the ultrasonic probe thus arranged can easily be disconnected from the drive section 73 by means of the probe side fitting portion 63. The contact hole 65 of the probe side connector 64 of the ultrasonic probe attached to the drive section 73 is automatically connected to a projection having the same configuration as the contact hole 65 provided at the tip portion of the guide tube 67. The guide tube 67 and the probe side connector 64 have hollow structures and the guide wire is inserted into the hollows of the guide tube 67 and the probe side connector 64 from the direction indicated by an arrow A in FIG. 5 and supplied up to the tip portion of the ultrasonic probe. This guide tube 67 is responsive to the rotational driving force of the motor 68 through the second pulley 71, drive belt 72 and first pulley 70 so as to rotate the probe side connector 64 connected to the guide tube 67 and the torque transmission shaft 62 connected to the probe side connector 64, thereby transmitting the rotational driving force up to the tip portion of the catheter 61. The probe side connector 64 has a slip ring configuration and is at it inside connected to a signal line, not shown, from the tip portion of the catheter 61. The electric signal of the probe side connector 64 is derived by a blush of the signal contact portion 66. This electric signal, together with a motor drive signal and the output signal of the encoder 69, coupled through the connector 74 to a main body, not shown. In the main body, a two-dimensional ultrasonic image is displayed on a display apparatus in accordance with the output signal of the ultrasonic transducer and the motor rotational position signal which is the output signal of the encoder 69.

According to this embodiment, the probe side fitting portion 63 and the probe side connector 64 are provided at the rear end portion of the catheter 61 of an ultrasonic probe having the same arrangement as the ultrasonic probe described above as the first or second embodiment, and in the drive section 73 to be coupled to the catheter 61 there are provided the guide tube 67, signal contact portion 66, motor 68, encoder 69, first pulley 70, second pulley 71, drive belt 72 and connector 74, whereby the ultrasonic probe can easily be connected to the guide tube 67 in the drive section 73. This arrangement allows the use of a different type of ultrasonic probe. In addition, the guidewire can easily be inserted from the read side of the guide tube 67 into the torque transmission shaft 62 within the catheter 61.

Figure 6:
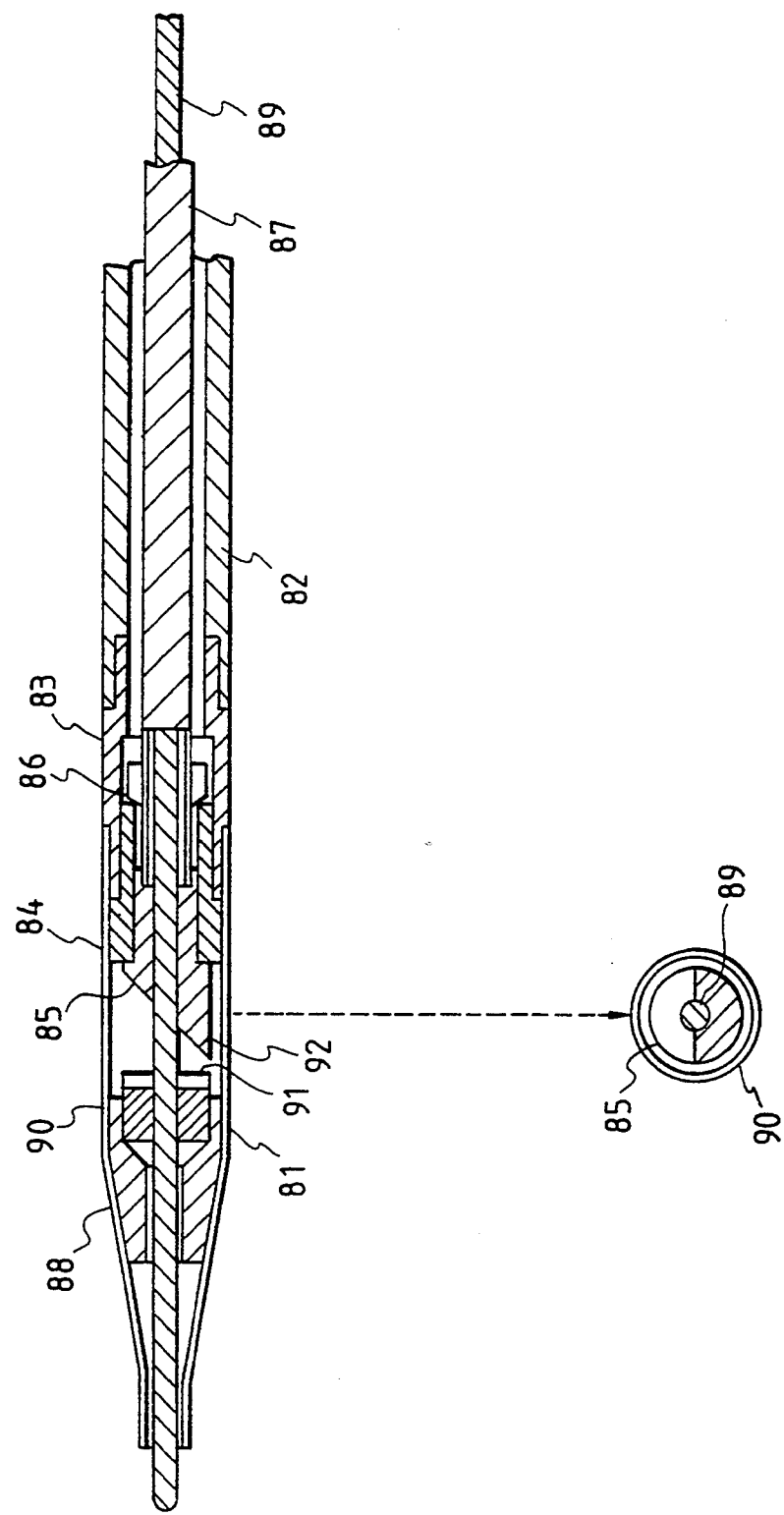
FIG. 6 is a cross-sectional view showing an arrangement of an ultrasonic probe according to a fourth embodiment of this invention.

A description will be made hereinbelow in terms of a fourth embodiment of this invention. FIG. 6 is a cross-sectional view showing an arrangement of an ultrasonic probe according to the fourth embodiment of this invention. In FIG. 6, a joint 83 made of a hard material and having a hollow structure is at its one end portion secured fixedly to the tip portion of a catheter 82 made of a resin such as a Teflon and polyethylene and having a hollow structure. A bearing 84 is inserted and connected to the other end portion of the joint 83. That is, the catheter 82 and the bearing 84 are coupled to each other through the joint 83. Into the inside of the bearing 84 having a hollow structure there is inserted a mirror 85 whose rear end portion is stopped by a stopping member 86 so that the mirror 85 is prevented from being disconnected from the bearing 84. The mirror 85 is freely rotatable with respect to the bearing 84. An ultrasonic transducer 81 is positioned to be in opposed relation to the tip portion of the mirror 85 and is fixedly secured to a transducer holder 88. The transducer holder 88 is tapered so as to make easy the insertion of the catheter 82 into a blood vessel. The transducer holder 88, together with the bearing 84, is converted by a protective coat 90 having an extremely thin thickness. This protective coat 90 is made of a heat contraction characteristic so as to adequately cover the transducer holder 88 which becomes thinner toward the tip portion. This protective coat 90 prevents the bearing 84 and others from damaging the blood vessel irrespective of the movement of the catheter 82 within the blood vessel. Illustrated at numeral 87 is a torque transmission shaft which has a hollow structure and which is inserted into the catheter 82 and further inserted and fixed to the mirror 85. A guidewire 89 is inserted into the hollow of the torque transmission shaft 87 and passes through a guidewire guiding hole 92 formed in the mirror 85 and a guidewire guide hole 91 formed in the ultrasonic transducer 81 so as to advance through the tip portion of the protective coat 90 into the blood vessel. The guidewire 89 is freely movable without being obstructed by the catheter 81. The ultrasonic transducer 81 is connected to a signal line, not shown, which is disposed to pass between the mirror 85 and the bearing 84 and further pass through the gap between the torque transmission shaft 87 and the guidewire 89 or advance along the outside of the torque transmission shaft 87. Thus, the signal line can be prevented from being twisted due to the rotation of the torque transmission shaft 87.

In operation, first, for moving the catheter 82 up to a target diseased part, the guidewire 89 having a diameter extremely smaller than that of the catheter 82 is inserted in the blood vessel and moved up to a position beyond the target diseased part. The catheter 82 is moved along the guidewire 89 up to the target diseased part. When the catheter 82 reaches a position at the vicinity of the target diseased part, the guidewire 89 is brought back so that the tip portion of the guidewire 89 takes a position behind the guidewire guiding hole 92 of the mirror 85. In this state, the torque transmission shaft 87 is rotated by means of a drive section, not shown, which is positioned at the rear end side of the catheter 82. This rotational driving force rotates the mirror 85 through the torque transmission shaft 87. In this state, an ultrasonic wave transmission signal is supplied through a signal line, not shown, to the ultrasonic transducer 81. In response to the ultrasonic wave transmission signal, the ultrasonic transducer 81 transmits an ultrasonic wave which is in turn reflected in the radial directions of the catheter 82 by means of the mirror 85 so as to propagate through the protective coat 90 into the blood vessel. The ultrasonic wave propagating within the blood vessel is reflected at various portions due to the difference between the impedances and again returned toward the mirror 85 and reflected on the mirror 85 toward the ultrasonic transducer 81. In response to the reflection ultrasonic wave, the ultrasonic transducer 81 generates an electric signal which is in turn supplied through the signal line to the main body which is positioned at the rear end side of the catheter 82, thereby displaying an ultrasonic image on a display apparatus. As well as the above-mentioned first and second embodiments, a plurality of elongated members each having a dimension of several ten microns are arranged and coiled so as to construct the torque transmission shaft having a sufficient inside space for the insertion of the guidewire 89. This arrangement can use the ultrasonic transducer 81 having a dimension close to the inner diameter of the catheter 82.

As described above, the joint 83 is connected and fixed to the tip portion of the catheter 82, the bearing 84 is inserted and fixed to the other end portion of the joint 83, and the mirror 85 is inserted into the bearing 85 and stopped by the stopping member 86, and hence it is possible to simply realize a mechanism, whereby the ultrasonic transducer 81 is rotationally drive in the radial direction, within the catheter 82 using small number of parts. In addition, since the guidewire 89 is arranged to pass through the torque transmission shaft 87 and the guidewire guiding holes 92 and 91 of the mirror 85 and the ultrasonic transducer 81, the guidewire 89 can be arrange to be movable independently of the catheter 82.

Figure 7:
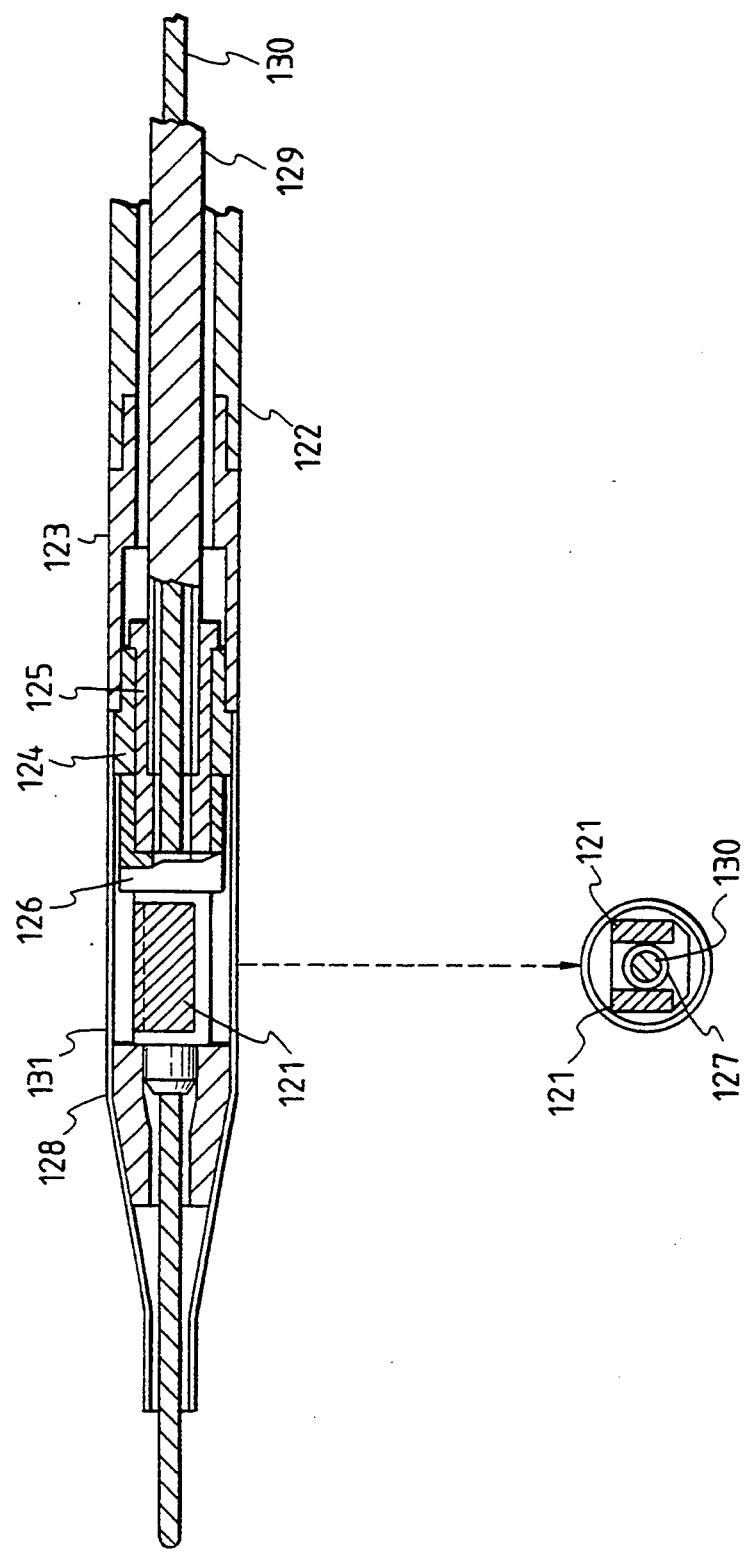
FIG. 7 is a cross-sectional view showing an arrangement of an ultrasonic probe according to a fifth embodiment of this invention.

Further, a description will be made hereinbelow in terms of a fifth embodiment of this invention. FIG. 7 is a cross-sectional view showing an arrangement of an ultrasonic probe according to the fifth embodiment of this invention. In FIG. 7, a joint 123 having a hollow structure and made of a hard material and having a hollow structure is at its one end portion secured fixedly to the tip portion of a catheter 122 made of a resin such as a Teflon and polyethylene and having a hollow structure. A bearing 124 is inserted and fixed to the other end portion of the joint 123 so that the catheter 122 and the bearing 124 are coupled to each other through the joint 123. Before the connection between the bearing 124 and the joint 123, a rotating shaft 125 is inserted into the inside of the bearing 124. The tip portion of the rotating shaft 125 protrudes from the bearing 124 and is connected to a rotator 126 so that the bearing 124 is interposed between the rotating shaft 125 and the rotator 126. This rotator 126 is freely rotatable with respect to the bearing 124. An ultrasonic transducer 121 is divided into two portions which are in turn disposed at both sides of a guidewire guiding hole 127 of the rotator 126. A cap 128 is positioned at the tip portion of the rotator 126 so as to prevent the deflection of the rotator 126 during the rotation. A torque transmission shaft 129 having a hollow structure is inserted into the catheter 122 and fixedly connected to the rotator 126. A guidewire 130 is inserted into the hollow of the torque transmission shaft 129 and passes through the guidewire guiding hole 127 of the rotator 126 and advances through the tip portion of the cap 128 into a blood vessel. Further, the guidewire 130 is freely movable without being obstructed by the catheter 122. As well as the above-described fourth embodiment, the ultrasonic transducer 121 transmits an electric signal for obtaining a two-dimensional ultrasonic image.

In operation, first, for moving the catheter 122 up to a target diseased part within a blood vessel, the guidewire 130 is inserted into the blood vessel and moved up to a position beyond the target diseased part and then the catheter 122 is moved along the guidewire 130 whereby the catheter 122 having a diameter greater than the guidewire 130 can smoothly reach the target diseased part. In this state, the torque transmission shaft 129 is rotationally driven by a drive section provided at the read end side of the catheter 122. This rotational driving force rotates the rotating shaft 125, rotator 126 and the ultrasonic transducer 121 through the torque transmission shaft 129. In this state, an ultrasonic wave transmission signal is supplied through an unshown signal line to the ultrasonic transducer 121 whereby the ultrasonic transducer 121 radially scans the blood vessel with an ultrasonic wave. The ultrasonic transducer converts the reflection ultrasonic wave from the blood vessel into an electric signal which is in turn supplied to a main body so as to display a two-dimensional ultrasonic image on a display apparatus.

Figure 8:
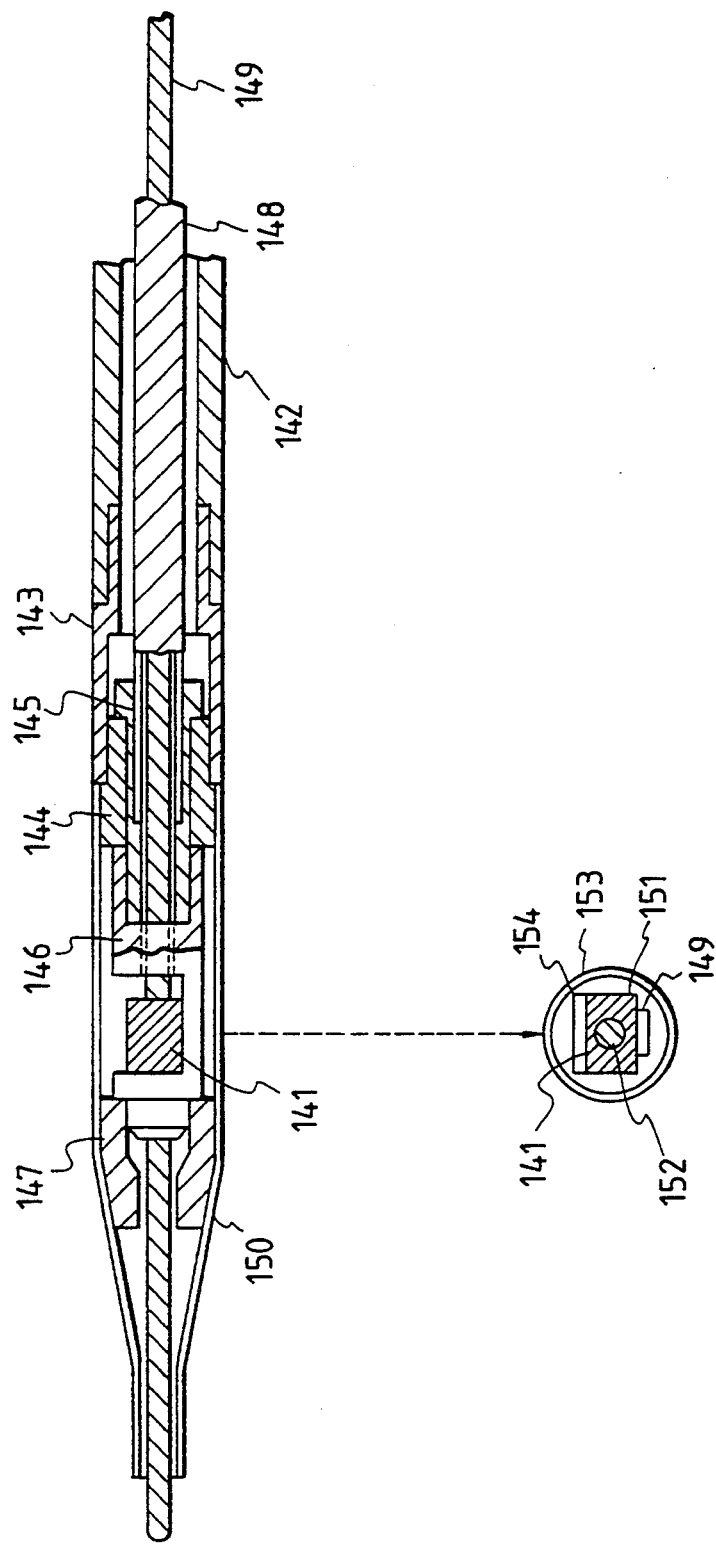
FIG. 8 is a cross-sectional view showing an arrangement of an ultrasonic probe according to a sixth embodiment of this invention.

Still further, a description will be made hereinbelow in terms of a sixth embodiment of this invention. FIG. 8 is a cross-sectional view showing an arrangement of an ultrasonic probe according to the sixth embodiment of this invention. In FIG. 8, numerals 151 represents a backing member, 152 designates a guidewire guiding hole formed in the backing member 151, 153 depicts a piezoelectric plate, and 154 denotes an acoustic matching layer. An ultrasonic transducer 141 comprises the backing member 151, piezoelectric plate 153 and acoustic matching layer 154. A joint 143 having a hollow structure is fixedly connected to the tip portion of a catheter 142 and a bearing 144 is fixedly inserted into the opposite side of the joint 143 so that the catheter 142 and the bearing 144 are coupled to each other through the joint 143. Before the connection between the bearing 144 and the joint 143, a rotating shaft 145 is inserted into the inside of the bearing 144 so as to be freely rotatable with respect to the bearing 144 as well as in the fifth embodiment. The ultrasonic transducer 141 is fixedly connected to a rotator 146 and the guidewire guiding hole 152 of the backing member 151 is coupled to the hollow of the rotator 146. A cap 147 is positioned at the tip portion of the ultrasonic transducer 141 and is covered, together with the bearing 144, by a protective coat 150. A torque transmission shaft 148 is inserted into the catheter 142 and fixedly connected to the rotator 146. A guidewire 149 is inserted into the hollow of the torque transmission shaft 148 and the hollow of the rotator 146 and further passes through the guidewire guiding hole 152 of the backing member 151 so as to advance through the tip portion of the cap 147 into the blood vessel. Similarly, the guidewire 149 is freely movable without being obstructed by the catheter 142. This arrangement can offer an effect similar to that of the above-described embodiments.

In operation, when the catheter 142 reaches a target diseased part within the blood vessel, the torque transmission shaft 148 is rotationally driven by means of a drive section positioned at the rear end side of the catheter 142. This rotational driving force rotates the rotating shaft 145, rotator 146 and ultrasonic transducer 141 through the torque transmission shaft 148. In this state, an ultrasonic wave transmission signal is supplied through an unshown signal line to the ultrasonic transducer 141 whereby the ultrasonic transducer 141 radially scans the blood vessel with the ultrasonic wave. The ultrasonic wave reflected from the blood vessel is received by the ultrasonic transducer 141 so as to be converted into an electric signal which is in turn used for obtain an ultrasonic image.

Figure 9A:
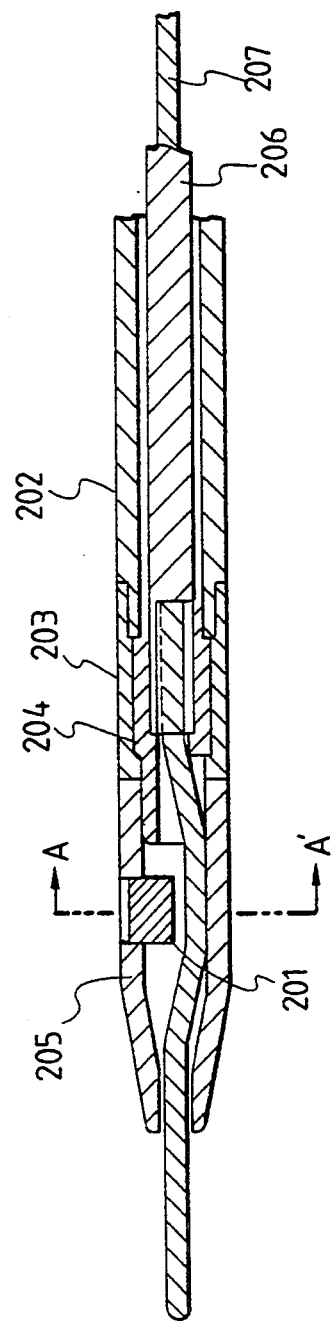
FIG. 9A is a side cross-sectional view showing an arrangement of an ultrasonic probe according to a seventh embodiment of this invention.
Figure 9B:
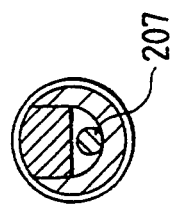
FIG. 9B is a cross-sectional view taken along a line A-A' in FIG. 9A.

In addition, a description will be made hereinbelow in terms of a seventh embodiment of this invention. FIG. 9A shows an arrangement of an ultrasonic probe according to the seventh embodiment of this invention, and FIG. 9B is a cross-sectional view taken along a line A–A' in FIG. 9A. In FIGS. 9A and 9B, a bearing 203 having a hollow structure is inserted and fixed to the tip portion of a catheter 202 having a hollow structure. A rotating shaft 204 is inserted into the bearing 203 so as to be freely rotatable with respect to the bearing 203. The tip portion of the rotating shaft 294 extends beyond the bearing 203. A transducer holder 205 is inserted into the tip portion of the rotating shaft 204 so that the bearing 204 is interposed between the rotating shaft 204 and the transducer holder 205 whereby the transducer holder 205 is rotatable together with the rotating shaft 204 without being disconnected from the bearing 203. An ultrasonic transducer 201 is fixedly secured to the transducer holder 205 and connected to a signal line, not shown. A torque transmission shaft 206 having a hollow structure passes through the catheter 202 and is fixed to the rotating shaft 204 inserted into the hollow of the bearing 203. A guidewire 207 extends in the hollow of the torque transmission shaft 206 to reach the tip portion of the rotating shaft 204 and then go out of the ultrasonic probe from the tip portion of the transducer holder 205 using the space within the transducer holder 205. This guidewire 207 is freely movable because of being not fixed. The transducer holder 205 is tapered so as to make easy the insertion of the catheter 202 into a blood vessel and prevent the blood vessel from being damaged irrespective of the movement of the catheter 202 within the narrow blood vessel.

FIG. 10 is a block diagram showing an arrangement of an ultrasonic diagnostic apparatus including the FIGS. 9A and 9B ultrasonic probe. In FIG. 10, numeral 220 represents the ultrasonic probe illustrated in FIGS. 9A and 9B, 221 designates a drive section coupled to the catheter 202 and the torque transmission shaft 206, 222 is a motor, 223 depicts a position detector connected to the motor 222, 224 denotes a transmission section coupled to the ultrasonic transducer 201, 225 indicates a reception section, 226 is a detector section, 227 represents a scan conversion section, and 228 is an display section.

In operation, when the catheter 202 reaches a target diseased part and the guidewire 207 is returned up to the inside of the rotating shaft 207, the motor 222 of the drive section 221 positioned at the rear end portion of the catheter 202 is driven so as to rotate the torque transmission shaft 206. This rotational driving force rotates the rotating shaft 204 and the transducer holder 205. Due to the rotation of the transducer holder 205, the ultrasonic transducer 201 is rotated in the radial direction. In this state, an ultrasonic wave transmission signal is supplied from the transmission section 224 through the signal line to the ultrasonic transducer 201. In response to the ultrasonic wave transmission signal, the ultrasonic transducer 201 generates an ultrasonic wave and receives the ultrasonic wave reflected from the blood vessel to convert it into an electric signal, i.e., a reflection signal. This reflection signal is supplied to the reception section 225 so as to be amplified, and then supplied to the detector section 226 to be detected. The detected signal is converted into a standard television signal in the scan conversion section 227 so that a two-dimensional ultrasonic image is display on the display section 228. The rotational position signal necessary for displaying the two-dimensional ultrasonic image is obtained from the rotational position detector such as an encoder 223 connected to the motor 222 and inputted to the scan conversion section 227. The unshown signal line extending from the ultrasonic transducer 201 is disposed to pass through the transducer holder 205 and run between the torque transmission shaft 206 and the guidewire 207 or along the outside of the torque transmission shaft 206 and finally reach the transmission section 224 and the reception section 225.

Figure 11:
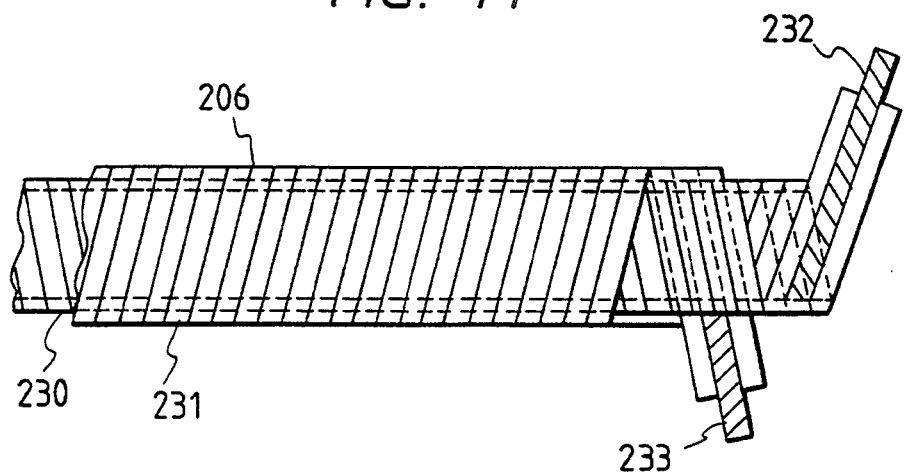
FIG. 11 shows an arrangement of a torque transmission shaft of an ultrasonic probe according to an eighth embodiment of this invention.

A description will be made hereinbelow in terms of an eighth embodiment of this invention. FIG. 11 shows a different arrangement of the torque transmission shaft 206 of an ultrasonic probe according to the eighth embodiment of this invention. In FIG. 11, for constructing the torque transmission shaft 206, a first spring-like layer 230 is constructed with a plurality of wires (3 wires in the illustration) arranged in parallel to each other and a second spring-like layer 231 having the same structure as the first spring-like layer 230 is then constructed on the first spring-like layer 230 so as to cover the first spring-like layer 230, thereby obtain a 3-wire and 2-layer structure. Numeral 232 represents a first signal line which is one of the 3 wires, constituting the first spring-like layer, which wire is made of an electric conductive material and covered (coated) by an insulating material and numeral 233 represents a second signal line which is one of the 3 wires, constituting the second spring-like layer, which wire is made of an electric conductive material and covered (coated) by an insulating material. These first and second signal lines 232 and 233 are used as the signal lines for connection between the ultrasonic transducer 201 and the transmission section 224, the reception section 225. Unlike the above-described embodiments, this arrangement does not require that the signal line is disposed so as to run in the torque transmission shaft 206 or advance along the outside of the torque transmission shaft 206, thereby allows the reduction of the diameter of the catheter 202.

Figure 12:
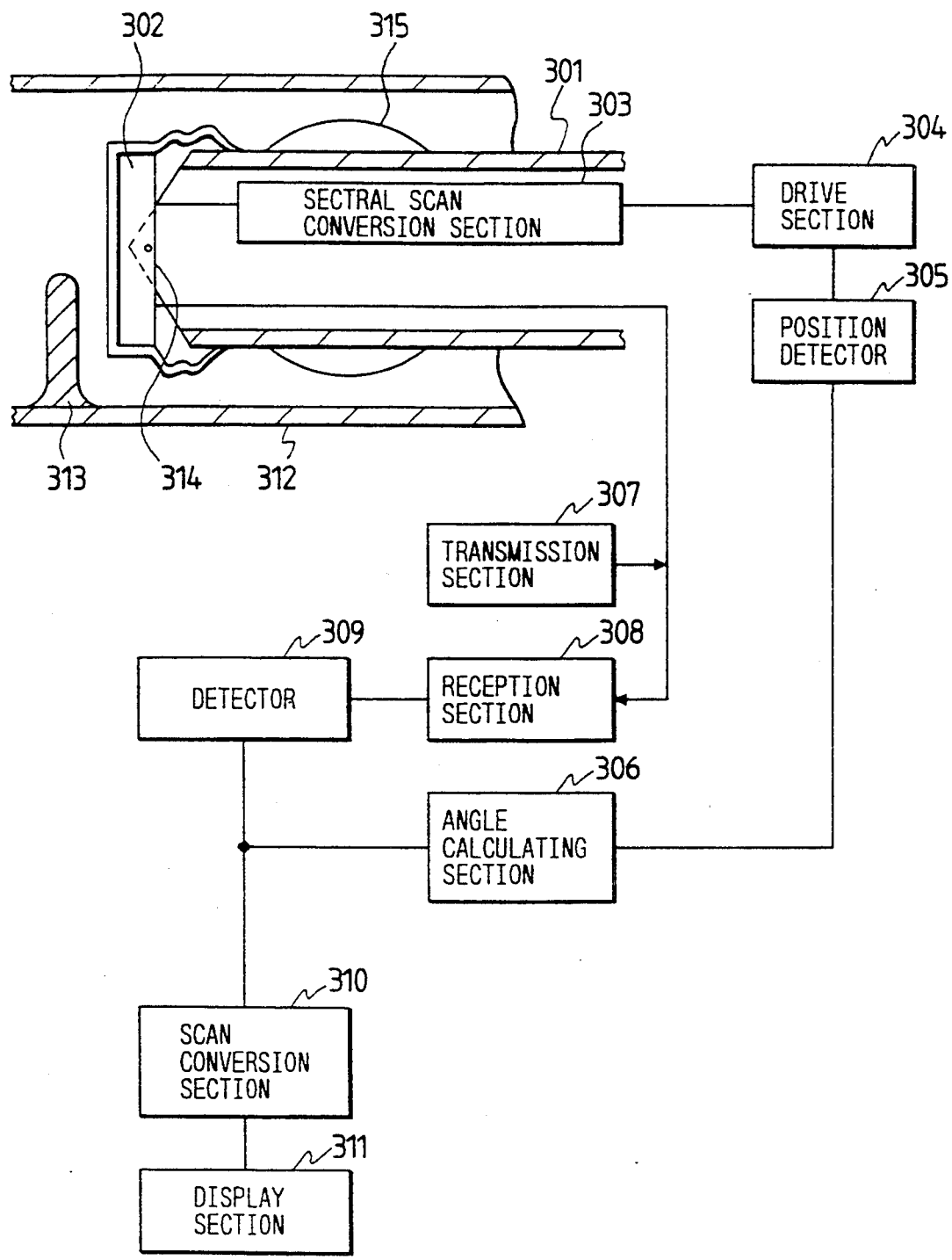
FIG. 12 is a block diagram showing an arrangement of an ultrasonic probe according to a ninth embodiment of this invention.

Moreover, a description will be made hereinbelow in terms of a ninth embodiment of this invention. FIG. 12 is a block diagram showing an arrangement of an ultrasonic probe according to the ninth embodiment of this invention. In FIG. 12, numeral 301 represents a catheter, 302 designates an ultrasonic transducer comprising a ferroelectric polymer film having a poling portion and a non-poling portion, 303 depicts a sectral scan conversion mechanism (corresponding to that in the second embodiment) for driving the ultrasonic transducer 302 in response to a driving force from a drive section 304 so that the ultrasonic transducer 302 performs a sectral scan operation, 305 is a position detecting section, 306 represents an angle calculating section coupled to the position detecting section 305, 307 depicts a transmission section coupled to the ultrasonic transducer 302, 308 denotes a reception section coupled to the ultrasonic transducer 302, 309 is a detector section coupled to the reception section 308, 310 indicates a scan conversion section coupled to the angle calculating section 306 and the detector section 309, 311 represents a display section coupled to the scan conversion section 310, 312 indicates a blood vessel, 313 is an atheroma, 314 represents a bearing for the ultrasonic transducer 302, and 315 denotes an atheroma treating balloon.

Figure 13:
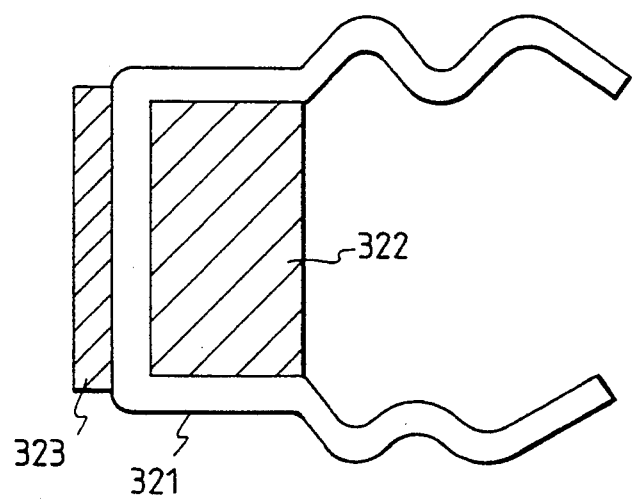
FIG. 13 shows an arrangement of an ultrasonic transducer in FIG. 12 ultrasonic probe.

Operation will be described with reference to FIGS. 12 and 13. FIG. 13 shows an arrangement of the ultrasonic transducer in the FIG. 12 ultrasonic probe. In FIGS. 12 and 13, the catheter 301 is inserted into the blood vessel 312 so that the tip portion of the catheter is moved up to the vicinity of the atheroma 313. When the tip portion of the catheter 301 reaches the vicinity of the atheroma 313, the transmission section 307 supplies an ultrasonic wave transmission signal to the ultrasonic transducer 302 which in turn transmits an ultrasonic wave toward the front side of the catheter 302. The ultrasonic wave transmitted from the ultrasonic transducer 302 propagates in the blood to reach the atheroma 313. A portion of the ultrasonic wave transmitted reflects on the atheroma 313 and a portion of the ultrasonic wave penetrates the atheroma 313. The ultrasonic wave penetrating the atheroma 313 is successively reflected due to the difference between the acoustic impedances and then returned to the ultrasonic transducer 302. The ultrasonic wave reflected and returned to the ultrasonic transducer 302 is converted into an electric signal and then amplified in the reception section 308 and further detected in the detector section 309.

The sectral scan conversion mechanism 303 is responsive to a drive force from the drive section 304 such as a motor to perform a swinging operation whereby the ultrasonic transducer 302 swingingly moves to sectrally scan. That is, the ultrasonic beam from the ultrasonic transducer 302 is swung within a sectral configuration.

As illustrated in FIG. 13, the ultrasonic transducer 302 comprises a high-polymer piezoelectric film 321, a backing member 322 and an acoustic matching layer 323. The high-polymer piezoelectric film 321 is a ferroelectric film and partially poling-processed. On the back surface of the ultrasonic-wave emitting portion of the high-polymer piezoelectric film 321 there is provided the backing member 322 having a flat configuration, and on the front surface thereof there is provided the acoustic matching layer 323 for preventing the reflection due to the difference between the acoustic characteristics of the high-polymer piezoelectric film 321 and the medium in which the ultrasonic wave propagates. A non-poling-processed portion of the high-polymer piezoelectric film (piezoelectric polymer film) 321 is bent toward the backing member 322 side so that the high-polymer piezoelectric film 321 has a cap-like configuration. The bent portion of the high-polymer piezoelectric film 321 is arranged to have a bellows configuration so as to be expandable and contractible when the ultrasonic transducer 301 swings to sectrally scan.

The direction information of the ultrasonic transducer 302 can be obtained with the position detecting section 305 such as an encoder being coupled to the drive section 304. The angle calculating section 306 calculates the beam illumination (emitting) direction of the ultrasonic transducer 302 on the basis of the output signal of the position detecting section 305. The scan conversion section 10 produces the standard television signal on the basis of the output of the angle calculating section 306, which is the beam direction information of the ultrasonic transducer 302, and the output of the detector section 309, which is the signal obtained by detecting the reflection signal. The display section 311 displays a two-dimensional ultrasonic image on the basis of the output of the scan conversion section 10, thereby perform the ultrasonic diagnosis. In accordance with the ultrasonic diagnosis result, the catheter 301 is moved so that the balloon 315 is positioned at the atheroma 313 to treat the atheroma 315.

According to this embodiment, it is possible to surely diagnose the blood vessel without injecting a normal saline solution into the blood vessel, and it is possible to provide an ultrasonic probe which is capable of being simply manufactured.

Although in this embodiment the backing member 322 is arranged to have a flat configuration, it is appropriate that the backing member 322 is arranged to have a concave configuration to focus the ultrasonic wave. Further, it is also appropriate that an acoustic lens is provided on the front surface of the acoustic matching layer 323 so as to focus the ultrasonic wave.

Figure 14:
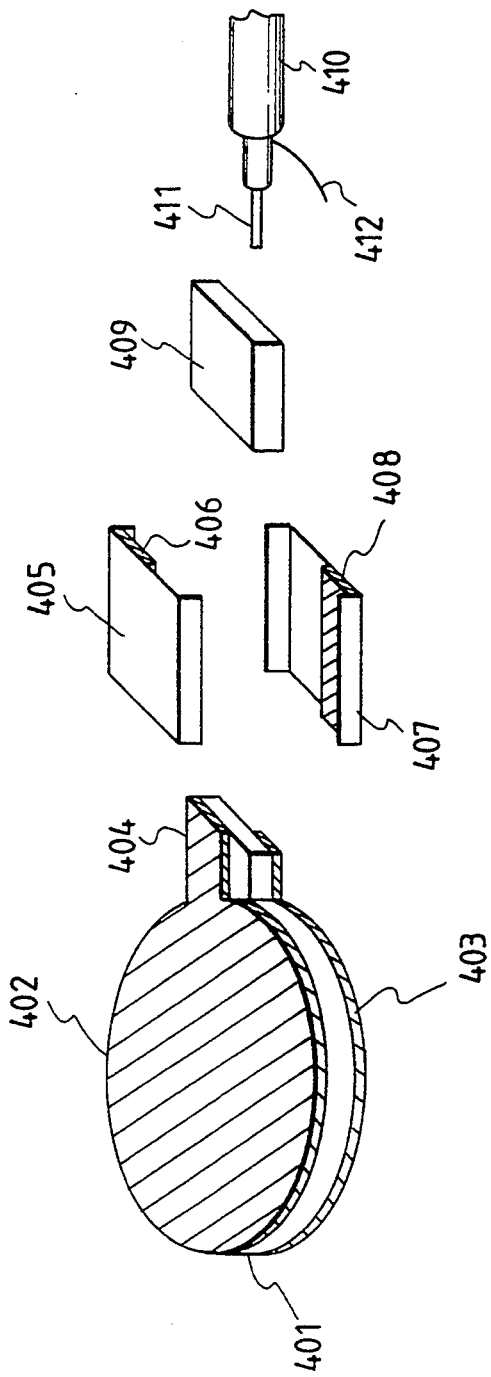
FIG. 14 is an exploded and perspective view showing an ultrasonic probe according to a tenth embodiment of this invention.
Figure 15:
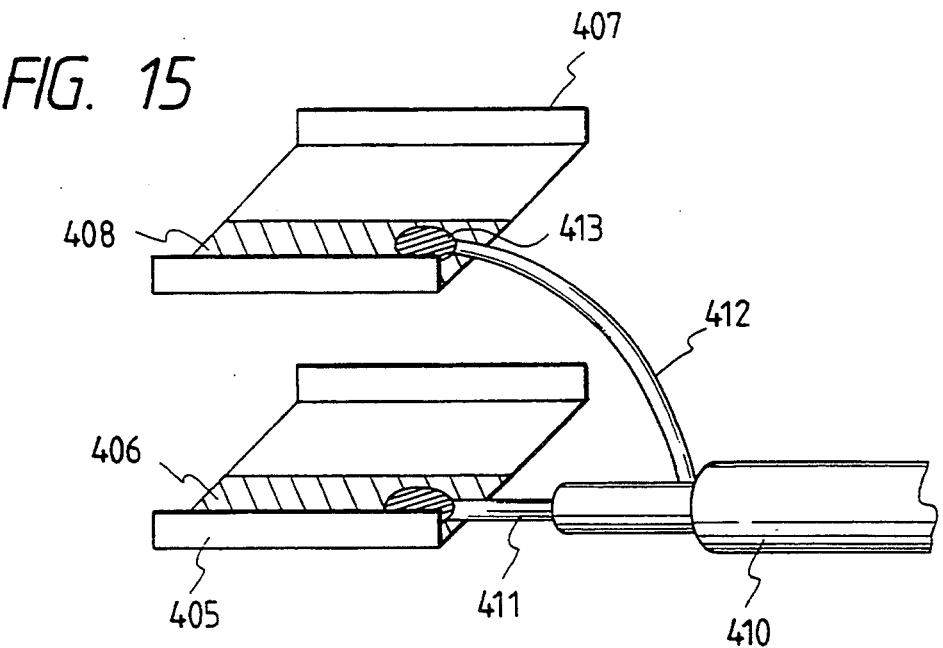
FIG. 15 is a perspective view showing a portion of the FIG. 14 ultrasonic probe.
Figure 16:
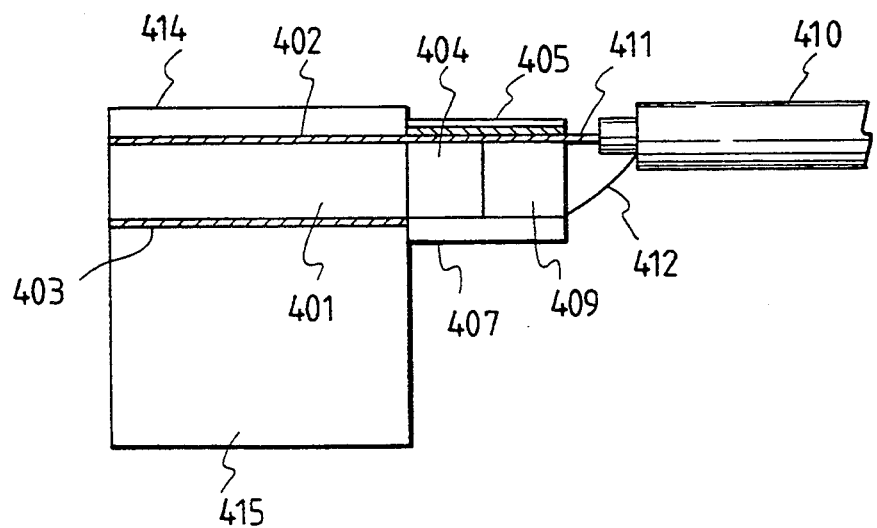
FIG. 16 is a cross-sectional view showing an ultrasonic transducer of the FIG. 14 ultrasonic probe.

A description will be described in terms of an ultrasonic probe according to a tenth embodiment of this invention. FIG. 14 is an exploded and perspective view showing an ultrasonic probe according to the tenth embodiment of this invention, FIG. 15 is a perspective view showing a portion of the FIG. 14 ultrasonic probe, and FIG. 16 is a cross-sectional view showing an ultrasonic transducer of the FIG. 14 ultrasonic probe. In FIG. 14, numeral 401 is a piezoelectric plate made, for example, from a piezoelectric ceramic and equipped with a projecting portion 404, 402 represents a radiation side electrode, 403 designates a back side electrode, 405 depicts a connecting member made of an insulating material, 406 denotes an electrode provided on the inner surface of the connecting member 405, and 407 indicates a connecting member made of an insulating material. Further, numeral 408 is an electrode provided on the inner surface of the connecting member 407, 409 represents an insulating member interposed between the connecting members 405 and 407, 410 designates a coaxial cable, 411 denotes an inner conductor of the coaxial cable 410, and 412 is an outer conductor of the coaxial cable 410.

Further, the arrangement of the ultrasonic probe according to the tenth embodiment of this invention will be described hereinbelow with reference to FIGS. 14 to 16. In FIGS. 14 to 16, on both the entire surfaces of the circular piezoelectric plate 401 having the projecting portion 404 there are provided the radiation side electrode 402 and the back side electrode 403. However, on both surfaces of the projecting portion 404, the electrodes are arranged so as not to be placed at positions which are in opposed relation to each other, thereby preventing the projecting portion 404 from vibrating when an electric field is applied to the piezoelectric plate 401. On the front surface of the radiation side electrode 402 there is provided an acoustic matching layer 414 for the acoustic matching. Further, on the front surface of the back side electrode 403 there is provided a backing member 415 for allowing a sufficient attenuation of the ultrasonic wave. Here, the acoustic matching layer 414 and the backing member 415 are not provided on the projecting portion 404.

On the inner surface of the connecting member 505 there is provided the electrode 406 which is arranged to come into contact with the radiation side electrode 402 on the projecting portion 404. Further, on the inner surface of the connecting member 407 there is disposed the electrode 408 which is arranged to come into contact with the back side electrode 403 on the projecting portion 404. The electrodes 406 and 408 are arranged so as not to be placed at positions, which are in opposed relation to each other, when the connecting members 405 and 407 face each other. The inner conductor 411 is adhered through a bonding material such as a conductive adhesive to the electrode 406 and the outer conductor 412 is adhered through a conductive adhesive 413 to the electrode 408.

The insulating member 409 having a thickness substantially equal to the thickness of the piezoelectric plate 401 is disposed on the extension of the projecting portion 404. The projecting portion 404 and the insulating member 409 are interposed between the connecting member 405 connected to the inner conductor 411 and the connecting member 407 connected to the outer conductor 412 whereby the inner conductor 411 is connected to the radiation side electrode 402 and the outer conductor 412 is connected to the back side electrode 403. In addition, the inner and outer conductors 411 and 412 are surely insulated electrically by the insulating member 409.

According to this embodiment, it is possible to simply couple the ultrasonic transducer to the signal line.

Further, a description will be made with reference to FIG. 14 in terms of a method of manufacturing the ultrasonic transducer according to the tenth embodiment of this invention. For manufacturing the piezoelectric plate 401 having the projecting portion 404, for example, gold is deposited on both the entire surfaces of a piezoelectric base having a dimension larger than that of the piezoelectric plate 401 and a mask is used so as to obtain a configuration corresponding to the piezoelectric plate 401 having the projecting portion 404. Further, for example, the etching is performed so as to unnecessary electrode portions, and the unnecessary portion of the piezoelectric base are removed so as to obtain the piezoelectric plate 401. Thereafter, the inner conductor 411 of the coaxial cable 410 is adhered through a conductive adhesive to the electrode 406 provided on the connecting member 405 and the outer conductor thereof is adhered through a conductive adhesive to the electrode 408 of the connecting member 407, and the connecting members 405 and 407 are coupled under a pressure or adhered to each other so as to make spaces for insertions of the projecting portion 404 and the insulating member 409. Finally, the projecting portion 404 and the insulating member 409 are inserted into the connecting member assembly from opposite directions and fixedly adhered thereto by an adhesive or the like. According to this method, it is possible to easily manufacture the ultrasonic probe.

Figure 17A:
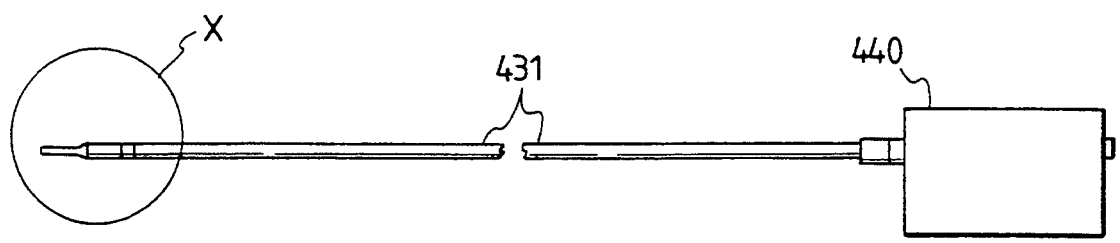
FIG. 17A shows an ultrasonic probe according to the eleventh embodiment of this invention.
Figure 17B:
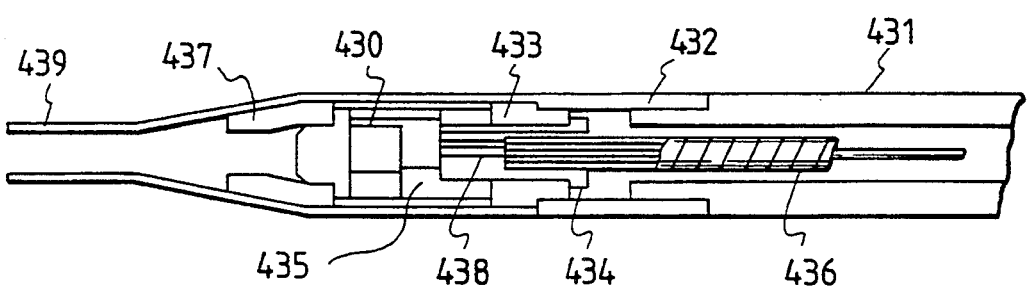
FIG. 17B is an enlarged and cross-sectional view showing a portion of the FIG. 17A ultrasonic probe.

Moreover, a description will be described hereinbelow in terms of an eleventh embodiment of this invention. FIG. 17A shows an ultrasonic probe according to the eleventh embodiment of this invention and FIG. 17B is an enlarged and cross-sectional view showing a portion of the FIG. 17A ultrasonic probe which is indicated by a circle X in FIG. 17A. In FIG. 17A and 17B, numeral 430 is an ultrasonic transducer, 431 represents a catheter, 432 designates a joint at its one end portion connected to the tip portion of the catheter 431, 433 depicts a bearing connected to the other end portion of the joint 432, 434 depicts a rotating shaft inserted into the bearing 433 to be rotatable, and 435 indicates a transducer holder, together with the rotating shaft 434, inserted into the bearing 433. The ultrasonic transducer 430 is fixedly inserted into a cylindrical transducer insertion hole formed in the transducer holder 435. Further, 436 represents a torque transmission shaft fixedly inserted into the transducer holder 435, 437 is a cap provided at the tip portion of the transducer holder 435, 438 denotes a signal line for coupling the ultrasonic transducer 430 to a main body, not shown, 439 indicates an acoustic window which covers the bearing 433 and the cap 437, and 440 represents a drive section.

More specifically, the joint 432 having a hollow structure and made of a hard material is at its one end portion connected fixedly to the tip portion of the catheter 431 having a hollow structure. The bearing 433 is fixedly inserted into the other end portion of the joint 432 so that the catheter 431 and the bearing 433 are coupled to each other through the joint 432. Here, before the connection between the bearing 433 and the joint 432, the rotating shaft 434 is inserted into the inside of the bearing 433 from the direction of drive section 440. The rotating shaft 434 is freely rotatable with respect to the bearing 433, and the tip portion of the rotating shaft 434 protrudes from the bearing 433 and is fixed to the transducer holder 435. That is, the bearing 433 is interposed between the rotating shaft 434 and the transducer holder 435 whereby the transducer holder 435, together with the rotating shaft 434, is rotatable without being disconnected from the bearing 433.

The torque transmission shaft 436 passes through the inside of the catheter 431 and passes through the hollows of the joint 432 and the bearing 433 so as to be fixedly inserted into the insertion hole of the rotating shaft 434. The signal line 438 passes through the inside of the torque transmission shaft 436 and is inserted through the hollow of the rotating shaft 434 into the inside of the transducer holder 435 and outputted to the outside of the transducer holder 435 to be connected to an electrode of the ultrasonic transducer 430. The tip portion of the transducer holder 435 is inserted into the inside of the cap 437, thereby preventing the transducer holder 435 from being deflected during the rotation. Further, the cap 437 is configured to be made narrower toward its tip portion so as to make easy the insertion into the blood vessel. This cap 437, together with the bearing 433, is covered by the acoustic window 439 which is made of a material having a heat contraction characteristic whereby it is possible to adequately coal the cap 437 tapered. This acoustic window 439 prevents the bearing 433 and others from damaging the inner wall of the blood vessel irrespective of the movement of the catheter 431 within the blood vessel.

Figure 18:
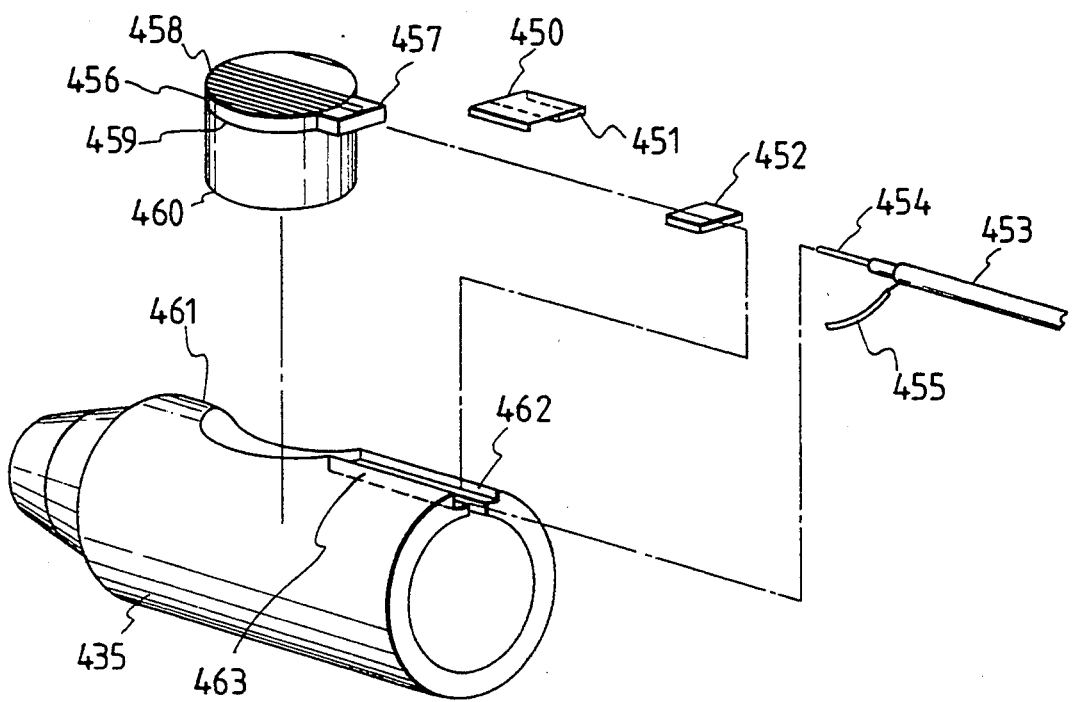
FIG. 18 is an enlarged illustration for describing the connection between a transducer holder and a signal line in the ultrasonic probe according to the eleventh embodiment of this invention.

FIG. 18 is an illustration for describing the connection between the transducer holder 435 and the signal line 438 in the ultrasonic probe according to this embodiment. In FIG. 18, numeral 450 represents a connecting member, 451 designates an electrode provided on the connecting member 450, 452 depicts an insulating member, 453 is a coaxial cable corresponding to the signal line 438 in FIG. 17B, 454 denotes an inner conductor constituting the coaxial cable 453, and 455 is an outer conductor constituting the coaxial cable 453. Further, numeral 456 is a piezoelectric plate, 457 represents a projecting portion formed at a side surface of the piezoelectric plate 456, 458 designates a radiation side electrode provided on the piezoelectric plate 456, and 459 denotes a back side electrode provided on the opposite side of the radiation side electrode 458. As well as the above-described tenth embodiment, on the projecting portion 457, the radiation side electrode 458 and the back side electrode 459 are arranged so as not to be placed at position which are in opposed relation to each other. Further, numeral 460 represents a back load member provided on the back side electrode 459, 461 represents a transducer insertion hole formed in the transducer holder 435, 462 designates a groove formed in the transducer holder 435, and 463 is an electrode provided in the groove 462. On the radiation side electrode 458 there is provided an acoustic matching layer, not shown.

The outer conductor 455 of the coaxial cable 453 which passes through the inside of the transducer holder 435 is connected to the electrode 463 provided in the groove 462, and the inner conductor 54 is connected to the electrode 451 provided on the connecting member 450. The piezoelectric plate 456, together with the back load member 460 and the acoustic matching layer, is fixedly inserted into the transducer insertion hole 461 of the transducer holder 435 so that the projecting portion 457 is engaged with the groove 462. Further, the insulating member 452 is disposed on time extension of the projecting portion 457, and the connecting member 450 connected to the inner conductor 454 is fixed in the groove 462. The transducer holder 435 is made of an insulating material such as a resin in order to prevent the electric short between the inner conductor 454 and the outer conductor 455.

In operation, when the catheter 431 is positioned at the vicinity of a target diseased part within the blood vessel, the drive section 440 rotates the torque transmission shaft 436 so as to rotate the rotating shaft 434 and the transducer holder 435. Due to the rotation of the transducer holder 435, the ultrasonic transducer 430 is rotated in the radial direction. In response to an ultrasonic wave transmission signal, the ultrasonic transducer 430 transmits an ultrasonic wave which in turn passes through the acoustic window 439 to advance into the blood vessel. The ultrasonic transducer 430 receives the reflected ultrasonic wave from the blood vessel to convert it into an electric signal (reflection signal) in order to obtain a two-dimensional ultrasonic image.

Here, the space between the transducer holder 435 and the acoustic window 439 is filled with a liquid such as a normal saline solution which can effectively propagate the ultrasonic wave and which does not impair the human body. It is also appropriate that the blood is injected from the top portion thereinto. The inner diameter of the catheter 431 becomes about $\phi 1$ mm.

According to this embodiment, since the connection between the ultrasonic transducer 430 and the signal line 438 is effected by means of the electrode 451 on the connecting member 450 fitted in the groove 462 and the electrode 463 in the groove 462 of the transducer holder 435, it is possible to easily derive the signal line 438 without reducing the necessary transducer area in the catheter 431 having the inner diameter of φ1 mm.

Although in the above-described tenth embodiment the piezoelectric plate is arranged to have a circular configuration and have the projecting portion, the configuration of the piezoelectric plate is not limited to the circular configuration. Further, although in the tenth embodiment the electrode is adhered through the adhesive to the coaxial cable, it is also appropriate that the inner and outer conductors are coupled so as to be fixedly contact with the corresponding electrodes without using the adhesive.

Figure 19:
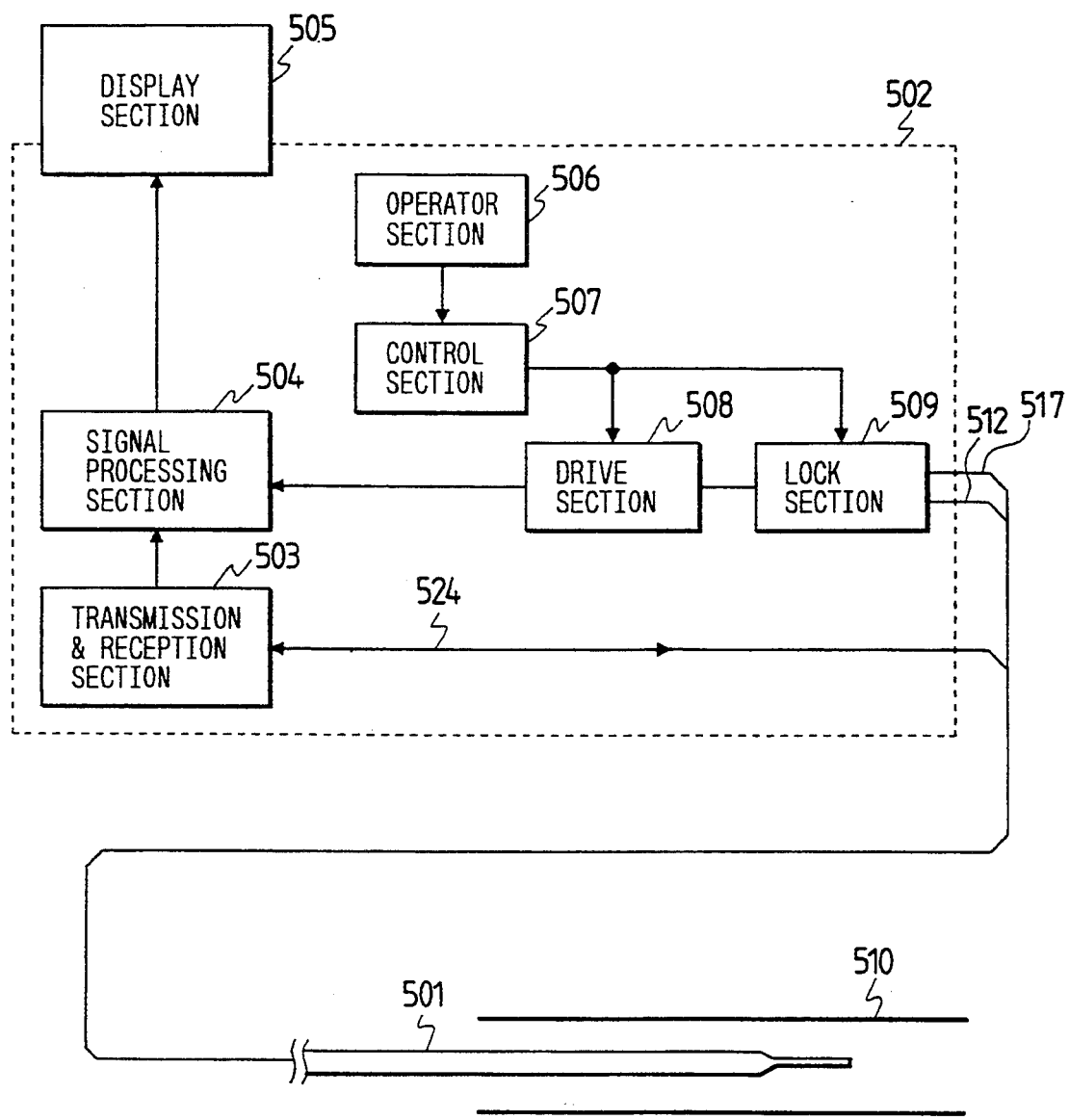
FIG. 19 is a block diagram showing an arrangement of an ultrasonic diagnostic apparatus according to a twelfth embodiment of this invention.

Further, a description will be described hereinbelow in terms of a twelfth embodiment of this invention. This embodiment is for eliminating a problem of conventional ones that the distance between an ultrasonic transducer and a reflection mirror is not changeable so as to deteriorate the resolution of the ultrasonic image. FIG. 19 is a block diagram showing an arrangement of an ultrasonic diagnostic apparatus according to the twelfth embodiment of this invention. In FIG. 19, numeral 501 represents an ultrasonic probe and 502 designates a main body. The main body 502 comprises a transmission and reception section coupled through a coaxial cable 524 to the ultrasonic probe 501, a signal processing section 504 coupled to the transmission and reception section 503, a display section 505 connected to the signal processing section 504 and including a television monitor for displaying an ultrasonic image, an operator section 506, a control section 507, a drive section 508 comprising a motor and an encoder, and a lock section 509. To the lock section 509 there is connected a first torque transmission shaft 514 and a second torque transmission shaft 521. Numeral 510 represents an object to be examined.

Figure 20:
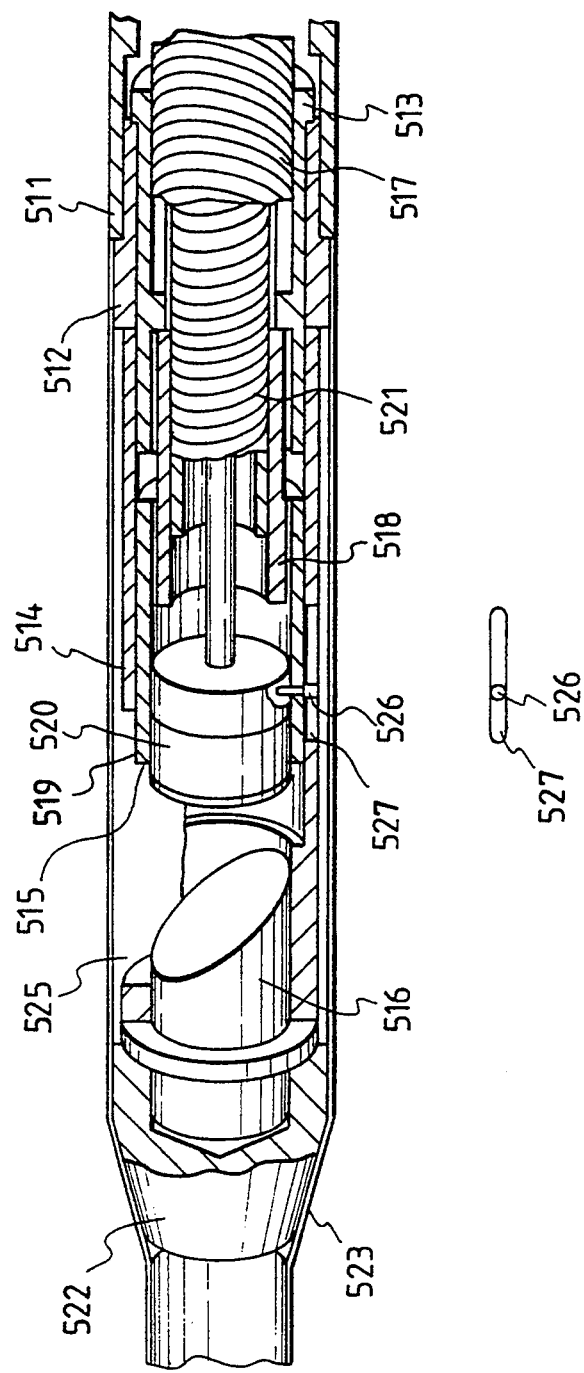
FIG. 20 shows a detailed arrangement of an ultrasonic probe of the FIG. 19 ultrasonic diagnostic apparatus.

FIG. 20 shows a detailed arrangement of the ultrasonic probe 501. In FIG. 20, numeral 511 represents a catheter, 512 designates a bearing having a hollow structure and fixedly at its one end portion connected to the tip portion of the catheter 511, 513 depicts a rotating shaft having a hollow structure and inserted into the inside of the bearing 512 from the rear side and having a length longer than that of the bearing 512, and 514 denotes a mirror holder having a hollow structure and fixedly inserted into the tip portion of the rotating shaft 513 protruding from the bearing 512 after the rotating shaft 513 is inserted into the bearing 512. The mirror holder 514 is equipped with an ultrasonic wave opening 515 in the vicinity of the tip portion (an ultrasonic wave emitting portion). Further, 516 represents a reflection mirror for propagating an ultrasonic wave into the object 510. The reflection surface of the reflection mirror 516 is inclined by 45o with respect to the central axis of the ultrasonic probe 501. The first torque transmission shaft 517 has a flexible hollow spring structure and the tip portion of the first torque transmission shaft 517 is fixedly inserted into the read end portion of the rotating shaft 513 and the rear end portion of the first torque transmission shaft 517 is connected to the lock section 509. The first torque transmission shaft 517 is for transferring a rotational force due to the drive section 508 through the lock section 509 to the ultrasonic probe 501. Due to the rotation of the first torque transmission shaft 512, the rotating shaft 513, mirror holder and reflection mirror are rotated with respect to the bearing 512. Moreover, numeral 518 is a joint having a hollow structure. The rear end portion of the joint 518 is inserted into the hollow of the tip portion of the rotating shaft 513. A thread (screw) portion is formed on the outer wall of the tip portion of the joint 518. The joint 518 is rotatable with respect to the rotating shaft 513. Here, the rotating shaft 513 is arranged such that its inner wall portion has a two-step structure to thereby limit the insertion of the joint 518 into the rotating shaft 513 up to a predetermined length. Illustrated at numeral 519 is a transducer holder having a hollow structure. On the inner wall portion of the transducer holder 519 there is formed a thread portion which is engageable with the thread portion of the joint 518. The outer diameter of the transducer holder 519 is arranged smaller than the inner diameter of the mirror holder 514 so that the transducer holder 519 is movable with respect to the mirror holder 514. Further, designated at numeral 520 is an ultrasonic transducer for transmission and reception of an ultrasonic wave. The ultrasonic transducer 520 is fixed to the tip portion of the transducer holder 519. Illustrated at numeral 521 is a second torque transmission shaft which has a hollow spring structure and which is inserted into the hollow of the first torque transmission shaft 517 so as to be independently rotatable. The tip portion of the second torque transmission shaft 521 is fixedly inserted into the rear end portion of the joint 518 and the rear end portion of the second torque transmission shaft 521 is connected to the lock section 509. Further, numeral 522 represents a bearing positioned at the tip portion of the reflection mirror 516, 523 designates a cap arranged to entirely cover the tip portion of the ultrasonic probe 501. The cap 523 is fixed to the catheter 511 and the bearing 522. In addition, numeral 524 is a coaxial cable inserted into the inside of the second torque transmission shaft 521. The tip portion of the coaxial cable 524 is connected to an electrode of the ultrasonic transducer 520, and the rear end portion of the coaxial cable 524 is connected to the transmission and reception section 503. Numeral 525 is an ultrasonic wave propagation medium provided within the cap 523.

Further, the ultrasonic probe 501 comprises a pin 526 provided in the transducer holder 519, a groove 527 formed in the mirror holder 514 and engaged with the pin 526. The groove 527 is formed to be parallel to the central axis of the ultrasonic probe 501 and has a length corresponding to the moving distance of the transducer holder 519 along the central axis thereof. Due to the pin 526 and the groove 527, the rotating direction of the transducer holder 519 is limited with respect to the mirror holder 514.

In operation, an ultrasonic wave transmission signal generated in the transmission and reception section 503 is supplied through the coaxial cable 524 to the ultrasonic transducer 520. In response to the ultrasonic wave transmission signal, the ultrasonic transducer 520 emits an ultrasonic wave into the ultrasonic wave propagation medium 525. The propagation direction of the ultrasonic wave is changed by 90° by the reflection mirror 516 so that the ultrasonic wave directs in a direction perpendicular to the central axis of the ultrasonic probe 501 so as to be emitted into the object 510 and then reflected in correspondence with the variation of the acoustic characteristic to be returned through the same passage to the ultrasonic transducer 520. The reflected ultrasonic wave is converted into an electric signal and supplied to the transmission and reception section 503.

The ultrasonic image due to the radial scanning can be obtained by the rotation of the reflection mirror 516. The first and second torque transmission shafts 517 and 521 are rotated at the same speed and in the same direction. This can be achieved with the rotating force due to the motor of the drive section 508 being transferred through the lock section 509 to the first and second torque transmission shafts 517 and 521. The lock section 509 is for simultaneously transferring the rotating force due to the drive section 508 to the first and second torque transmission shafts 517 and 521 and further for releasing the simultaneous rotating state in accordance with a control signal from the control section 507 to fix the rotation of the first torque transmission shaft 517 and transfer the rotating force to only the second torque transmission shaft 521.

Due to the rotation of the first torque transmission shaft 517, the rotating shaft 513 fixedly connected to the first torque transmission shaft 517 and the mirror holder 514 fixedly connected to the rotating shaft 513 are rotated with respect to the bearing 512 so that the reflection mirror 516 fixed to the tip portion of the mirror holder 514 is rotated so as to allow the radial scanning for the object 510. In addition, due to the groove 527 formed in the mirror holder 514 and the pin 526 provided on the transducer holder 519, the transducer holder 519 is rotated at the same speed and in the same direction as the mirror holder 514. Here, although the joint 519 connected through the thread to the rear end portion of the transducer holder 519 is rotated by the second torque transmission shaft 521, since the rotating operation of the second torque transmission shaft 521 is the same as the rotating operation of the first torque transmission shaft 517 due to the function of the lock section 509, the rotating operation of the transducer holder 519 becomes the same as the rotating operation of the joint 508 whereby finally the reflection mirror 516 and the ultrasonic transducer 520 can be rotated without changing the positional relation between the reflection mirror 516 and the ultrasonic transducer 520. In addition, the radial scanning is allowed with the ultrasonic wave emitting state of the ultrasonic transducer 520 being constant with respect to the reflection mirror 514. The signal processing section 504 produces an image matching a television synchronizing signal on the basis of the angle information, which is the output of the encoder of the drive section 508, and the output of the transmission and reception section 503, thereby displaying on the display section 505 an ultrasonic image not having distortion.

When the ultrasonic wave focusing area is shifted from the object area because of the dimension of the object 510 and the positional relation of the ultrasonic probe 501, the ultrasonic image displayed on the display section 505 has a low resolution. Accordingly, the operator inputs through the operator section 506 an instruction for adjusting the focusing area. For the changing the focusing area, the distance between the ultrasonic transducer 520 and the reflection mirror 516 is changed. In accordance with the instruction from the operator section 506, the control section 507 outputs control signals to the drive section 508 and the lock section 509. The control signal to be supplied to the lock section 509 is for releasing the simultaneous rotation of the first and second torque transmission shafts 517 and 521. The lock section 509 transmits the driving force due to the drive section 508 to only the second torque transmission shaft 521 and stops and fixes the rotation of the first torque transmission shaft 517. The drive section 508 rotates in the direction and for the time period determined by the control signal from the control section 507. The second torque transmission shaft 521 rotated by the drive section 508 and the lock section 509 rotates the joint 508. On the other hand, the transducer holder 519 is not rotatable with respect to the mirror holder 514 by means of the pin 526 and the groove 527 provided in the mirror holder 514. The mirror holder 514 is fixedly connected through the rotating shaft 513 to the first torque transmission shaft 517 and the first torque transmission shaft 517 is fixed so as not to be rotated by the lock section 509. Thus, the transducer holder 519 is not rotated.

Since the transducer holder 519 is not rotated, the rotating force of the joint 508 to be rotated by the second torque transmission shaft 521 rotates the threads provided on the outside of the joint 508 and the inside of the transducer holder 519, thereby finally moving the transducer holder 519 in the forward and backward directions. The moving distance corresponds to the time determined by the control signal from the control section 507 and the moving direction depends on the rotating direction.

As described above, according to this embodiment, with the first and second torque transmission shafts 517 and 521 being simultaneously rotated, the mirror holder 514 holding the reflection mirror 516 and the transducer holder 519 can simultaneously be rotated, thereby obtaining the ultrasonic image of the object 510 due to the radial scanning. In addition, since in accordance with the control signal from the control section 507 the lock section 509 transmits the driving force due to the drive section 508 to only the second torque transmission shaft 521 and stops the rotation of the first torque transmission shaft 517, the transducer holder 519 is movable in the forward and backward directions with respect to the mirror holder 514 whereby the distance between the ultrasonic transducer 520 and the reflection mirror 516 is changeable in the state that the ultrasonic probe 501 is kept in the object 510. Thus, it is possible to change the focusing area of the ultrasonic wave with respect to the object 510, thereby realizing an excellent ultrasonic diagnostic apparatus.

Figure 21:
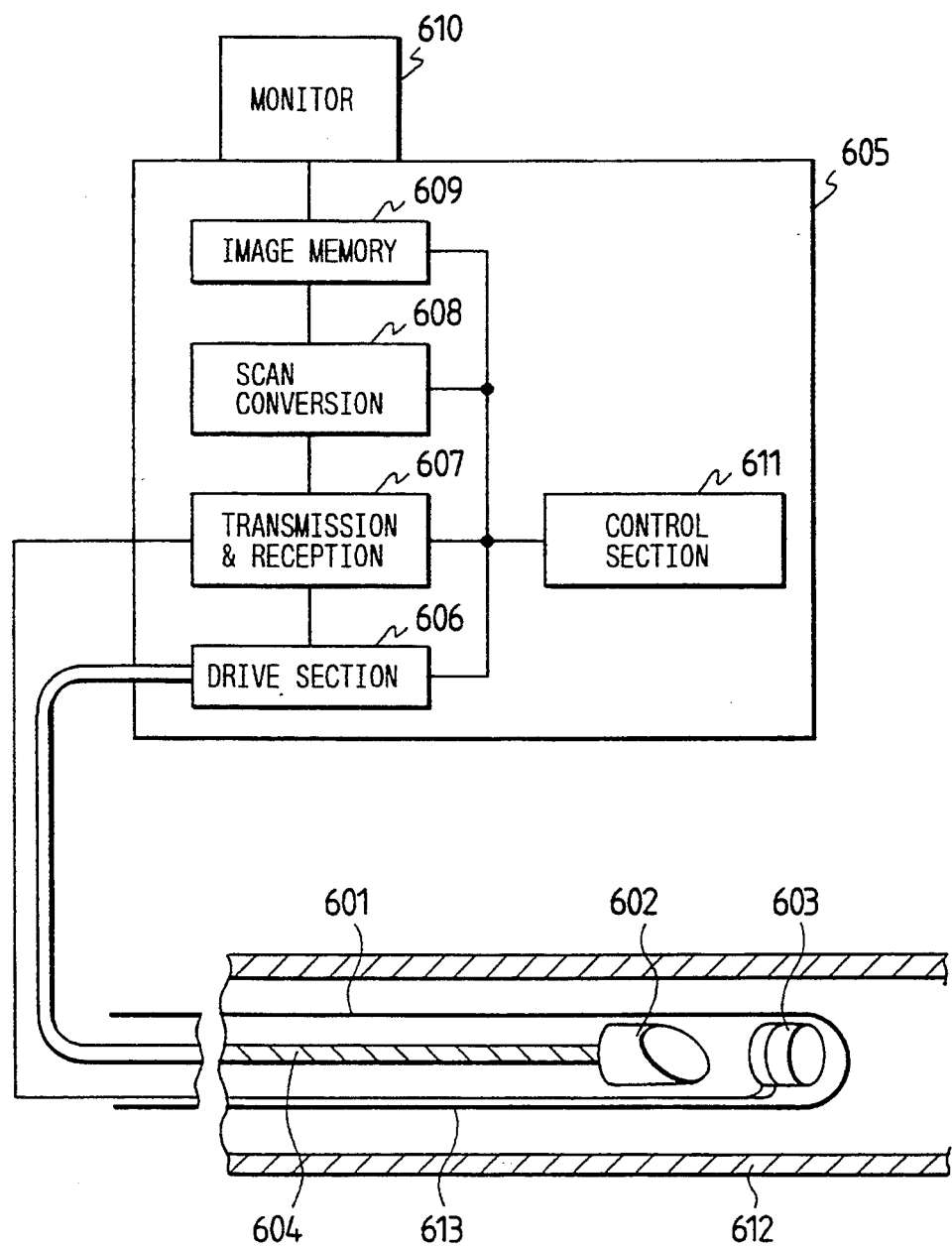
FIG. 21 is a block diagram showing an arrangement of an ultrasonic diagnostic apparatus according to a thirteenth embodiment of this invention.

Still further, a description will be described hereinbelow in terms of a thirteenth embodiment of this invention. FIG. 21 is a block diagram showing an arrangement of an ultrasonic diagnostic apparatus according to the thirteenth embodiment of this invention. In FIG. 21, numeral 601 represents a catheter, 602 designates a rotationally scanning portion such as a mirror, 603 depicts an ultrasonic transducer, 604 denotes a torque transmission shaft, and 605 is a main body. The main body 605 comprises a drive section 606 including a motor and encoder and coupled to the torque transmission shaft, a transmission and reception section 607 including an ultrasonic pulse transmission circuit, a reception amplifier, an A/D converter and others and coupled to the ultrasonic transducer 603, a scan conversion section 608 connected to the transmission and reception section 607, an image memory section 609 connected to the scan conversion section 608, a monitor 610 connected to the image memory section 609, and a control section 611. Further, numeral 612 is a blood vessel, and 613 represents a signal line for coupling the ultrasonic transducer 603 to the transmission and reception section 607.

In operation, when the catheter 601 reaches a target diseased part, the drive section generates a driving force so as to rotate the torque transmission shaft 604 to rotate the rotationally scanning portion 602 disposed at the tip portion of the catheter 601. In the state that the rotationally scanning portion 602 is rotating, the transmission and reception section 607 outputs a transmission signal to the ultrasonic transducer 603 so as to generate an ultrasonic wave. The propagating direction of the ultrasonic wave generated by the ultrasonic transducer 603 is changed by the rotationally scanning portion 602 so as to advance toward the wall of the blood vessel 612. The ultrasonic wave reflected on the blood vessel wall is returned to the ultrasonic transducer 603 to be converted into an electric signal and inputted to the transmission and reception section 607. This reflection signal is amplified and then A/D-converted into a digital signal. The digital value of the reflection signal is stored at a predetermined position in the image memory section 609 by means of the scan conversion section 608 in accordance with the writing position which is calculated by the control section 611 on the basis of the position signal from the drive section 606 which corresponds to the scanning direction of the rotationally scanning portion 602. The transmission and reception processing of the ultrasonic wave signal is repeatedly effected during the rotation of the rotationally scanning portion 602, whereby the image in the radial direction obtained by the rotationally scanning operation of the rotationally scanning portion 602 is stored and displayed as an ultrasonic image on the monitor 610.

Figure 22A:
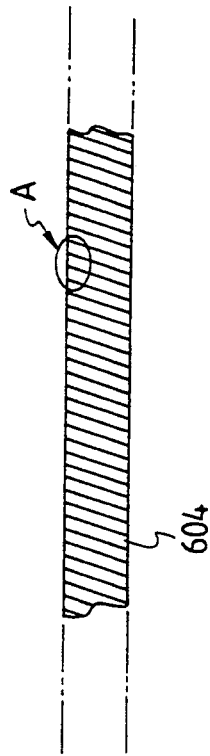
FIGS. 22A to 22C show a detailed arrangement of a torque transmission shaft to be used in the FIG. 21 ultrasonic diagnostic apparatus.
Figure 22B:
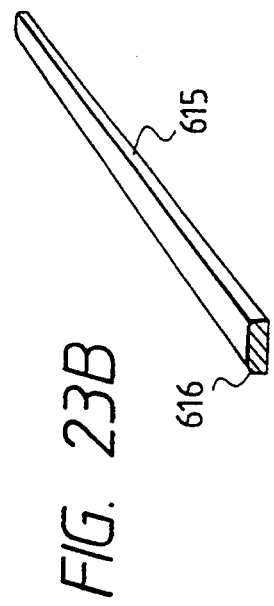
Figure 22C:
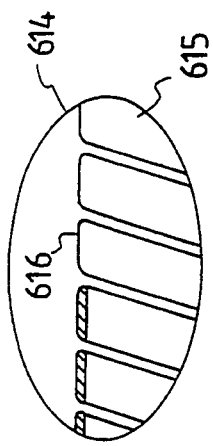

FIGS. 22A to 22C show a detailed arrangement of the torque transmission shaft 604. The torque transmission shaft 604 may be arranged to have a multi-layer spring structure to enhance the transmission force. Numeral 614 represents the outermost layer of the torque transmission shaft 604 and 615 designates an element wire. FIG. 22A shows the entire structure of the torque transmission shaft 604 and FIG. 22C is an enlarged illustration of a portion indicated by an arrow A in FIG. 22A. The cross-section of the element wire 615 of the outermost layer 614 has a rectangular configuration as indicated by an arrow B in FIG. 22C and the outer surface of the outermost layer 614 is flat. For making the outermost layer 614 to be rectangular in the cross-sectional configuration when the torque transmission shaft 604 is constructed so as to have such a spring structure, the element wire 615 is arranged in advance such that its outer surface is convexed or curved toward the outside as illustrated in FIG. 22B. That is, when building tie spring structure, because of the difference between the stresses applied to the outer surface and the inner surface of the element wire 615, the outermost layer 614 can be constructed such that its outer surface has a flat configuration. Accordingly, since the outer surface of the torque transmission shaft 604 is flat, it is possible to reduce the unnecessary friction with respect to the inner surface of the catheter 601 and possible to effectively transfer the rotating force of the drive section 606 to the rotational scanning portion 602.

Figure 23A:
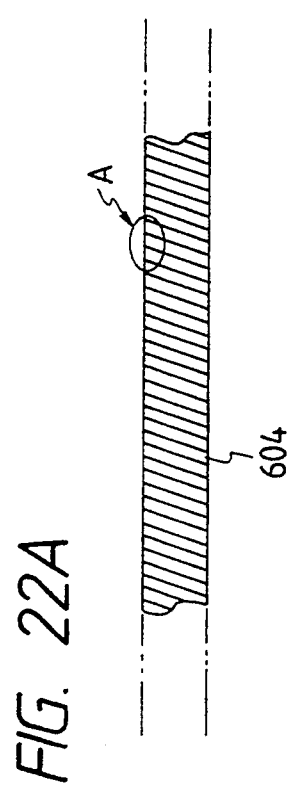
FIGS. 23A to 23C are illustrations for describing an arrangement of a torque transmission shaft of an ultrasonic probe according to a fourteenth embodiment of this invention.
Figure 23B:
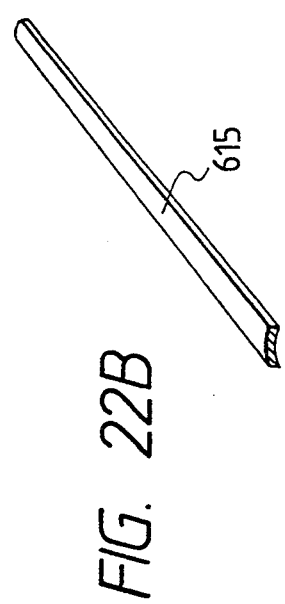
Figure 23C:
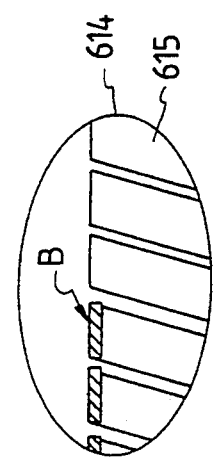

Further, a description will be made hereinbelow in terms of a fourteenth embodiment of this invention. FIGS. 23A to 23C are illustrations for describing an arrangement of the torque transmission shaft 604 of an ultrasonic probe according to the fourteenth embodiment of this invention. FIG. 23A shows the torque transmission shaft 604, FIG. 23B shows the configuration of the element wire 615 and FIG. 23C is an enlarged illustration of a portion of the torque transmission shaft 604 indicated by an arrow A in FIG. 23A. In FIGS. 23A to 23C, numeral 604 represents a torque transmission shaft which may be constructed as having a multi-layer structure, 614 designates an outermost layer of the torque transmission shaft 604, 615 depicts an element wire constituting the torque transmission shaft 604, and 616 denotes a rounding formed on the element wire 615. As illustrated in FIG. 23B, the two corner portions of the upper surface of the element wire 615 for the outermost layer 614 substantially having a rectangular cross section are rounded to form roundings 616. If constructing the spring-like torque transmission shaft 604 using such an element wire 615, sharply protruding portions can be removed from the outermost layer 614 of the torque transmission shaft 604, thereby reducing the unnecessary friction between the torque transmission shaft 604 and the inner surface of the catheter 601 to adequately transferring the rotating force due to the drive section 606 to the rotationally scanning portion 602.

Figure 24A:
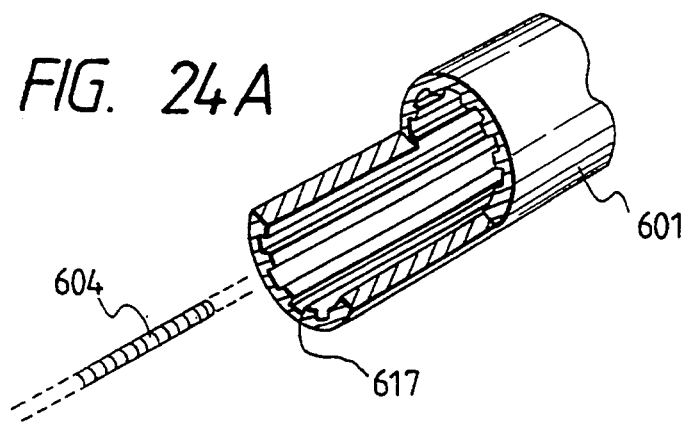
FIGS. 24A to 24C are illustrations of arrangements of a catheter of an ultrasonic diagnostic apparatus according to a fifteenth embodiment of this invention.
Figure 24B:
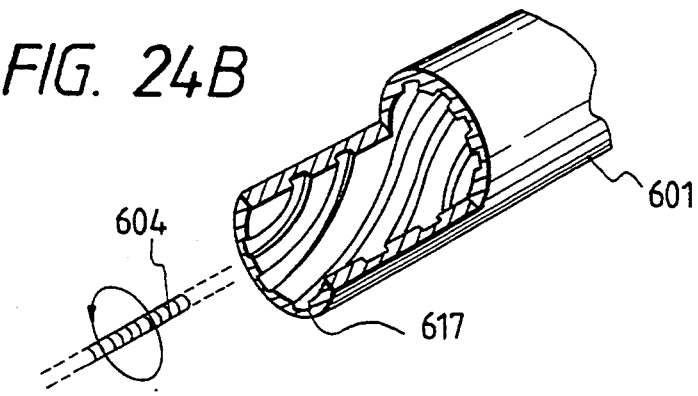
Figure 24C:
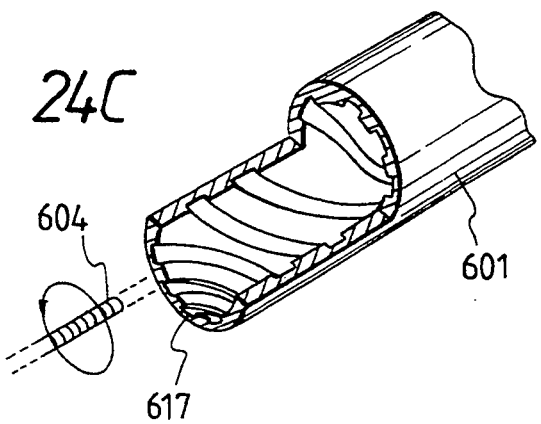

Moreover, a description will be made hereinbelow in terms a fifteenth embodiment of this invention. FIGS. 24A to 24C are illustrations of arrangements of the catheter 601 of an ultrasonic diagnostic apparatus according to the fifteenth embodiment of this invention. In this embodiment, a plurality of grooves are formed in the inner wall of the catheter 601. In FIG. 24A, a plurality of grooves are formed in the inner wall of the catheter 601 in directions parallel to the central axis of the catheter 601, in FIG. 24B a plurality of grooves are spirally formed in the inner wall of the catheter 601 in directions opposite to the rotating direction of the torque transmission shaft 604, and in FIG. 24C, a plurality of grooves are formed in the inner wall of the catheter 601 in the directions as the rotating direction of the torque transmission shaft. 604.

In the case that the torque transmission shaft 604 is inserted into the catheter 601 and the rotating force applied to one end portion of the torque transmission shaft 604 is transferred to the other end portion thereof, although the transferability depends on the feature of the torque transmission shaft 604, the torque transmission shaft 604 can be constructed to have a flexibility when being arranged to have a spring structure. In addition, the transferability of the torque transmission shaft 604 can be improved by constructing the torque transmission shaft 604 as illustrated in FIGS. 22A to 23C. Moreover, when the catheter 601 is constructed as illustrated in FIGS. 24A to 24C, the area of the inner wall of the catheter 601 which comes into contact with the torque transmissions shaft 604 can be reduced so as to reduce the variation of the contact state between the inner surface of the catheter 601 and the outer surface of the torque transmission shaft 604 due to the variation of the bending state.

A description will be described hereinbelow in terms of sixteenth embodiment of this invention. FIGS. 25A and 25B are cross-sectional views showing an arrangement of a drive section of an ultrasonic diagnostic apparatus according to the sixteenth embodiment of this invention. In FIGS. 25A and 25B, in a drive section 702, numeral 706 represents a motor, 707 is an encoder which is disposed on the rotating shaft of the motor 706 and which acts as a position detector, 708 designates a first beating, 709 depicts a second bearing, 710 denotes a first rotating shaft, 711 is a first pulley fixed to the first rotating shaft 710, 712 indicates a second rotating shaft, 713 is a second pulley fixed to the second rotating shaft 712, 714 represents a third bearing, 715 designates a fourth bearing, 716 a main body side connector fixed to the second rotating shaft 712, 717 represents a groove formed on the main body connector 716, 718 denotes a drive belt, 719 is a catheter, 720 depicts a torque transmission shaft, 721 represents a probe side fitting portion fixed to the catheter 719, 722 is a main body side fitting portion fixed to a casing portion of the drive section 702, 723 represents a probe side connector connected to the torque transmission shaft 720, and 724 designates a projecting portion which is provided on the probe side connector 723 and which is engaged with the groove 717 formed in the main body side connector 716. Further, numeral 725 represents an adjusting spring connected to the main body side connector 716 and the probe; side connector 723, 726 is a signal line, 727 is a signal contact portion, and 728 designates a signal connecting portion.

Figure 26A:
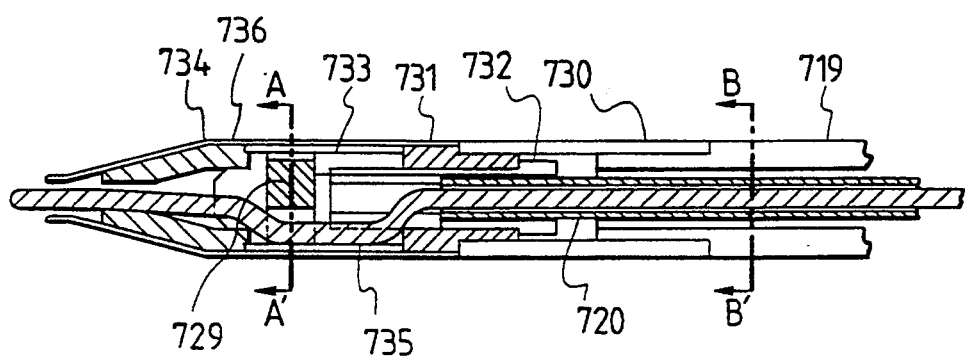
FIG. 26A is a cross-sectional view showing a tip portion of an ultrasonic probe to be used in the ultrasonic diagnostic apparatus according to the sixteenth embodiment.
Figure 26B:
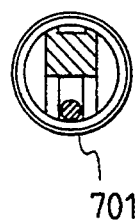
FIG. 26B is a cross-sectional view taken along a line A-A' in FIG. 26A.
Figure 26C:
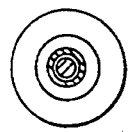
FIG. 26C is a cross-sectional view taken along a line B-B' in FIG. 26A.

Further, FIG. 26A is a cross-sectional view showing a tip portion of an ultrasonic probe to be used in the ultrasonic diagnostic apparatus according to this embodiment. FIG. 26B is a cross-sectional view taken along a line A-A' in FIG. 26A and FIG. 26B is a cross-sectional view taken along a line B-B' in FIG. 26A. In FIGS. 26A to 26C, numeral 729 represents an ultrasonic transducer for transmission and reception of an ultrasonic wave, 730 designates a joint, 731 is a bearing, 732 depicts a rotating shaft, 733 denotes a transducer holder, 734 indicates a cap, 735 indicates a guidewire, and 736 is an acoustic window. The rear end portion of the ultrasonic probe 701 is connected to the drive section 702 and the signal line 726 is connected to the ultrasonic transducer 729.

In operation, when the ultrasonic probe 701 is inserted into a target blood vessel, the ultrasonic transducer 729 is responsive to an ultrasonic wave transmission signal from a transmission and reception section, not shown, through the signal line 726 so as to transmit an ultrasonic wave. The ultrasonic wave transmitted from the ultrasonic transducer 729 is again returned to the ultrasonic transducer 729 so as to be converted into an electric signal which is a reflection signal. This reflection signal is supplied through the signal line 726 and the signal contact portion 727 of the drive section 702 to a main body, not shown, in which the reflection signal is written in an image memory of a DSC (digital scan converter) in accordance with a position signal which is the output signal of the encoder 707 and converted into an image signal such as an NTSC television signal to be displayed as an ultrasonic image on a monitor. For example, the signal contact portion 727 is arranged to have a slip ring structure to obtain the reflection signal from the signal line 726 which is rotated together with the second rotating shaft 712.

The rotation of the ultrasonic transducer 729 is made by the rotational operation of the motor 706 in the drive section 702. That is, due to the rotation of the motor 706, there is rotated the first rotating shaft 710 which is the rotating shaft of the motor 706 and which is supported by the first and second bearings 708 and 709, whereby the first pulley 711 fixedly connected to the first rotating shaft 710 is rotated. Further, the encoder 711 generates a position signal corresponding to the rotation of the motor 706. The rotating force of the first pulley 711 is transferred through the drive belt 718 to the second pulley 713 and further to the second rotating shaft 712 which is supported by the third and fourth bearings 714 and 715 and which is fixedly connected to the second pulley 713. The rotation of the second rotating shaft 712 rotates the main body side connector 716 fixedly connected to at its tip portion. In addition, due to the engagement between the groove 717 formed at the inside of the main body side connector 716 and the projecting portion 724 provided on the probe side connector 723, the rotation of the main body side connector 716 is transferred to the probe side connector 723. Further, since the torque transmission shaft 720 is fixedly connected to the probe side connector 723, the torque transmission shaft 720 is rotated due to the rotation of the probe side connector 723. The connection between the ultrasonic probe 701 and the drive section 702 is effected by the probe side fitting portion 721 fixed to the catheter 719 and the main body side fitting portion 722 provided in the drive section 702 to suppress the rotating operation of the catheter 719.

The tip portion of the torque transmission shaft 720 is fixedly connected to the rotating shaft 732 and the tip portion of the catheter 719 is connected to the joint 730 and the bearing 731 is fixedly connected to the joint 730. Further, the rotating shaft 732 is arranged to be rotatable with respect to the bearing 731, and hence the rotating shaft 732 is rotatable due to the rotation of the torque transmission shaft 720. The transducer holder 733 holds the ultrasonic transducer 729 so that the ultrasonic wave emitting direction is perpendicular to the central axis of the ultrasonic probe 701, and is fixedly connected to the rotating shaft 732 so as to be rotatable due to the rotation of the rotating shaft 732. Accordingly, the rotation of the motor 706 is transferred to the first rotating shaft 710, second rotating shaft 712, main body side connector 716, probe side connector 723, torque transmission shaft 720, rotating shaft 732 and transducer holder 733, thereby allowing the two-dimensional transmission of the ultrasonic wave.

The rotating force due to the motor 706 is transferred to the torque transmission shaft 720 due to the groove 717 formed in the main body side connector 716 and the projecting portion 724 provided on the probe side connector 723. Although due to the arrangement of the groove 717 and the projecting portion 724 the rotating force of the main body side connector 716 is transmitted, the movement of the second rotating shaft 712 in the central axis directions is not limited and the probe side connector 723 is freely movable in the central axis directions of the torque transmission shaft 712 with respect to the main body side connector 716. However, since the main body side connector 716 and the probe side connector 723 are connected to each other through the adjusting spring 725, due to the tension of the adjusting spring 725, the movement of the second rotating shaft in the central axis direction is limited with respect to the main body side connector 716. On the other hand, since the probe side connector 723 is connected to the torque transmission shaft 720, it is also limited by the tension of the torque transmission shaft 720, and as a result, the probe side connector 723 is moved to the position at which the tension of the adjusting spring 725 and the tension entirely applied to the torque transmission shaft 720 are balanced. When the tension of the adjusting spring 725 is arranged to be equal to the tension of the torque transmission shaft 720 so as to obtain an adequate rotation accuracy, it is possible to correct the tension of the torque transmission shaft 720 in accordance with the state variation of the ultrasonic probe 701 to obtain an appropriate stress. The tension of the adjusting spring 725 can be adjusted by the material, the shape and the number of turns.

Figure 27:
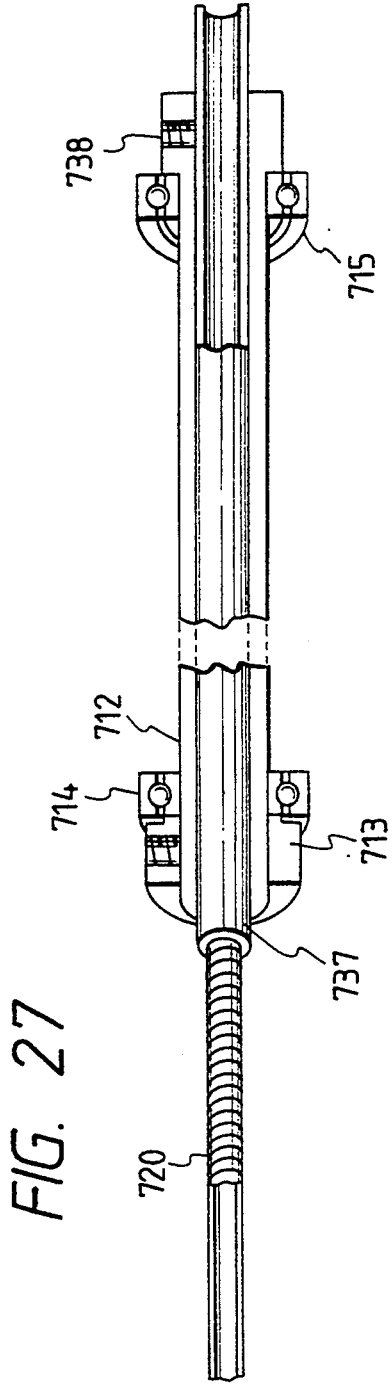
FIG. 27 is a cross-sectional view showing an arrangement of a drive section to be used in an ultrasonic diagnostic apparatus according to a seventeenth embodiment of this invention.

Further, a description will be made hereinbelow in terms of a seventeenth embodiment of this invention. FIG. 27 is a cross-sectional view showing an arrangement of a drive section to be used in an ultrasonic diagnostic apparatus according to the seventeenth embodiment of this invention. The difference between the this embodiment and the above-described embodiment sixteenth embodiment is the connection of the torque transmission shaft 720 and the second rotating shaft 712. In FIG. 27, numeral 737 is a tension control shaft which is inserted into the hollow of the second rotating shaft 712 and which is moveable in the forward and backward directions along the rotational center axis and numeral 738 a movement control section such as a screw for suppressing the movement of the tension control shaft 737. The tension control shaft 737 has a hollow structure into which a signal line, not show, inserted.

Although in the sixteenth embodiment the torque transmission shaft 720 is arranged so that the tension become constant without depending on the state variation of the ultrasonic probe 701, the influence to the rotating accuracy due to the tension variation not only depends on the feature of the torque transmission shaft 720 but also depends on the relation to the catheter 719. That is, the variation in the frictional state between the catheter 719 and the torque transmission shaft 720 occurs due to the variation of the cross-sectional configuration of the catheter 719 so that the tension condition for obtaining the optical rotating accuracy varies.

As well as the sixteenth embodiment, due to the rotation of the torque transmission shaft 720, the ultrasonic wave from the ultrasonic transducer 729 positioned at the tip portion of the ultrasonic probe 701 is two-dimensionally scanned. The rotation of the torque transmission shaft 720 can be achieved by the rotations of the second pulley 713 and the second rotating shaft 712 due to the rotation of the motor 706. On the other hand, the torque transmission shaft 720 is fixedly connected to the tension control shaft 737 and the tension control shaft 737 is rotated in synchronism with the second rotating shaft 712. Accordingly, the torque transmission shaft 720 is rotated by the rotation of the second rotating shaft 712.

In the case that the appropriate tension applied to the torque transmission shaft 720 varies in accordance with the variation of the ultrasonic probe 701, the tension control shaft 737 is moved by the movement control section 738 in the forward and backward directions with respect to the second rotating shaft 712 so that the tension to be applied to the torque transmission shaft 720 is varied so that the torque transmission shaft 720 is controlled to take the optical rotating accuracy.

As described above, the tension control shaft 737 is provided in the second rotating shaft 712 so as to be movable in the forward and backward directions along the rotating axis, and the torque transmission shaft 720 is fixedly connected to the tension control shaft 737 so as to be, together with the second rotating shaft 712, rotated by the movement control section 738 at the time of the rotating operation and to be moved in the forward and backward directions by the movement control section 738 at the time of the tension control operation. Thus, it is possible to change the tension to be applied to the torque transmission shaft 720.

Figure 28:
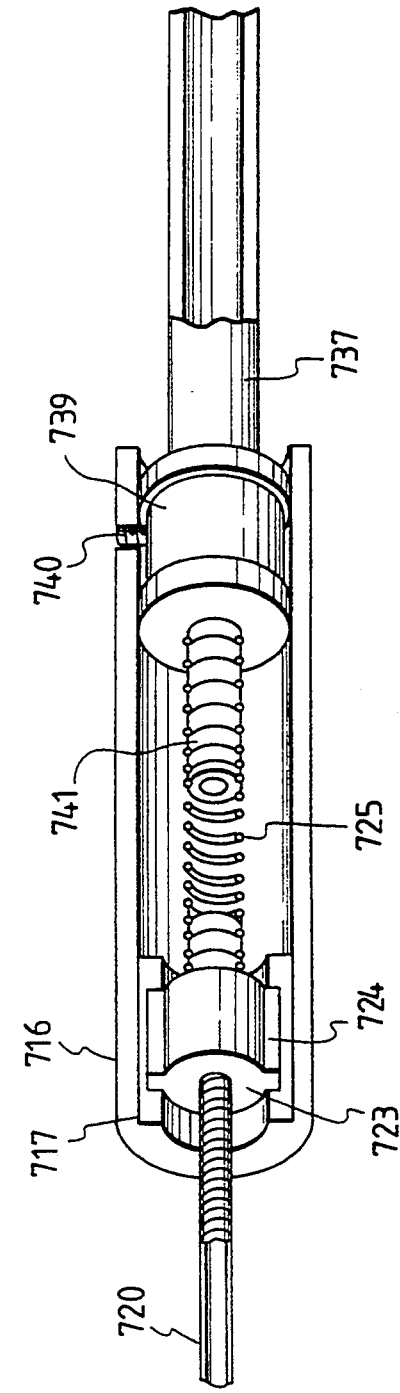
FIG. 28 is a cross-sectional view showing an arrangement of a drive section of an ultrasonic diagnostic apparatus according to an eighteenth embodiment of this invention.

In addition, a description will be made hereinbelow in terms of an eighteenth embodiment of this invention. FIG. 28 is a cross-sectional view showing an arrangement of the drive section 702 of an ultrasonic diagnostic apparatus according to the eighteenth embodiment of this invention where parts corresponding to those in FIGS. 25A and 25B are omitted. the difference between this embodiment and the above-described embodiment is the connection between the torque transmission shaft 720 and the second rotating shaft 712. In FIG. 28, numeral 716 is a main body side connector fixedly connected to the second rotating shaft 712, 717 is a groove, 720 represents a torque transmission shaft, 723 designates a probe side connector fixed to the torque transmission shaft 720, 724 depicts a projecting portion, 725 denotes an adjusting spring, 737 indicates a tension control shaft, 739 is a drum, and 740 represents a screw formed on the main body side connector 716. Due to the screw 740, the drum 739 is rotatable in synchronism with the main body side connector 716. Further, numeral 741 represents an adjusting screw fixedly connected to the tension control shaft 737 and passing through the hollow of the drum 739 so as to be movable in the forward and backward directions with respect to the drum 739. The adjusting screw 741 is trusted into the adjusting spring 725. One end portion of the adjusting spring 725 is fixedly connected to the main body side connector 723 and the other end portion thereof is fixedly connected to the drum 739. The tension control shaft 737 is connected to the second rotating shaft 712 through the movement control portion 738 as illustrated in FIG. 27, and rotated in synchronism therewith at the time of the rotation and moved in the forward and backward directions with respect to the second rotating shaft 712 at the time of the tension control operation. That is, the tension control shaft 737 is movable with respect to the drum 739 with the adjusting screw 741 being trusted into the adjusting spring 725 in the forward and backward directions. A signal line 726, not shown, passes through the hollow portions of the adjusting screw 741 and the tension control shaft 737.

In operation, the rotating operation of the torque transmission shaft 720 is similar to that of the torque transmission shaft in the above-described seventeenth embodiment, and the probe side connector 723 is moved with respect to the main body side connector 716 in accordance with the tension variation of the torque transmission shaft 720 due to the state variation of the ultrasonic probe 701 so as to take a balancing state with respect to the tension of the adjusting spring 725 whereby a constant tension is always applied to the torque transmission shaft 720. In addition, with the tension control shaft 737 being rotated and moved in the forward and backward with respect to the drum 739, the adjusting screw 741 is trusted into the adjusting spring 725 whereby the expanding portion of the adjusting spring 725, i.e., the number of turns which acts as a spring, is variable. The variation of the number of turns causes the variation of the tension of the adjusting spring 725. Thus, it is possible to change the tension to be applied to the torque transmission shaft 720.

As described above, according to this embodiment, the tension control shaft 737 movable in the forward and backward directions along the rotational center axis is provided within the second rotating shaft 712 so as to be rotated together with the second rotating shaft 712. This movement is suppressed by the movement control portion 738. The adjusting screw 741 is fixedly connected to the tip portion of the tension control shaft 737 so that the number of turns of the adjusting spring 725 is changeable by the movement of the adjusting screw 741 in the forward and backward directions. Thus, it is possible to adjust the tension to the torque transmission shaft 720 in accordance with the state variation of the ultrasonic probe 701, thereby changing the tension to the torque transmission shaft 720 without replacing the adjusting spring 725.

Figure 29:
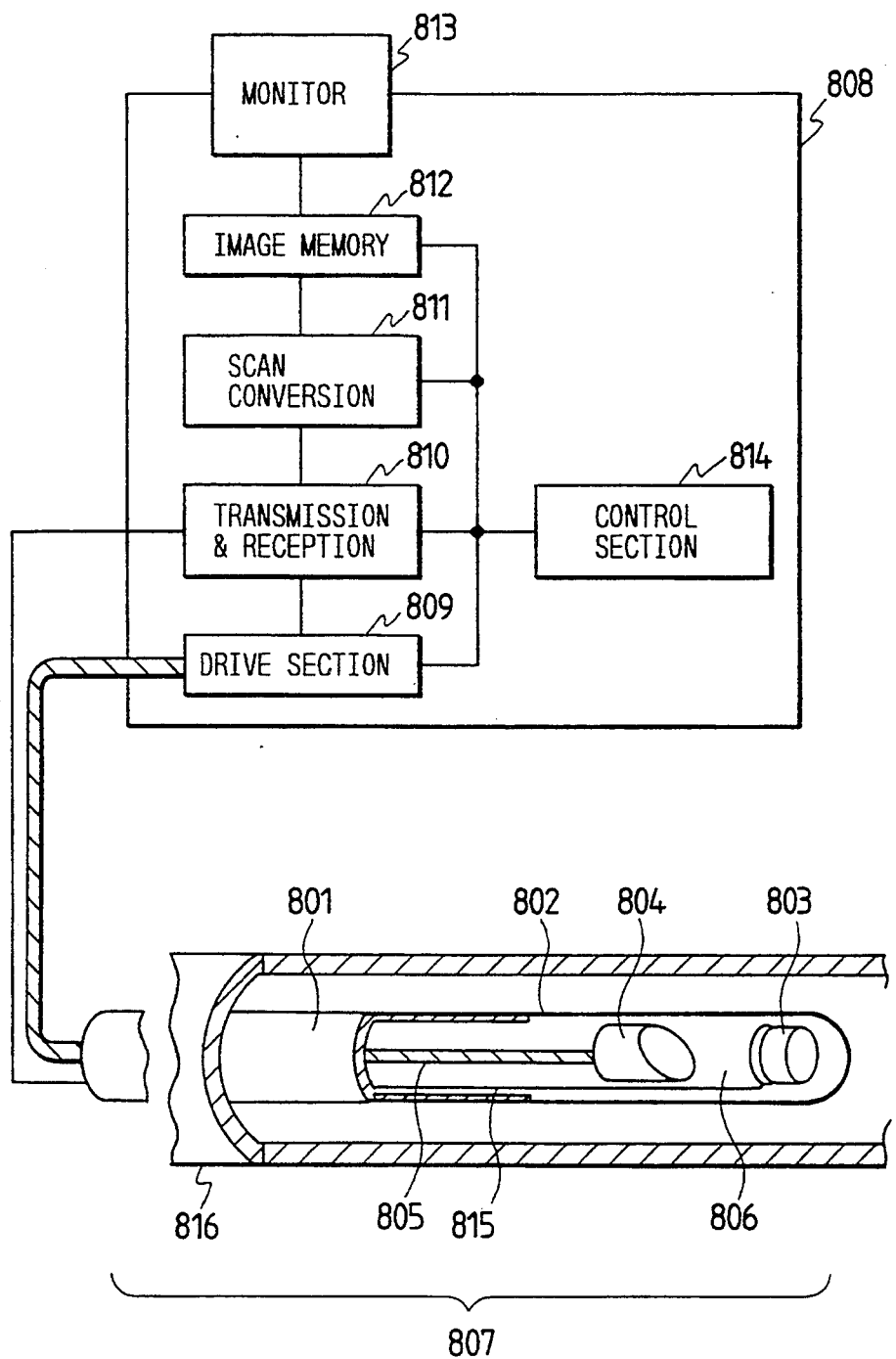
FIG. 29 is a block diagram showing an arrangement of an ultrasonic diagnostic apparatus according to a nineteenth embodiment of this invention.

Moreover, a description will be described hereinbelow in terms of a nineteenth embodiment of this invention. FIG. 29 is a block diagram showing an arrangement of an ultrasonic diagnostic apparatus according to the nineteenth embodiment of this invention. In FIG. 29, numeral 801 represents a catheter, 802 designates an protective coat connected to the tip portion of the catheter 801, 803 depicts an ultrasonic transducer for transmission and reception of an ultrasonic wave, and 804 denotes a rotationally scanning portion of performing a two-dimensional scanning operation of the ultrasonic from the ultrasonic transducer 803. In this embodiment, a mirror is used as the rotationally scanning portion 804. Further, numeral 805 indicates a torque transmission shaft having a flexibility and arranged for transferring a rotating force to the rotationally scanning portion 804, 806 is a propagation medium such as a physiological salt water provided within the protective coat 802, 807 represents an ultrasonic probe comprising the catheter 801, acoustic window 802, ultrasonic transducer 803, rotationally scanning portion 804, torque transmission shaft 805 and propagation medium 806. Further, numeral 808 is a main body comprising a drive section 809 including a motor connected to the torque transmission shaft 805 and an encoder, a transmission and reception section 810 including an ultrasonic pulse transmission circuit, a reception amplifier, an A/D converter and others. Further, in the main body 808 there are included a scan conversion section 811 connected to the transmission and reception section 810, an image memory section 812 connected to the scan conversion section 811, a monitor 13 connected to the image memory section 812, a control section 814 connected to the drive section 809, transmission and reception section 810, and scan conversion section 811 and image memory section 812. Numeral 814 is a signal line between the ultrasonic transducer 805 and the transmission and reception section 810 and 16 designates a blood vessel. The protective coat 802 is for preventing the contact between the propagation medium 806 and the blood and is arranged to prevent the ultrasonic wave attenuation.

FIGS. 30A to 30D are detailed illustrations of the torque transmission shaft 805. FIG. 30A shows the entire arrangement of the torque transmissions shaft 805, FIG. 30B is an illustration of a cross section of an element wire constituting the torque transmission shaft 804, FIG. 30C is an enlarged illustrated of a portion of the torque transmission shaft 805 indicated by character B in FIG. 30A, FIG. 30D is an enlarged illustration of a portion of the torque transmission shaft 804 indicated by character A in FIG. 30A. In FIGS. 30A to 30D, numeral 817 represents the outermost layer of a multilayered spring structure for the torque transmission shaft 805, 818 designates an inner layer provided at the inside of the outermost layer 817, and 820 depicts a gap in the spring structure, 820 is a gap in the spring structure. In FIG. 30A, character L represents a length of a portion which has a structure as illustrated in FIG. 30D and which is a portion (flexible portion) to be bent when the ultrasonic probe 807 is inserted into the coronary artery. In FIG. 30B, the element wire has a thickness 822 and a width 823. The element wires constituting the outermost layer 817 are substantially equal in the thicknesses 822 and the widths 823 to each other. The outer diameters of the constructed outermost layer 817 are substantially the same.

In operation, when the tip portion of the ultrasonic probe 807 reaches a target diseased part within the blood vessel 816, the drive section rotates the torque transmission shaft 805 to rotate the rotationally scanning portion 804 positioned at the tip portion of the ultrasonic probe 807. With the rotationally scanning portion 804 being rotated, the transmission and reception section 810 supplies an ultrasonic transmission signal to the ultrasonic transducer 803. The ultrasonic transducer 803 receives the reflection ultrasonic wave to convert it into an electric signal which is in turn supplied to the transmission and reception section 810 to be amplified and converted into a digital signal. This digital signal is stored at a predetermined position of the image memory section 812 by the scan conversion section 811 under the control of the control section 814 in accordance with a position signal corresponding to the scanning direction of the ultrasonic wave due to the rotationally scanning portion 804. When repeatedly performing this operation, the image in the radial direction is stored in the memory section 812 and displayed as an ultrasonic image on the monitor 813.

According to this embodiment, as illustrated FIG. 30D, in a portion of the torque transmission shaft 805 which is required to be sufficiently flexible for the insertion into the coronary artery and which has the length L, the element wires 821 is coiled so as to build a spring structure having the gap 819 between the wire turns as illustrated in FIG. 30D. On the other hand, in the other portion of the torque transmission shaft 805, a plurality of element wires (a set of 3 element wires in the illustration) arranged in parallel to each other are coiled so as to build a spring structure having the gap 820 between the turns of the wire set as illustrated in FIG. 30C, As a result, the width of the element wire constituting the portion indicated by A in FIG. 30A is three times of the width of the element wire constituting the portion indicated by B in FIG. 30A. Thus, transferability of the portion indicated by B is improved and the flexibility of the portion indicated by A is improved.

Figure 31A:
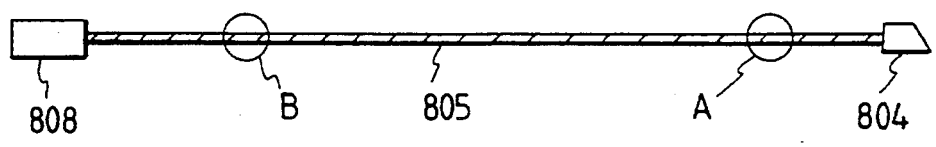
FIGS. 31A to 31C are illustrations of an arrangement of a torque transmission shaft to be used in an ultrasonic diagnostic apparatus according to a twentieth embodiment of this invention.
Figure 31B:
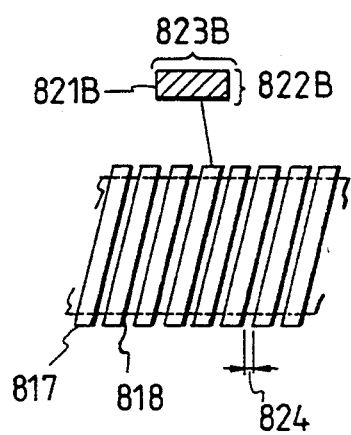
Figure 31C:
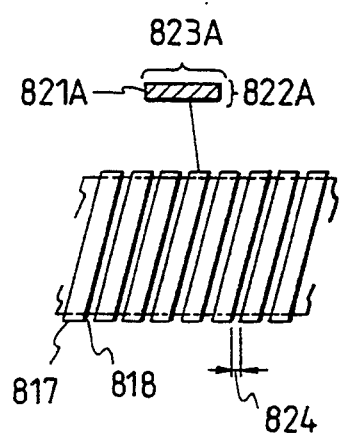

Further, FIGS. 31 A to 31C are illustrations of an arrangement of a torque transmission shaft to be used in an ultrasonic diagnostic apparatus according to a twentieth embodiment of this invention. FIG. 31A shows the entire arrangement of the torque transmission shaft 804, FIG. 31B is an enlarged illustration of a portion indicated by character B in FIG. 31A and FIG. 31C is an enlarged illustration of a portion indicated by character A in FIG. 31A. As illustrated in FIGS. 31B and 31C, although the width 823B of the element wire 821B constituting the portion B is equal to the width 823A of the element wire 821A constituting the portion A and the gap 824 between the turns of the element wire 821B is equal to the gap 824 between the turns of the element wire 821A, the thickness 822B of the element wire 821B constituting the portion B is arranged to be greater than the thickness 822A of the element wire 821A constituting the portion A. Thus, the flexibility of the tip portion side of the torque transmission shaft 805 is more improved as compared with the rear side of the torque transmission shaft 805, and on the other hand, the transferability of the rear side of the torque transmission shaft 805 is more improved as compared with the tip portion side there of. This arrangement can meet both the requirement of the flexibility and transferability of the torque transmission shaft 805.

Figure 32A:
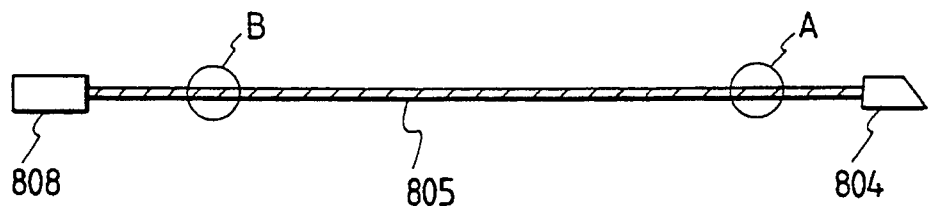
FIGS. 32A to 32C are illustrations of an arrangement of a torque transmission shaft to be used in an ultrasonic diagnostic apparatus according to a twenty first embodiment of this invention.
Figure 32B:
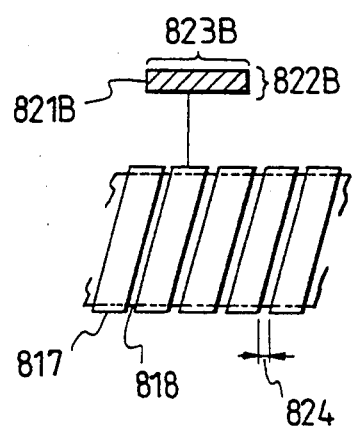
Figure 32C:
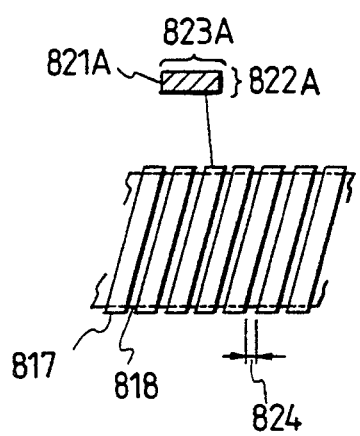

FIGS. 32A to 32C are illustrations of an arrangement of a torque transmission shaft to be used in an ultrasonic diagnostic apparatus according to a twenty first embodiment of this invention. As illustrated in FIGS. 32A to 32C, according to this embodiment, although the portions A and B (the tip portion and rear portion of the torque transmission shaft 805) are equal in the thickness of the element wire and the gap between the turns to each other, the width 823B of the element wire 821B constituting the portion B is arranged to be wider than the width 823A of the element wire 821A constituting the portion A. This arrangement can also provide the flexibility and transferability to the torque transmission shaft 805.

Figure 33:
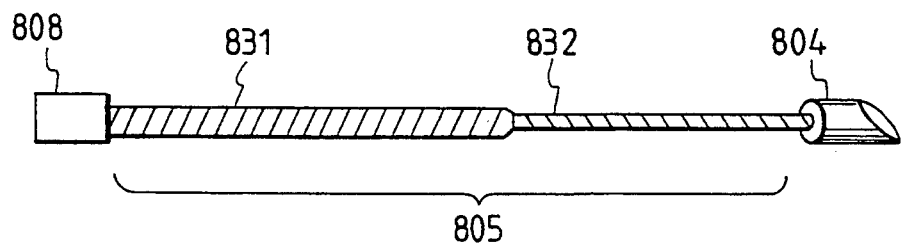
FIG. 33 is an illustration of an arrangement of a torque transmission shaft to be used in an ultrasonic diagnostic apparatus according to a twenty second embodiment of this invention.

FIG. 33 is an illustration of an arrangement of a torque transmission shaft 805 to be used in an ultrasonic diagnostic apparatus according to a twenty second embodiment of this invention. In FIG. 33, the torque transmission shaft 805 is arranged to have a multi-layered structure and the number of layers of the rear side portion 831 of the torque transmission shaft 805 is greater (for example, by one) than the number of layers of the tip portion 832 having a length necessary for the insertion into the coronary artery. This arrangement can also provide the flexibility and transferability to the torque transmission shaft 805.

In the above-described twenty to twenty second embodiments, it is also appropriate that the gap between the turns of the element wire constituting the tip portion of the torque transmission shaft 805 is arranged to be wider than the gap between the turns of the element wire constituting the rear side portion thereof.

Figure 34:
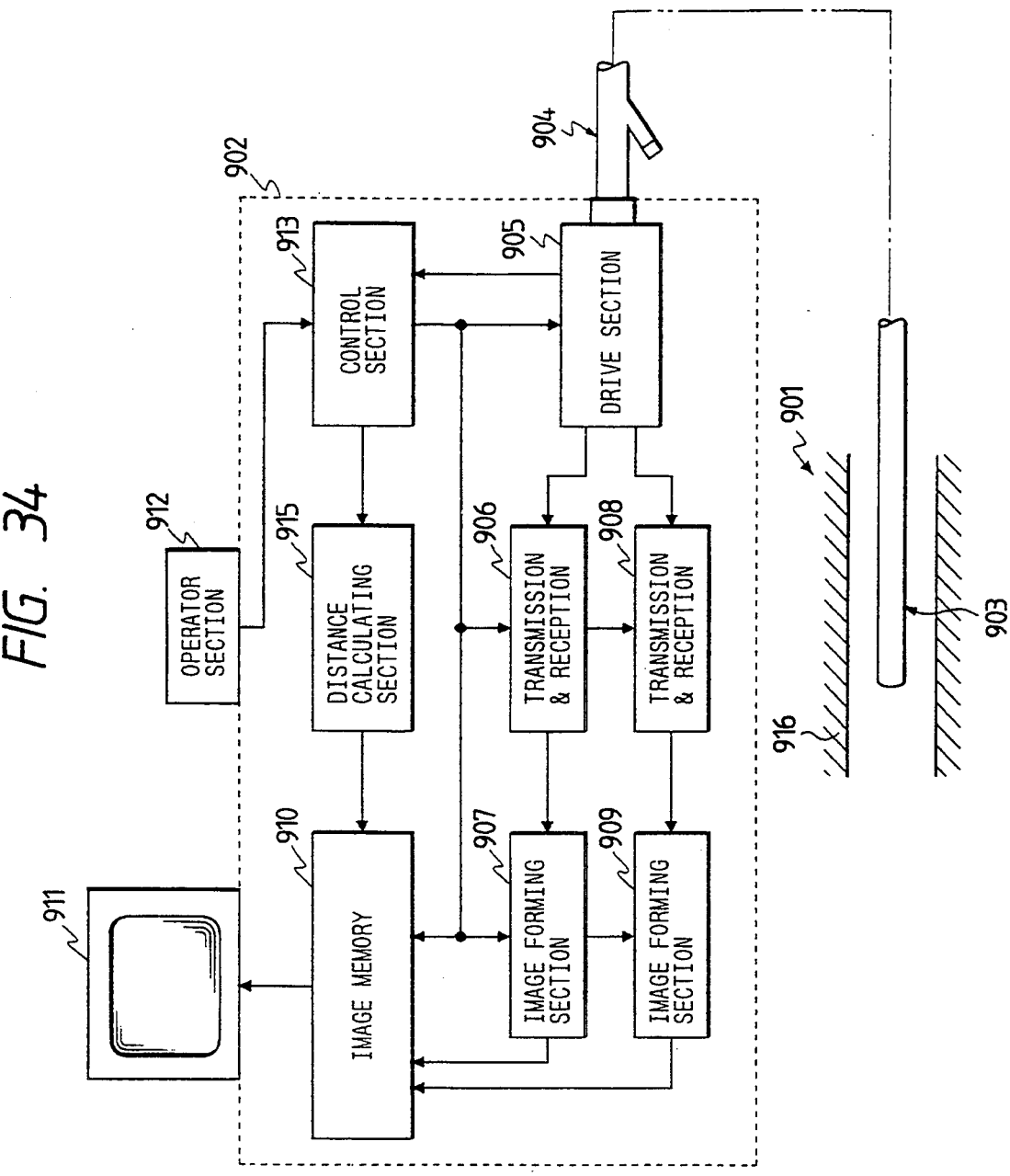
FIG. 34 is a block diagram showing an arrangement of an ultrasonic diagnostic apparatus according to a twenty third embodiment of this invention.

A description will be described hereinbelow in terms of a twenty third embodiment of this invention. FIG. 34 is a block diagram showing an arrangement of an ultrasonic diagnostic apparatus according to the twenty third embodiment of this invention. In FIG. 34, the ultrasonic diagnostic apparatus of this embodiment comprises an ultrasonic probe 901 and a main body 902. The main body 902 includes a drive section 905 for generating a driving force, a peripheral direction transmission and reception section 906 connected to the drive section 905, a peripheral direction image forming section 907 connected to the peripheral direction transmission and reception section 906, a forward direction transmission and reception section 908 connected to the drive section 905, a forward direction image forming section 909 connected to the forward direction transmission and reception section 908, an image memory section 910 connected to the peripheral direction image forming section 907 and the forward direction image forming section 909, a monitor 911 connected to the image memory section 910 for displaying an ultrasonic image, an operator section 912 comprising a keyboard, switch and other elements for inputting various kinds of control instructions, a control section 913 connected to the operator section 912 and a distance calculating section 914 connected to the control section 913.

Figure 35:
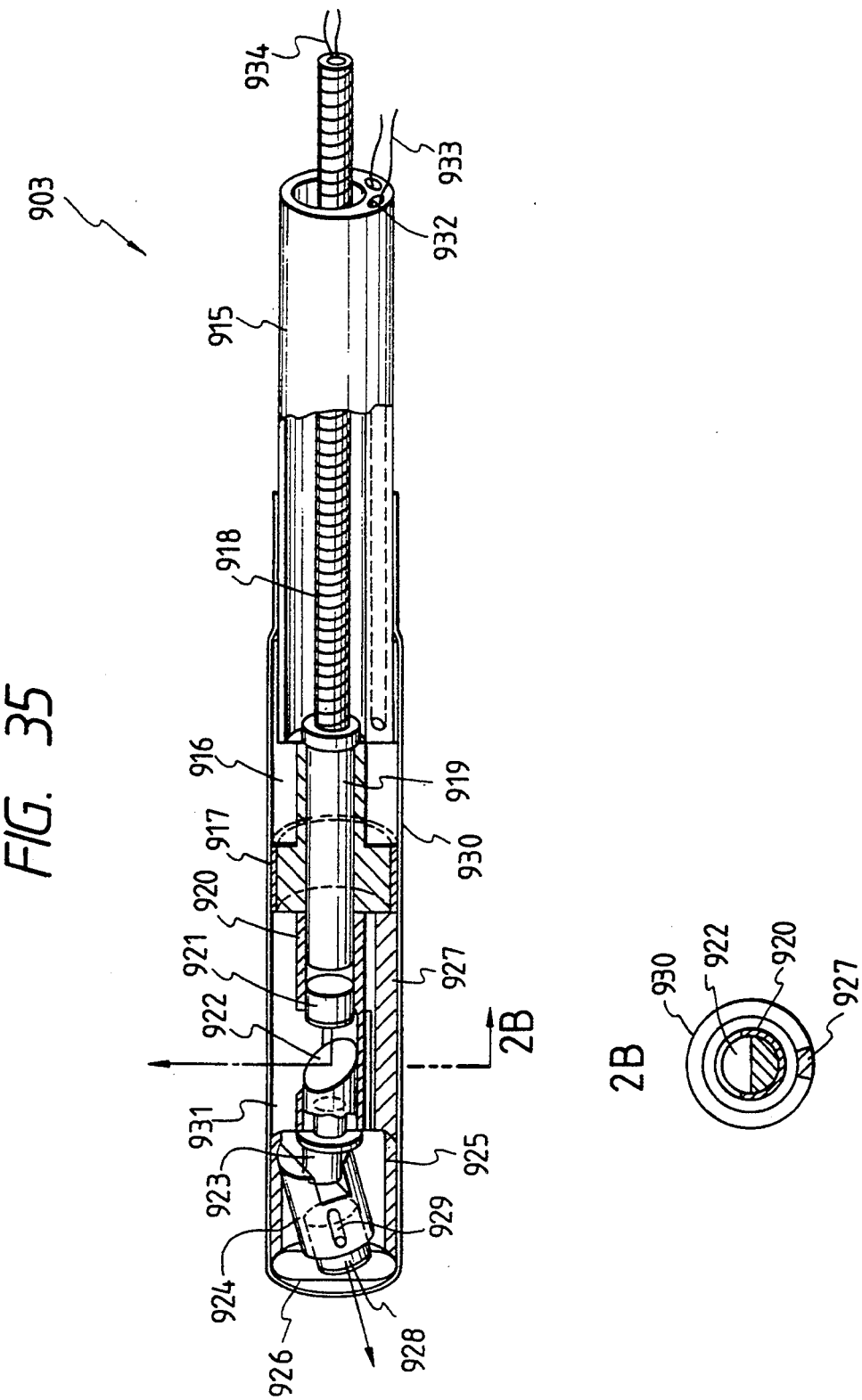
FIG. 35 is a cross-sectional view showing an arrangement of an ultrasonic probe of the FIG. 34 ultrasonic diagnostic apparatus.

FIG. 35 is a cross-sectional view showing an arrangement of the ultrasonic probe 901. In FIG. 35, numeral 915 represents a catheter 915 having a flexible hollow structure, 916 designates a shaft having a hollow structure and fixed to the tip portion of the catheter 915, 917 depicts a bearing having a hollow structure inserted into the hollow portion of the shaft 916, 918 indicates a torque transmission shaft having a flexible multi-layered spring structure and arranged to transfer the rotating force of the drive section 905 up to a tip portion side 903 of the ultrasonic probe 901, and 919 is a rotating shaft inserted into the hollow portion of the bearing 917 and fixed to the tip portion of the torque transmission shaft 918. Further, numeral 920 represents a cylindrical rotator fixed to the tip portion side of the rotating shaft 919 and having an opening in the ultrasonic emitting direction, 921 designates a peripheral direction ultrasonic transducer which is provided in the rotator 920 and whose ultrasonic wave emitting direction is coincident with the direction of the axis of the ultrasonic probe 901, and 922 depicts a mirror provided in opposed relation to the peripheral direction ultrasonic transducer 921 and having a reflection surface with a reflection angle (for example, 45°) whereby the ultrasonic wave transmitted from the peripheral direction ultrasonic transducer 921 is reflected toward an opening of the rotator 920. Moreover, numeral 923 represents an eccentric shaft fixed to or inserted into the tip portion side of the rotator 920, 924 designates a transducer holder having a groove 959 engaged with the contact surface of the eccentric shaft 923, 925 denotes a cap having a sectoral scanning center shaft for the transducer holder 924 and fixedly connected through a beam 927 to the bearing 917, 926 indicates an acoustic window provided at the front side of the cap 925 for the forward direction ultrasonic wave, 928 is a forward direction ultrasonic transducer fixed to the transducer holder 924, 929 is a pivot shaft which is the sectral scanning center shaft for the transducer holder 924, and 930 represents a protective coat for covering the tip portion side 903 of the ultrasonic probe 901, at least covering the portion from the shaft 916 up to the top of the ultrasonic probe 901. Still further, numeral 931 represents a space provided at the inside of the protective coat 930, 932 designates a plurality of lumens provided in a thick portion of the catheter 915, 933 represents signal lines provided within the lumens 932 for the forward direction ultrasonic transducer 928, and 934 designates signal lines provided within the torque transmission shaft 918 for the peripheral direction ultrasonic transducer 921.

Figure 36:
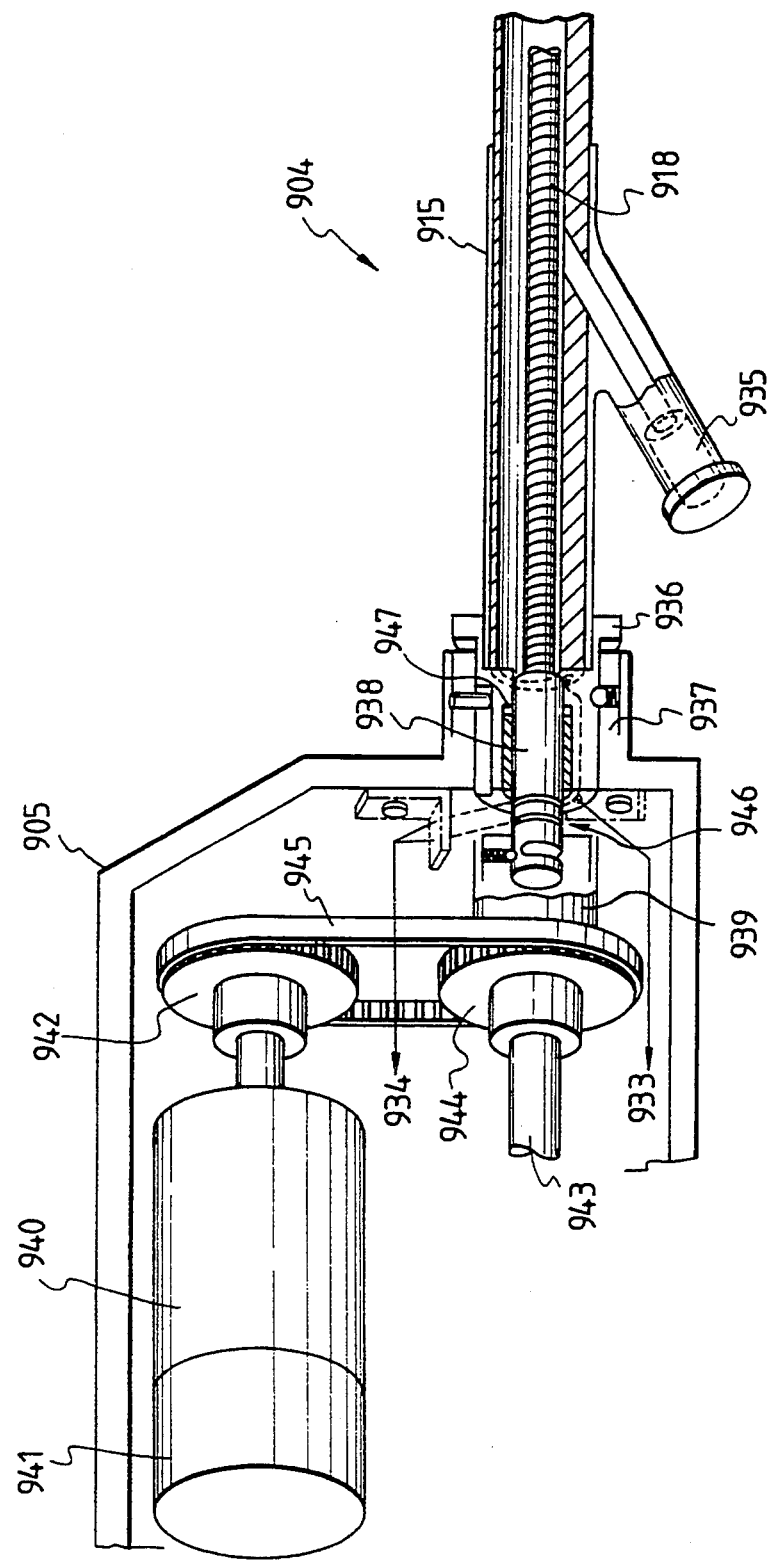
FIG. 36 is an illustration showing an arrangement of a connecting portion between the ultrasonic probe and a drive section of the FIG. 34 ultrasonic diagnostic apparatus.

FIG. 36 is an illustration showing an arrangement of a connecting portion between a rear end portion 904 of the ultrasonic probe 901 and the drive section 905. In FIG. 36, numeral 935 represents a propagation medium injecting inlet formed in a branched portion of the catheter 915 in which the torque transmission shaft 918 is not provided, 936 designates a probe side fitting portion, 937 depicts a main body side fitting portion fixed to the drive section 905, 938 denotes a probe side connector fixedly connected to the torque transmission shaft 918, 939 indicates a main body side connector engaged with the probe side connector 938 so as to transfer the rotating force of the drive section 905, 940 is a motor, 941 a position detector such as an encoder for obtaining the rotation information of the motor 940, 942 is a first pulley connected to the rotating shaft of the motor 940, 943 represents a second rotating shaft for rotating the main body side connector 939, and 944 is a second pulley connected to the second rotating shaft 943. Further, numeral 945 designates a drive belt for transferring the rotating force of the first pulley 942 to the second pulley 944, 946 represents a slip ring type signal contact portion provided at the second rotating shaft 943, and 947 designates an oil sealing member provided within the main body side fitting portion 937 for preventing the propagation medium from entering into the drive section 905.

The operation of the ultrasonic diagnostic apparatus thus arranged will be described hereinbelow. When the tip portion 903 of the ultrasonic probe 901, the motor 940 of the drive section 905 is driven by the control section 913 which is responsive to the instruction from the operator section 912. The rotating force of the, motor 940 rotates the first pulley 942, drive belt 945, second pulley 944 and second rotating shaft 943. Before the treatment, the connection of the rear end portion 904 of the ultrasonic probe 901 is performed through the probe side connector 936 and the main body side connector 937 so that the rotating force of the second rotating shaft 943 is transferred through the main body side connector 939 and the probe side connector 938 to the torque transmission shaft 918. The rotating force transferred to the torque transmission shaft 918 rotates the rotating shaft 919 and the rotator 920 with respect to the bearing 917 which is, together with the shaft 916, connected to the catheter 915. Although the bearing 917 is preferable to be a ball bearing or a lot bearing, in the case that the tip portion 903 is inserted into the coronary artery, the outer diameter of the catheter 915 is required to be below 9 F (F: ⅓ millimeter), more preferably below 6 F, and hence the bearing 917 is constructed using a plastic material having a small frictional coefficient.

Figure 37:
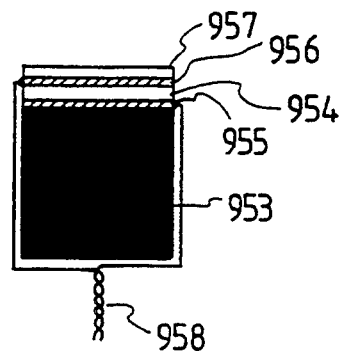
FIG. 37 shows an arrangement of a peripheral direction ultrasonic transducer to be used in the FIG. 34 ultrasonic diagnostic apparatus.

When the rotator 920 is rotating, the peripheral direction transmission and reception section 906 generates a transmission electric signal which is in turn supplied through the signal line 934 to the peripheral direction ultrasonic transducer 921. The peripheral direction ultrasonic transducer 921 generates an ultrasonic wave in accordance with the electric signal therefrom. FIG. 37 shows an arrangement of the peripheral direction ultrasonic transducer 921. As shown in FIG. 37, the ultrasonic transducer 921 comprises a backing load member 953, a piezoelectric plate or film 954 made of a piezoelectric ceramic, a piezoelectric crystal and a high polymer and interposed between electrodes 955 and 956, a multi-layered acoustic matching member 957 having a thickness determined in correspondence with the ultrasonic wave, and signal lines 958 connected to the electrodes 955 and 956. The acoustic matching layer 957 is arranged to achieve an effectively propagation of the ultrasonic wave into the propagation medium and made of a material, for example, having an intermediate acoustic impedance between the acoustic impedances of the piezoelectric film 954 and the propagation medium. The ultrasonic wave transmitted from the peripheral direction ultrasonic transducer 921 propagates within the propagation medium provided within the space 931 and is reflected by the mirror 922 to the direction perpendicular to the axis of the ultrasonic probe 901 (peripheral direction) so as to be outputted from the opening of the rotator 920 and directed toward the wall of the blood vessel after passing through the protective coat 930. The protective coat 930 is arranged to have a thin thickness and an acoustic impedance close to the acoustic impedance of the propagation medium or the blood. The protective coat 930 may be made of a silicon or the like having an adequate attenuation characteristic. The signal line 934 is connected to the peripheral direction transmission and reception section 906 without being twisted at the signal contact portion 946.

The ultrasonic wave reflected on the blood vessel walls is received by the peripheral direction ultrasonic transducer 921 and processed such as amplified and detected in the peripheral direction transmission and reception section 906. The output of the peripheral direction transmission and reception section 906 is supplied to the peripheral direction image forming section 907. If this operated repeatedly effected during the rotating operation of the rotator 920, the peripheral scanning operation can be achieved. The peripheral direction image is formed on the basis of the output of the position detector 941 in accordance with the well-known digital scan conversion technique and stored in the image memory section 910 and then displayed on the monitor 911.

Figure 38:
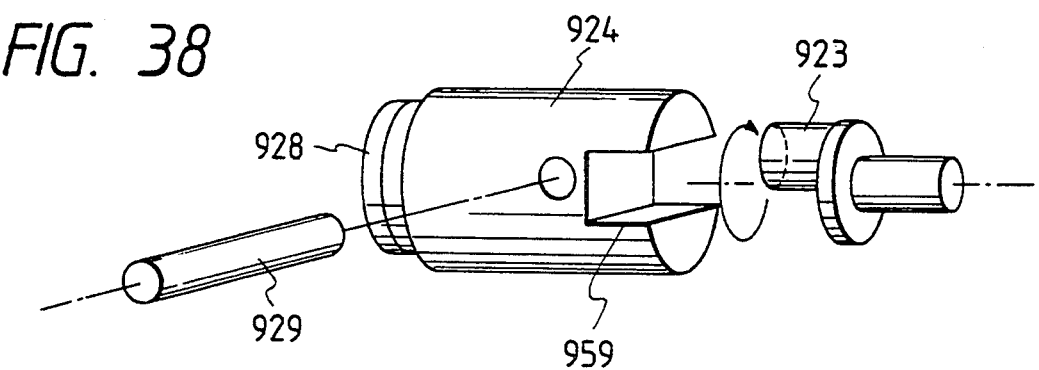
FIG. 38 is an enlarged illustration of an eccentric shaft and a transducer holder to be used in the FIG. 34 ultrasonic diagnostic apparatus.

Due to the rotation of the torque transmission shaft 918, the rotator 920 rotates the eccentric shaft 923 positioned at its tip portion, whereby the transducer holder 924 performs the sectoral scanning operation through the groove 959 engaged with the eccentric shaft 923. Further, this sectral scanning operation of the transducer holder 924 will be described hereinbelow with reference to FIG. 38. FIG. 38 is an enlarged illustration of the eccentric shaft 923 and the transducer holder 924. In FIG. 38, the eccentric shaft 923 is inserted into the groove 959 formed in the transducer holder 924, and the transducer holder 924 is connected through the pivot shaft 929 to the cap 925. The eccentric shaft 923 is rotated as indicated by an arrow and the groove 959 and the pivot shaft 929 converts the rotating operation of the eccentric shaft 923 into the up and down movement of the rear side of the transducer holder 924 whereby the tip portion of the transducer holder 924 sectrally moves so as to two-dimensionally move the forward direction ultrasonic transducer 928. During this sectoral scanning operation, the processes similar to the process for the peripheral direction image are effected in the forward direction transmission and reception section 908 and the forward direction image forming section 909 so that the forward sectoral scanning image is stored in the image memory 910 and displayed on the monitor 911. Here, it is appropriate that the signal line 932 is disposed between the catheter 915 and the torque transmission shaft 918.

Figure 39A:
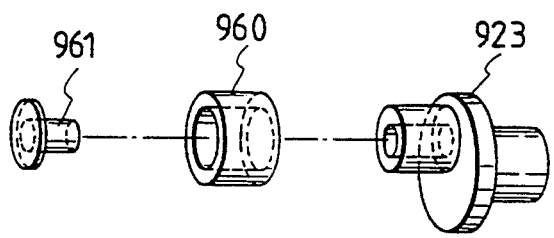
FIGS. 39A and 39B show a different engaging arrangement between the eccentric shaft and the transducer holder.
Figure 39B:
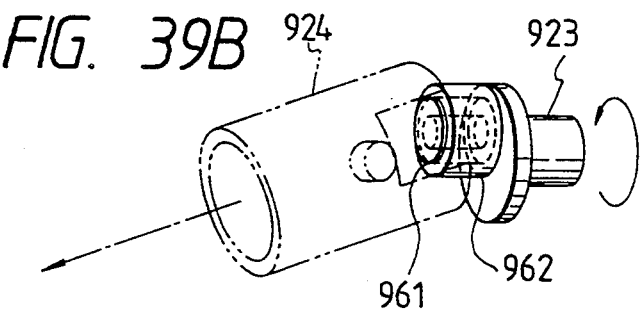

Since this sectoral scanning operation is effected with the eccentric shaft 923 contacting with the groove 959 of the transducer holder 924, the accuracy of the sectoral scanning operation depends on the frictional resistance between the eccentric shaft 923 and the groove 959. Thus, at least one of the eccentric shaft 923 and the transducer holder 924 may be made of a resin such as a fluorine resin having a small frictional resistance. Here, it is also appropriate that, as illustrated in FIG. 39A, the eccentric shaft 923 is inserted into a cylindrical rotatable bearing 960 and kept by a pin 961 so that the rotatable bearing 960 is rotated in accordance with the rotation of the eccentric shaft 923, and as illustrated in FIG. 39B, the rotatable bearing 960 is inserted into the groove 959 of the transducer holder 924. This arrangement can achieve a more smooth conversion into the sectral scanning movement.

Figure 40:
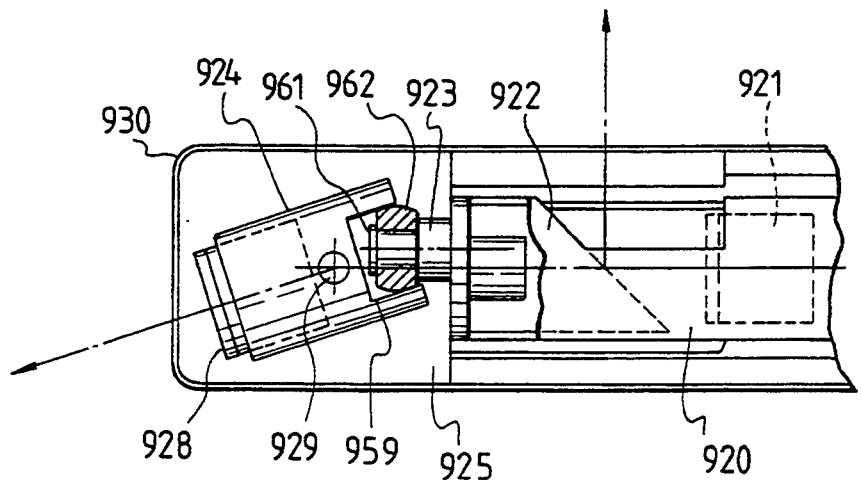
FIG. 40 is a cross-sectional view showing a tip portion of an ultrasonic probe to be used in an ultrasonic diagnostic apparatus according to a twenty fourth embodiment of this invention.
Figure 41A:
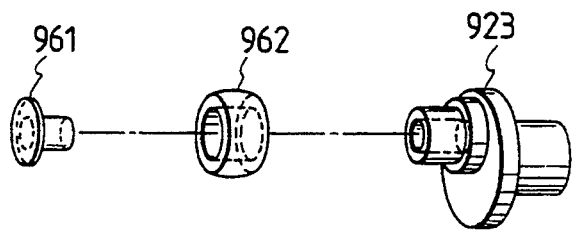
FIGS. 41A and 41B are illustrations for describing a connecting arrangement of a transducer holder and an eccentric shaft of an ultrasonic probe to be used in the FIG. 40 ultrasonic diagnostic apparatus.
Figure 41B:
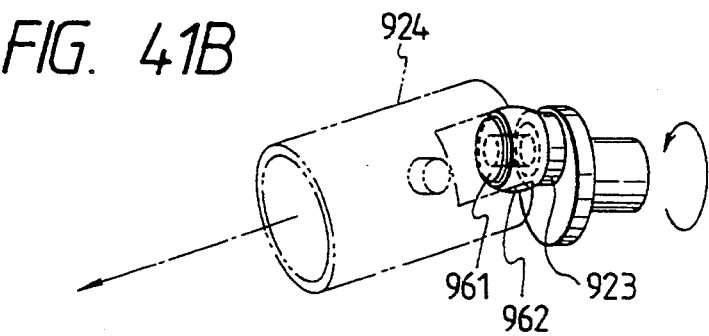

A twenty fourth embodiment will be described hereinbelow. FIG. 40 is a cross-sectional view showing a tip portion of an ultrasonic probe to be used in an ultrasonic diagnostic apparatus according to the twenty fourth embodiment of this invention where parts which are not illustrated in FIG. 40 are the same as the parts in the above-described twenty third embodiment. In FIG. 40, numeral 920 represents a rotator, 921 designates a peripheral direction ultrasonic transducer, 922 depicts a mirror, 923 denotes an eccentric shaft provided at the tip potion side of the rotator 920, 924 indicates a transducer holder, 925 is a cap, 928 represents a forward direction ultrasonic transducer, 929 designates a pivot shaft, 930 depicts a protective coat, 962 is a rotatable bearing inserted into the eccentric shaft 923, and 961 is a pin. As illustrated in FIGS. 41A and 41B, the rotatable bearing 962 has a spherical appearance unlike the appearance of the rotatable beating 962 shown in FIG. 39A and is preferable to be made of a fluorine resin having a small friction coefficient.

Figure 42A:
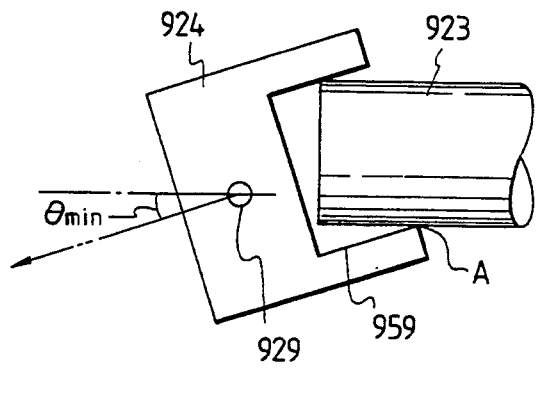
FIGS. 42A-42B and 43A to 43C are illustrations for describing the contact relation between the eccentric shaft and the transducer holder in the twenty third embodiment.
Figure 42B:
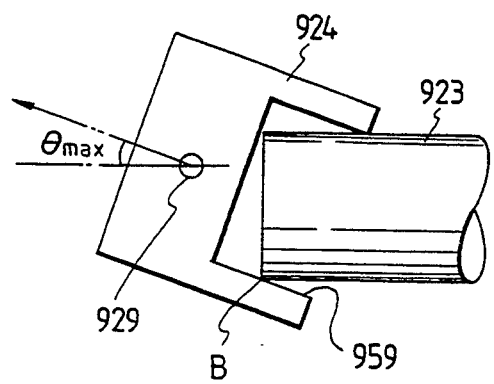
Figure 43A:
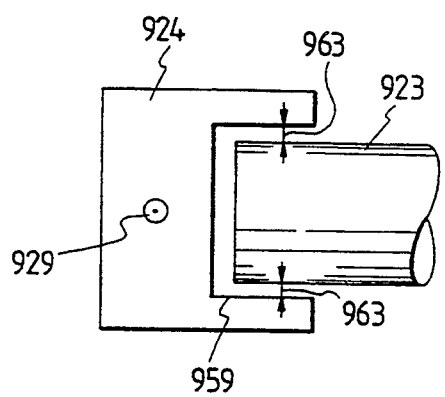
Figure 43B:
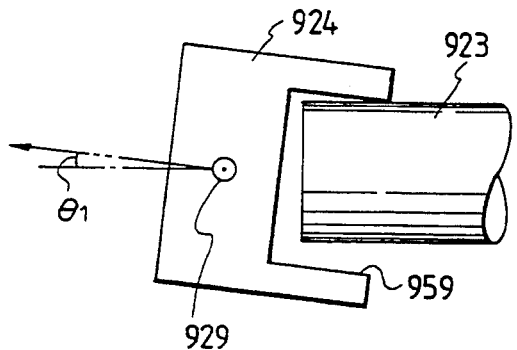
Figure 43C:
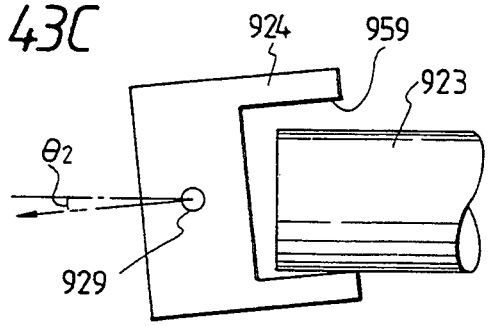

Here, the contact relation between the eccentric shaft 923 and the transducer holder 924 in the above-described twenty third embodiment will be described hereinbelow with reference to FIGS. 2A to 43C. In the forward direction sectral scanning operation according to the twenty third embodiment, the contact position between the eccentric shaft 923 and the transducer holder 924 varies with respect to the variation of the scanning angle, and the gap between the eccentric shaft 923 and the transducer holder 924 becomes the maximum at the vicinity of the scanning angle of 0° so that difficulty is encountered to accurately identify the scanning angle. As illustrated in FIG. 42A, .when the scanning angle is $\theta(min)$ which is the minimum value, the eccentric shaft 923 and the transducer holder 924 are brought into contact with each other at the point A. On the other hand, when the scanning angle is $\theta(max)$ which is the maximum value, the contact point is changed to the point B. This change means that the scanning state varies when the scanning angle is 0° (scanning angle in the variation of the contact point). This characteristic is not preferable in identifying the scanning angle. Further, as shown in FIG. 43A, the gap 963 between the eccentric shaft 923 and the transducer holder 924 becomes the maximum when the scanning angle is at the vicinity of 0°, and hence the scanning angle becomes 01 as illustrated in FIG. 43B or $\theta2$ as illustrated in FIG. 43C. This is because the eccentric shaft 923 has a cylindrical configuration and the width of the groove 959 of the transducer holder 924 viewed from the eccentric shaft 923 side varies in accordance with the scanning angle. Accordingly, if a high accuracy is not required for the ultrasonic image, the above-described twenty third embodiment arrangement is useful from the viewpoint of easy manufacturing.

Returning to the twenty fourth embodiment, the operation of the diagnostic apparatus arranged as described above will be described with reference to FIGS. 40 to 41B. The rotator 920 rotated by the torque transmission shaft 918 rotates the eccentric shaft 923 provided at its tip portion, whereby the transducer holder 924 performs the sectral scanning operation about the pivot shaft 929 through the groove 959 engaged with the eccentric shaft 923. The eccentric shaft 923 is inserted into the rotatable bearing 962 having a spherical configuration and having a diameter equal to or smaller than the width of the groove 959 and kept therein by the pin 961 so that the rotatable bearing 962 is rotatable with respect to the eccentric shaft 923. Thus, the eccentric shaft 923 inserted into the groove 959 of the transducer holder 924 allows the sectral scanning operation of the transducer holder 924. Further, since the rotatable bearing 962 has a spherical appearance, the contact between the eccentric shaft 923 and the groove 959 always occurs at a constant portion irrespective of the variation of the scanning angle, thereby obtaining a stable scanning state. At the time of the sectral scanning operation, the transmission and reception of an ultrasonic wave are effected in the forward direction transmission and reception section 908 and the image formation is effected in the forward direction image forming section 909, whereby a forward direction sectral scanning image is stored in the image memory section 910 and displayed on the monitor 911.

Figure 44A:
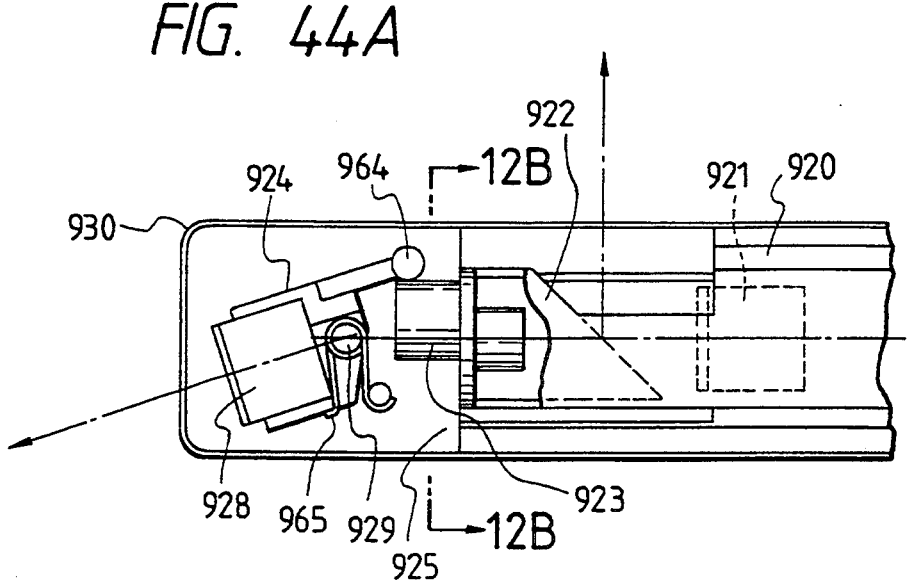
FIGS. 44A and 44B are illustration of a modification of the twenty fourth embodiment of this invention.
Figure 44B:
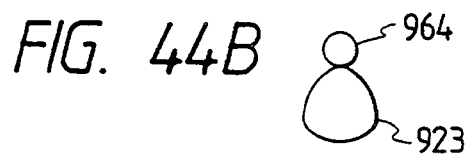

FIGS. 44A and 44B are illustration of a modification of the twenty fourth embodiment of this invention where the corresponding parts are marked with the same numerals. In FIGS. 4A and 44B, numeral 964 represents a contact provided at the rear end portion of the transducer holder 924, the tip portion (contacting portion with the eccentric shaft 923 of the contact 964) being arranged to have a spherical configuration, and further numeral 965 is a spring whereby the contact 964 always comes into contact with the eccentric shaft 964. In operation, the transducer holder 924 is limited by the spring 965 so that the contact 964 fixed to the rear end portion of the transducer holder 924 is always brought into contact with the eccentric shaft 923 and the forward direction ultrasonic transducer 928 faces the direction which depends on the contact 964, the spring 965 and the eccentric shaft 923. The rotator 920 rotated through the torque transmission shaft 918 rotates the eccentric shaft 923 so that the contact 964 is moved up and down so as to cause the transducer holder 924 to perform the sectral scanning operation. Here, in order to obtain a desired scanning state, for example, obtain a smooth movement, it is also appropriate that the cross section of the eccentric shaft 923 is arranged to have a non-circular configuration as illustrated in FIG. 44B.

Figure 45:
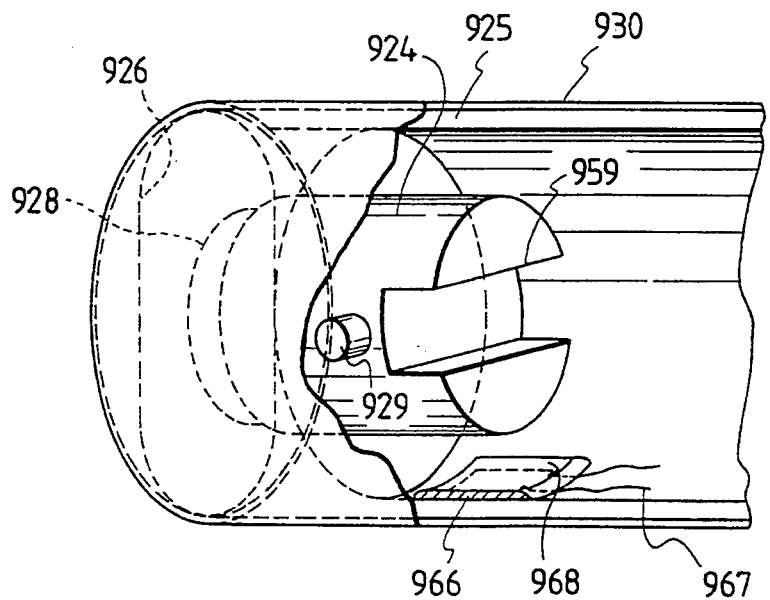
FIG. 45 shows an arrangement of a tip portion of an ultrasonic probe of an ultrasonic diagnostic apparatus according to a twenty fifth embodiment of this invention.

Further, a description will be made hereinbelow in terms of a twenty fifth embodiment of this invention. FIG. 45 shows an arrangement of a tip portion of an ultrasonic probe of an ultrasonic diagnostic apparatus according to the twenty fifth embodiment of this invention. In FIG. 45, 924 represents a transducer holder, 925 designates a cap, 926 depicts an acoustic window, 928 denotes a forward direction ultrasonic transducer, 929 indicates a pivot shaft, 930 is a protective coat, 966 represents a position sensor, 967 designates signal lines, and 968 is a coat member for fixing the position sensor 966 to the inside of the cap 925 and for protecting it. The coat member 968 is made of an insulating material. The position sensor 966 is positioned at a portion of the inside of the cap 925 which comes into contact with the read end portion of the transducer holder 924 when the scanning angle is the maximum.

Figure 46:
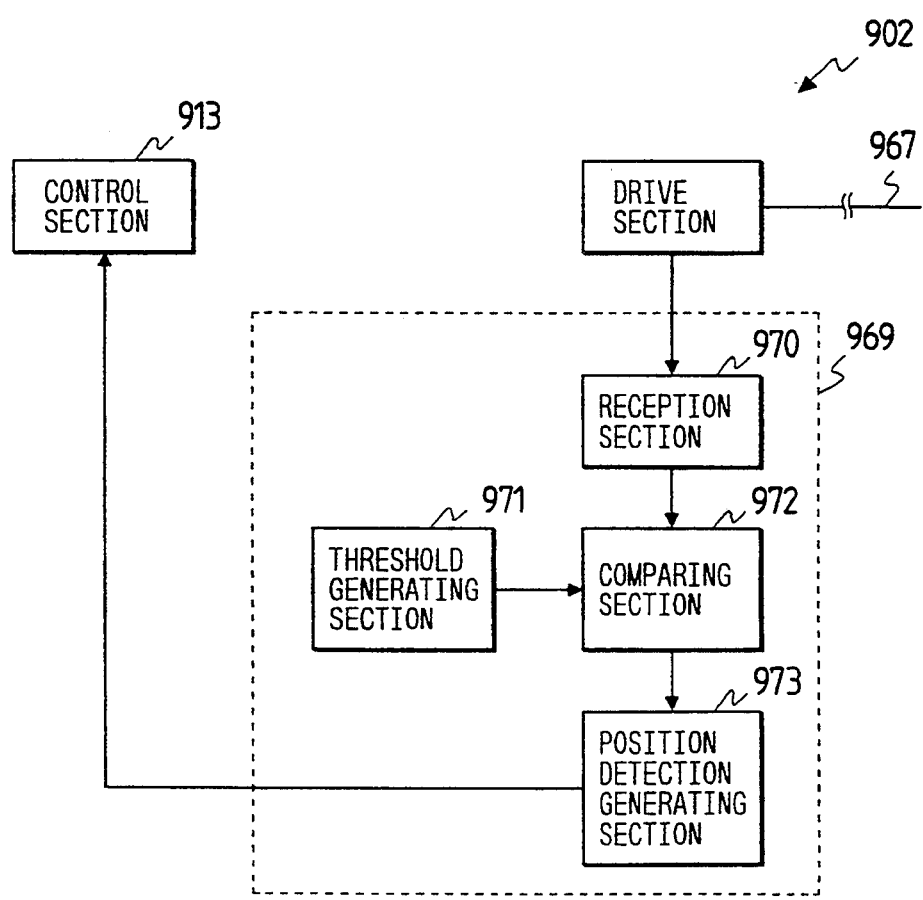
FIG. 46 is a block diagram showing an arrangement of a main body of the ultrasonic diagnostic apparatus according to the twenty fifth embodiment of this invention.

FIG. 46 is a block diagram showing an arrangement of a main body 902 of the ultrasonic diagnostic apparatus according to the twenty fifth embodiment. Parts which are not illustrated are the same as those in FIG. 34. In FIG. 46, numeral 969 represents a position detecting section, 970 is a reception section connected to the drive section 905 and electrically connected to the signal line 967, 971 is a threshold value generating section, 972 depicts a comparing section connected to the threshold value generating section 972 and further to the reception section 970, and 973 is a position detection signal generating section connected to the comparing section 972. The position detecting section 969 comprising the reception section 970, threshold value generating section 971, comparing section 972 and position detection signal generating section 973. In the twenty third and twenty fourth embodiments, the measurement of the scanning angle of the forward direction ultrasonic transducer 928 is effected by the position detector 941 such as an encoder connected to the motor 940 of the drive section 905. Here,, since the torque transmission shaft 918 has a flexible multi-layered spring structure, in the case that the rotating force due to the motor 940 is transferred to the tip portion side 903 of the ultrasonic probe 901, the phase lag occurs between the drive section 905 and the tip portion side 903 of the ultrasonic probe 901. If this phase lag is always constant, the scanning angle of the forward direction ultrasonic transducer 928 can be corrected and identified. However, in the case that the state of the ultrasonic probe 901 is changed, for example, in the case that the ultrasonic probe 901 is inserted into an object having a complex configuration, the phase lag also varies so as to make difficult the correction of the phase lag. This variation depends on the characteristic of the torque transmission shaft 918. The characteristic of the torque transmission shaft 918 means the flexibility and transferability. However, when improving the transferability so as to prevent the phase lag, the flexibility is deteriorated so as to make difficult the insertion into the object having a complex configuration.

The operation of the ultrasonic diagnostic apparatus according to the twenty fifth embodiment will be described hereinbelow with reference to FIGS. 45 and 46. As well as in the twenty third and twenty fourth embodiments, the transducer holder 924 performs the sectral scanning operation. At the time of the first sectral scanning operation, the rear portion of the transducer holder 924 comes into contact with the position sensor 966 one time. The position sensor 966 is for effectively converting the shock due to the contact into an electric signal and, for example, made of a piezoelectric material. As the piezoelectric material there is a high-polymer piezoelectric material such as a PVDF and a PVDF copolymer.

FIG. 47 shows an arrangement of a position sensor. In FIG. 47, numeral 974 is a high-polymer piezoelectric member, and 975 represents electrodes provided on both surfaces of the high-polymer piezoelectric member 974. Two signal lines 967 are electrically connected to the electrodes 975. The position sensor 966 is adhered to the inside of the cap 925 through a coat member 968 or an adhesive such as an epoxy resin having an insulating characteristic.

Due to the contact with the transducer holder 924, the position sensor 966 generates an electric pulse signal. As illustrated in FIG. 48A, the position sensor 966 outputs one pulse signal in correspondence with one sectral scanning operation. This output is inputted through the signal line 967 to the reception section 970 of the position detecting section 969. The reception section 970 obtains and outputs an envelop detection signal having a waveform as illustrated in FIG. 48B. In the comparing section 972, the output of the reception section 970 is compared with the threshold value produced in the threshold value generating section 971, and in accordance with the comparison result, the position signal generating section 973 generates a position detection signal corresponding to the contact between the position sensor 966 and the transducer holder 924 as illustrated in FIG. 48C and outputs it the control section 913.

The control section 913 produces various timing signals on the basis of the position detection signal, the various timing signals being supplied to the peripheral direction transmission and reception section 906, peripheral direction image forming section 907, forward direction transmission and reception signal 908, forward direction image forming section 909 and image memory section 910. Here, in the case of forming a forward direction sectral scanning ultrasonic image, a more accurate image can be formed if the scanning angle information is obtained at every transmission of the forward direction ultrasonic transducer 928. However, since it can be assumed that the rotation of the torque transmission shaft 918 is substantially constant during one revolution, the image can be formed only with such a position signal corresponding to a reference position. The position signal can also be used for the formation of the peripheral direction ultrasonic image.

Figure 49:
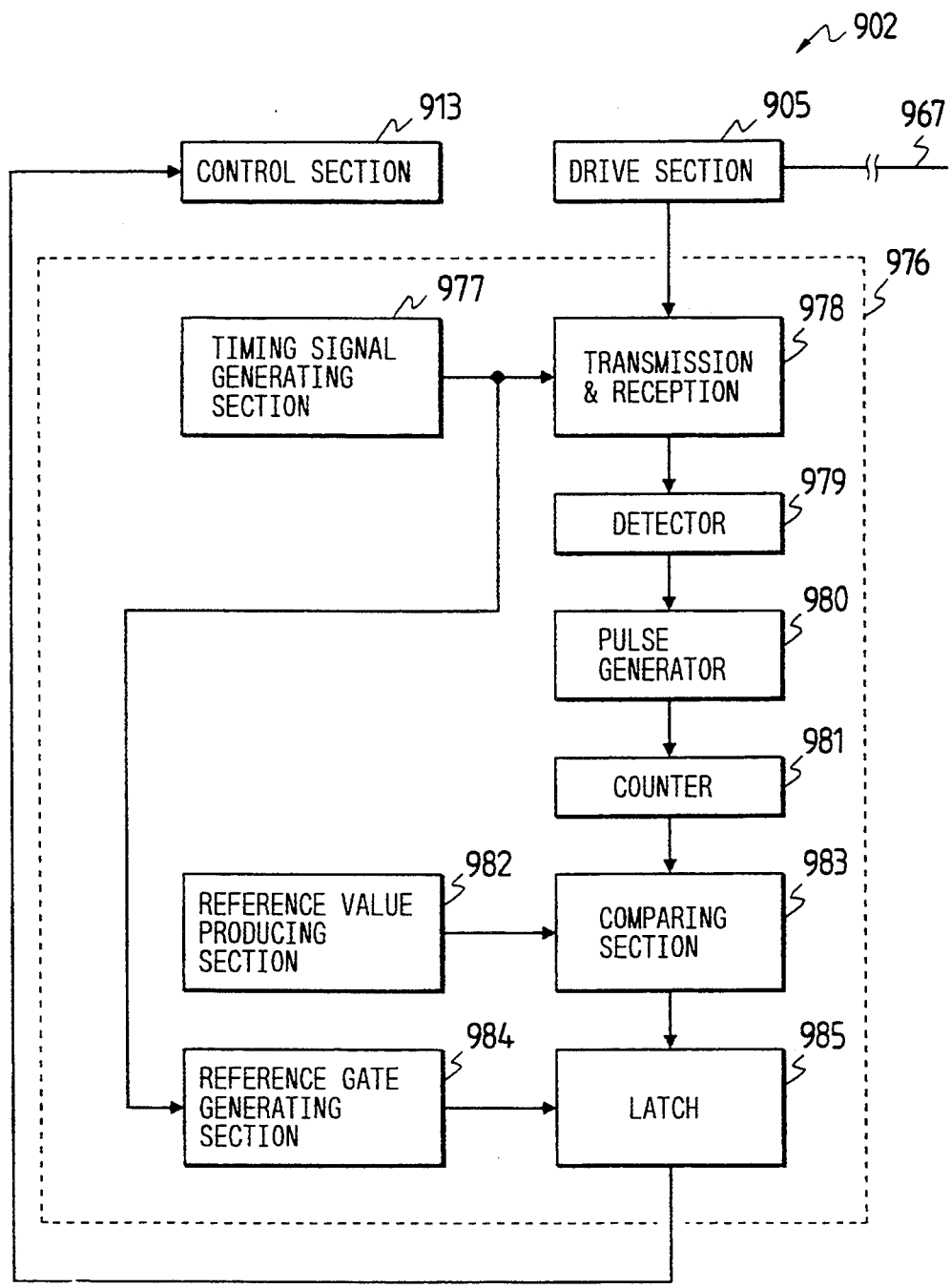
FIG. 49 is a block diagram showing an arrangement of an ultrasonic diagnostic apparatus according to a twenty sixth embodiment of this invention.

A twenty sixth embodiment of this invention will be described with reference to FIG. 49. The arrangement of an ultrasonic probe of an ultrasonic diagnostic apparatus according to this embodiment is the same structure as that of the above-described twenty fifth embodiment. However, although in the twenty fifth embodiment the transducer holder 924 is brought into contact with the position sensor 966 at the time that the scanning angle becomes the maximum, in this embodiment the position sensor 966 is disposed at the inside of the cap so as not to be brought into contact with the transducer holder 924 at the time that the scanning angle becomes the maximum. FIG. 49 is a block diagram showing an arrangement of an ultrasonic diagnostic apparatus according to the twenty sixth embodiment of this invention where parts similar to those in FIG. 34 are not illustrated. In FIG. 49, numeral 976 represents a position detecting section, 977 designates a timing signal generating section, 978 depicts a transmission and reception section connected to the timing signal generating section 977, 979 denotes a detecting section connected to the transmission and reception section 978, 980 indicates a pulse producing device connected to the detecting section 979, 981 is a counter section connected to the pulse producing device 980, 982 represents a reference value producing section, 983 designates a comparing section connected to the reference value producing section 982, 984 depicts a reference gate generating section connected to the timing signal generating section 977, and 985 denotes a latch section for temporarily holding the output of the comparing section 983 in accordance with a gate signal generated by the reference gate generating section 984. The output of the latch section 985 is coupled to the control section 913.

In operation, the transducer holder 924 performs the sectral scanning operation, and during the sectral scanning operation, the transmission and reception section 978 of the position detecting section 976 supplies a transmission electric signal to the position sensor 966 at the timing generated by the timing signal generating section 977 of the position detecting section 976. In response to the transmission electric signal, the position sensor 966 transmits an ultrasonic wave which in turn propagate within the propagation medium so as to be reflected at a portion of the outer wall of the transducer holder 924 which is the closest portion to the position sensor 966. The reflection wave from the ultrasonic transducer 924 is received by the position sensor 966 and adequately amplified in the transmission and reception section 978 and detected in the detecting section 979. The timing signal generating section 977 measures the time between the generation of the transmission electric signal and the generation of the reflection signal on the basis of the detection signal from the detecting section 979, thereby identifying the position of the transducer holder 924 to obtain a reference position.

Here, in the case of inserting the ultrasonic probe 901 into a narrow object such as a coronary artery, the tip portion of the ultrasonic probe 901 is required to be arranged to be below 6 F and hence the variation of the distance between the transducer holder 924 and the position sensor 966 is extremely small. Thus, the position sensor 966 is required to have a high frequency characteristic. However, the heightening of the frequency makes difficult the manufacturing of the position sensor 966. In addition, the respective parts of the position detecting section 976 are required to be arranged to have an excellent high frequency characteristic so that the apparatus becomes complex and costly. Thus, the position detecting section 976 is constructed as illustrated in FIG. 49.

Figure 50:
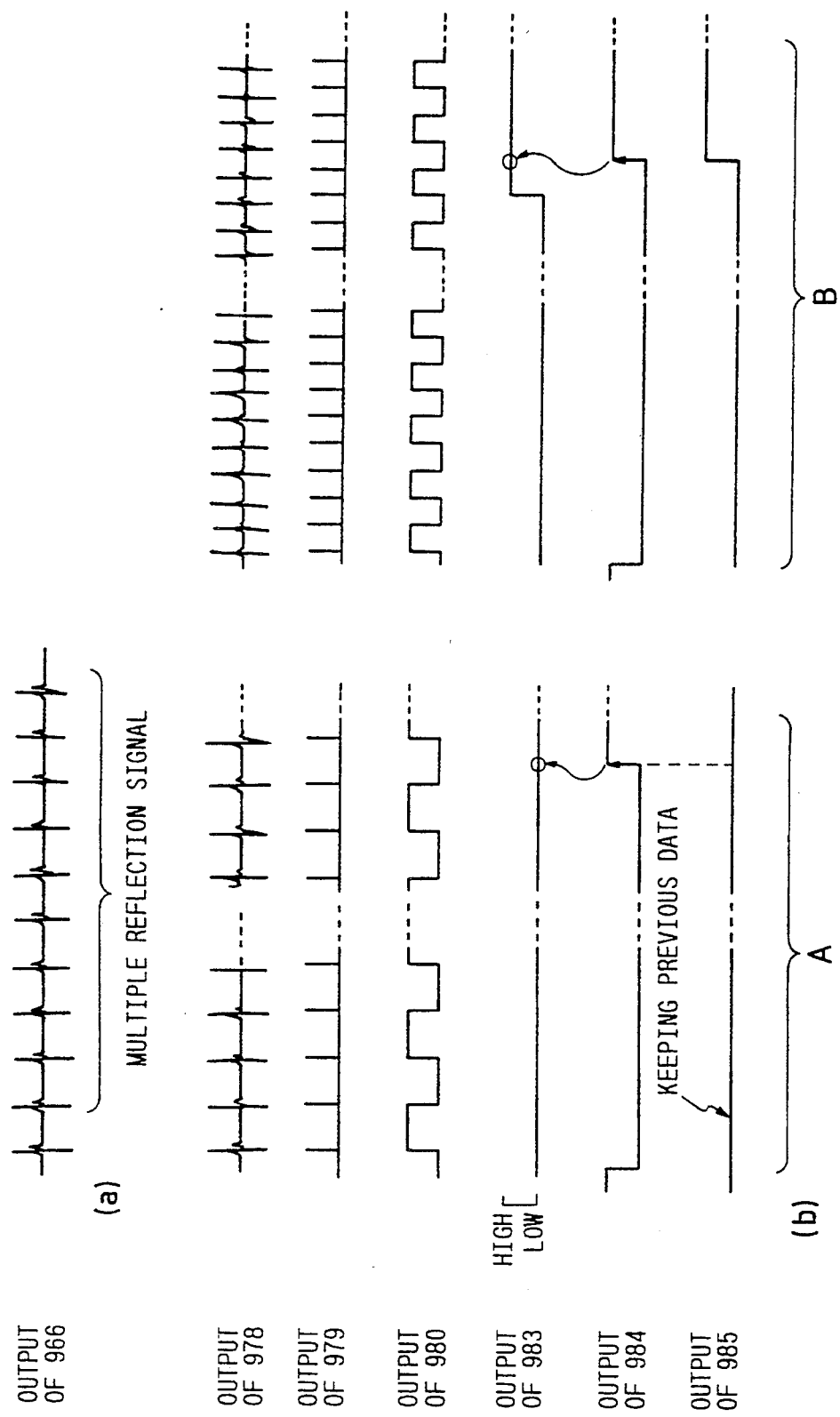
FIG. 50 shows output waveforms of the respective parts of a position detecting section of the FIG. 49 ultrasonic diagnostic apparatus.

FIG. 50 shows output waveforms of the respective parts of the position detecting section 976. As illustrated by (a) in FIG. 50, a number of multiple reflection components corresponding to the distances between the transducer holder 924 and the position sensor 966 can be obtained because the transducer holder 924 is extremely close to the position sensor 966 and the propagation medium is used which has a small attenuation characteristic. The pulse producing section 980 produces pulses on the basis of the multiple reflection signals through the output signal of the detecting section 979 as illustrated by (b) in FIG. 50. The counter section 981 counts the number of the outputs (pulses) of the pulse generating section 980 which are treated as clocks. Here, the counter section 981 is reset by the transmission electric signal due to the timing signal generating section 977. The output of the counter section 981 is always compared with a reference value of the reference value generating section 982 in the comparing section 983, for example, so as to output a low level when being below the reference value and output a high level when being above the reference value. The output of the comparing section 983 is latched in the latch section 985 in response to the reference gate signal (for example, rising) with a constant width which is generated by the reference gate generating section 984 in synchronism with the transmission electric signal due to the timing signal generating section 977. A portion (time period) indicated by A in (b) of FIG. 50 shows that the separation of the multiple reflection signal is long because the transducer holder 924 is separated from the position sensor 966, and at the time of the rising of the reference gate signal, the output of the counter section 981 is smaller as compared with the reference value generated by the reference value generating section 982, the output of the comparing section 983 becomes the low level and the output of the latch section 985 is kept to the low level. On the other hand, a portion indicated by B in (b) of FIG. 50 shows that the separation of the multiple reflection signal becomes short since the transducer holder 924 is relatively close to the position sensor 966. Before the rising of the reference gate signal, the output of the counter section 981 becomes greater than the reference value of the reference value generating section 982 and hence the output of the comparing section 983 is changed to the high level and the output of the latch section 985 is .kept to the high level. By adjusting the reference value which is the output of the reference value generating section 982 and the reference gate signal which is the output of the reference gate signal generating section 984, it is possible to know the time that the transducer holder 924 is the closest position to the position sensor 966 and it is possible to obtain the reference position of the transducer holder 924 necessary for the image formation.

As described above, the position sensor 966 is disposed at the inside of the cap 925 by the coat member 968 so as not to be brought into contact with the rear end portion of the transducer holder 924, and the pulse producing section 980 produces pulses on the basis of the multiple reflection signal, the counter section 981 counts as clocks the outputs of the pulse producing section 980, and the comparing section 983 decides the output of the counter section 981 which corresponds to the width of the gate signal generated by the reference gate signal producing section 984, whereby it is possible to accurately measure the distance between the transducer holder 924 and the position sensor 966 to form a high-accurate image without requiring a high measurement accuracy to the position sensor 966 and the position detecting section 976.

Figure 51:
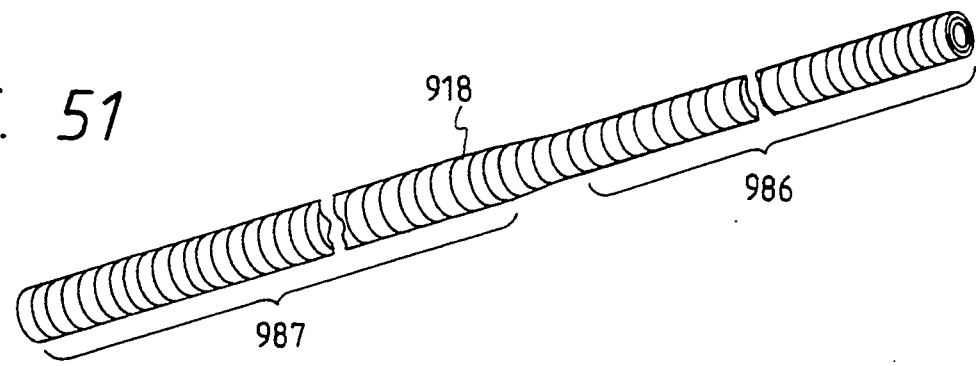
FIG. 51 shows an arrangement of a torque transmission shaft of an ultrasonic diagnostic apparatus according to a twenty seventh embodiment of this invention.
Figure 52A:
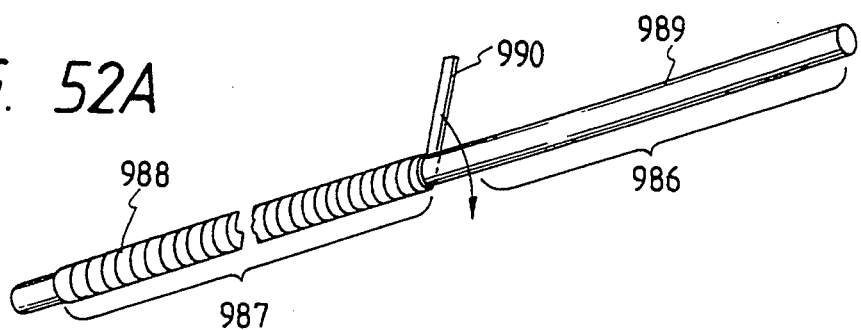
FIGS. 52A to 52C are illustrations for describing a manufacturing method of the FIG. 51 torque transmission shaft.
Figure 52B:
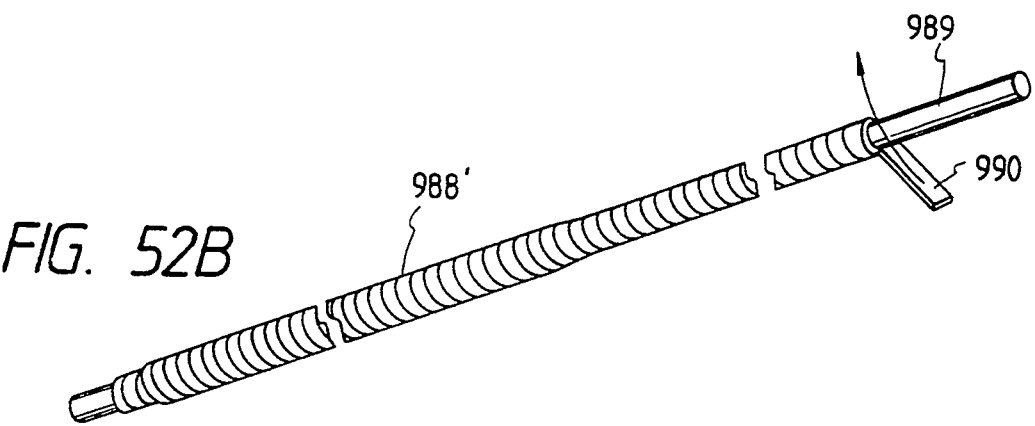
Figure 52C:
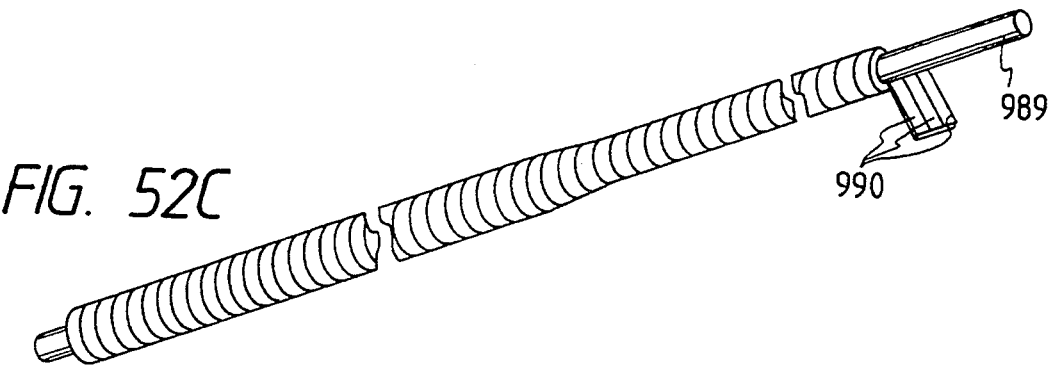

A twenty seventh embodiment of this invention will be described hereinbelow. FIG. 51 shows an arrangement of a torque transmission shaft of an ultrasonic diagnostic apparatus according to the twenty seventh embodiment of this invention. In FIG. 51, the torque transmission shaft 918 is arranged to have a multi-layered spring structure and comprises a tip portion side 986 having a length of 100 to 500 millimeters and a rear end side 987. The number of layers of the tip portion side 986 is arranged to be smaller than the number of layers of the rear end side 987. That is, at least one of the inner layers of the rear end side 987 is not provided at the tip portion side 986. This arrangement can provide an adequate flexibility to the tip portion side 986 and further provide a sufficient transferability to the rear end portion 987. FIGS. 52A to 52C are illustrations for describing a manufacturing method of the FIG. 51 torque transmission shaft 918. As illustrated in FIG. 52A, an element wire 990 is first coiled on a core member 989 to form an inner spring structure (inner layer) 988 having a length corresponding to the rear end portion 987, and further, as illustrated in FIG. 52B, a different element wire 990 is coiled in the opposite direction to be piled up on the inner spring structure to form an outer spring structure 988' having a length corresponding to the entire length of the torque transmission shaft 918 (the rear end portion 987 length + the tip portion 986 length). Finally, the core member 989 is removed therefrom. Thus, the number of the layers at the tip portion side 986 is reduced by one as compared with the rear end portion 987. The torque transmission shaft thus arranged can smoothly and stably transfer a rotating force. Here, it is also appropriate that a plurality of element wires 990 are simultaneously coiled as illustrated in FIG. 52C. This makes easy the manufacturing of the torque transmission shaft 918.

Figure 53:
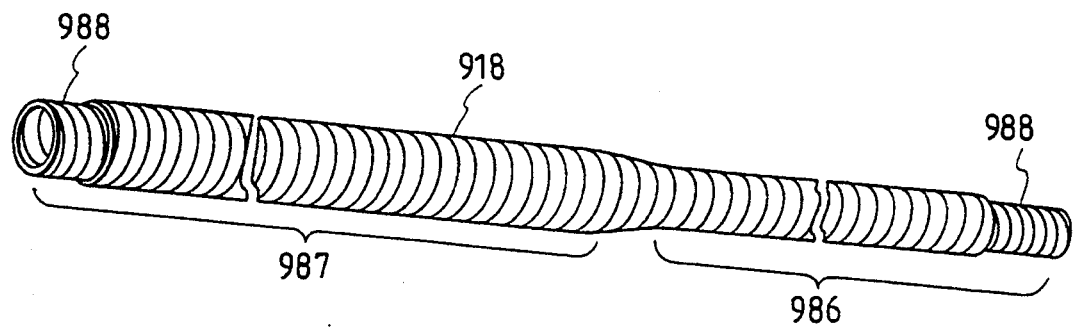
FIG. 53 shows an arrangement of a torque transmission shaft to be used in an ultrasonic diagnostic apparatus according to a twenty eighth embodiment of this invention.
Figure 54A:
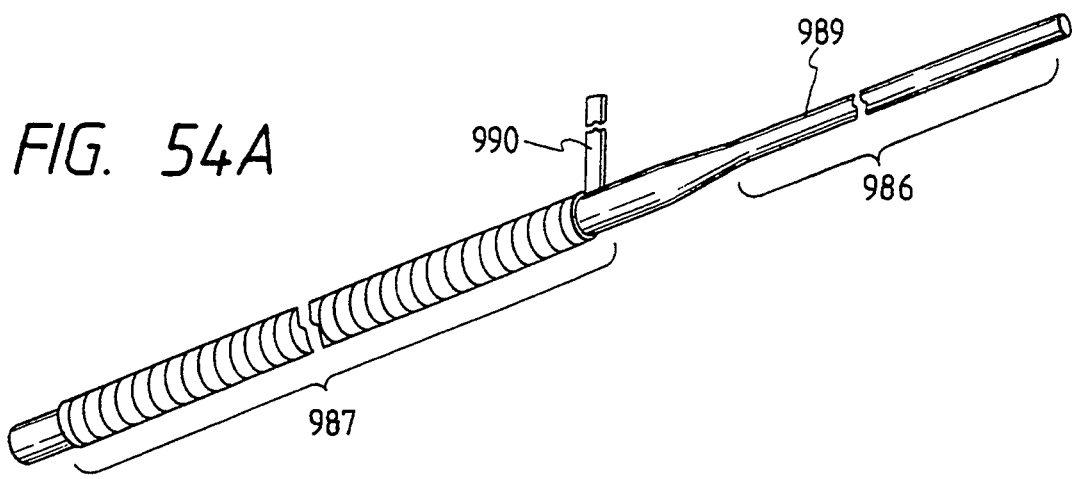
FIGS. 54A and 54B are illustrations of a manufacturing method of the FIG. 53 torque transmission shaft.
Figure 54B:
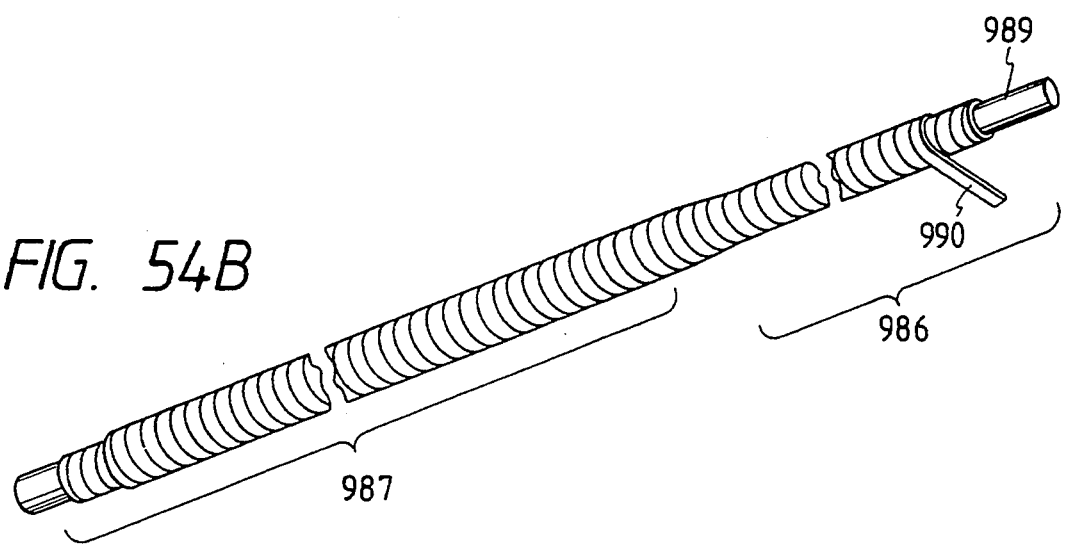

A twenty eighth embodiment of this invention will be described hereinbelow. FIG. 53 shows an arrangement of a torque transmission shaft to be used in an ultrasonic diagnostic apparatus according to the twenty eighth embodiment of this invention. Although the number of the layers of the torque transmission shaft 918 of this embodiment is equal to the number of the layers of the torque transmission shaft 918 according to the twenty seventh embodiment, the outer diameter of the tip portion side 986 is arranged to be smaller as compared with the outer diameter of the rear end portion side 987. When the number of the layers is the same and the configuration of the element wire 990 is the same, the torque transferability of the torque transmission shaft 918 depends on the diameter. Thus, the transferability of the rear end portion side 987 is more excellent as compared with the tip portion side 86. FIGS. 54A and 54B are illustrations of a manufacturing method of the FIG. 53 torque transmission shaft 918. That is, the size of a portion of the core member 989 for the rear end portion side 987 is arranged to be larger than the size of a portion of the core member 89 for the tip portion side 986, and the element wire 990 is coiled on the core member 989, thereby constructing the torque transmission shaft 918 as illustrated in FIG. 53.

Figure 55:
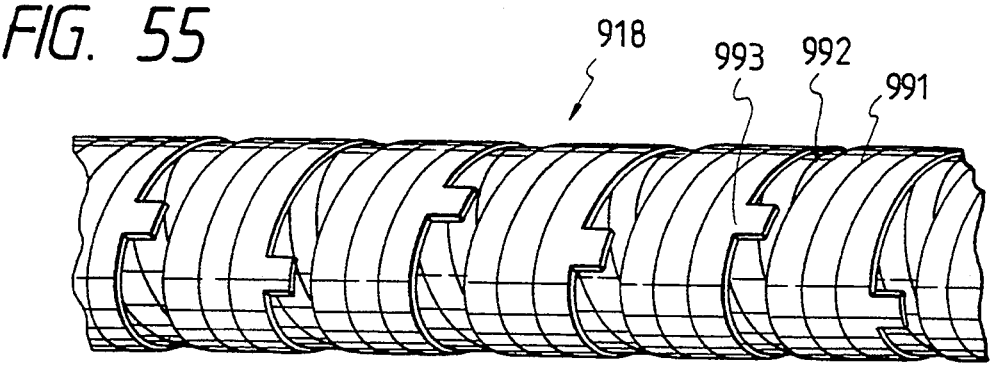
FIG. 55 is a partially enlarged illustration of a torque transmission shaft to be used in an ultrasonic diagnostic apparatus according to a twenty ninth embodiment of this invention.
Figure 56:
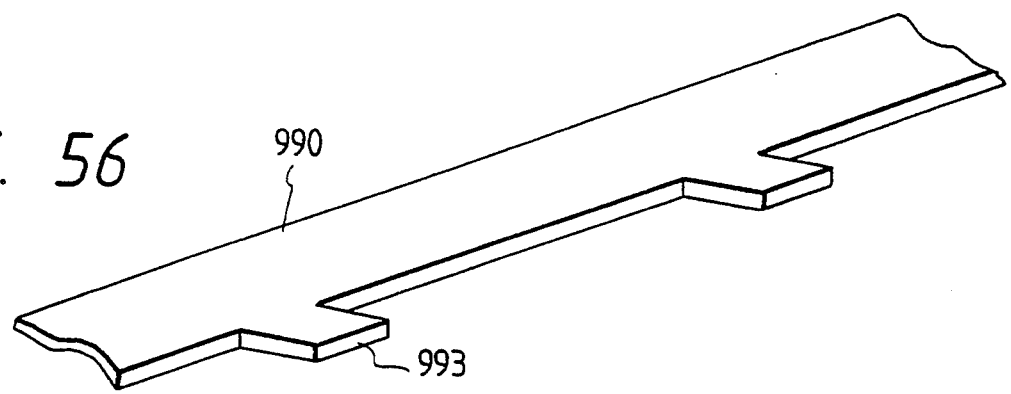
FIG. 56 is a perspective view showing an element wire to be used for the FIG. 55 torque transmission shaft.

A twenty ninth embodiment of this invention will be described hereinbelow. FIG. 55 is a partially enlarged illustration of a torque transmission shaft to be used in an ultrasonic diagnostic apparatus according to the twenty ninth embodiment of this invention. In FIG. 55, numeral 991 represents the outermost layer, 992 designates gaps and 993 depicts projecting portions. The torque transmission shaft 918 is constructed in accordance with the method as illustrated in FIG. 52C so that the gap 993 is formed between the turns. The provision of the projecting portions 993 can be achieved using an element wire having projecting portions at an equal interval as illustrated in FIG. 56. According to this arrangement, the propagation liquid (propagation medium) injected into the ultrasonic probe 901 and existing around the torque transmission shaft 918 flows in the rotating direction due to the rotation of the torque transmission shaft 918 so as to move toward the tip portion side 903 of the ultrasonic probe 901.

Figure 57A:
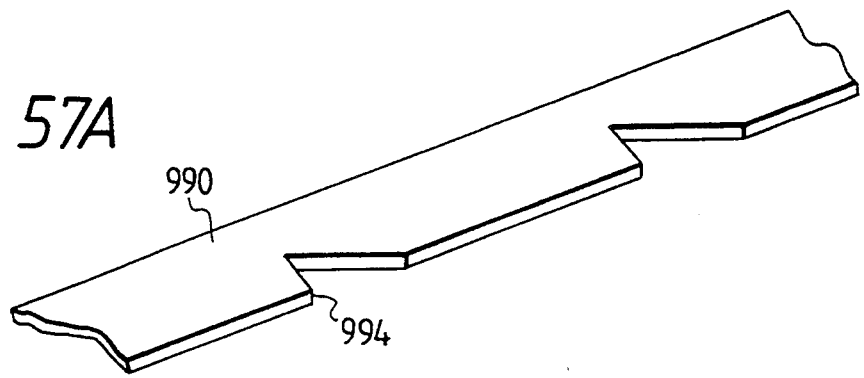
FIGS. 57A and 57B are illustrations for describing a different arrangement of the torque transmission shaft.
Figure 57B:
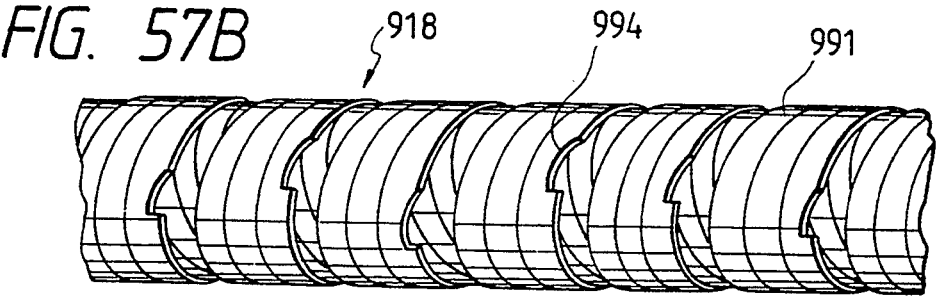

FIGS. 57A and 57B are illustrations for describing a different arrangement of the torque transmission shaft. As illustrated in FIG. 57A, notch portions 994 are formed in an element wire 990 constituting the outermost layer 991 of the torque transmission shaft 918, and as illustrated in FIG. 57B, the element wire 990 is coiled to construct the outermost layer 991. This arrangement can offer the same effect.

Figure 58:
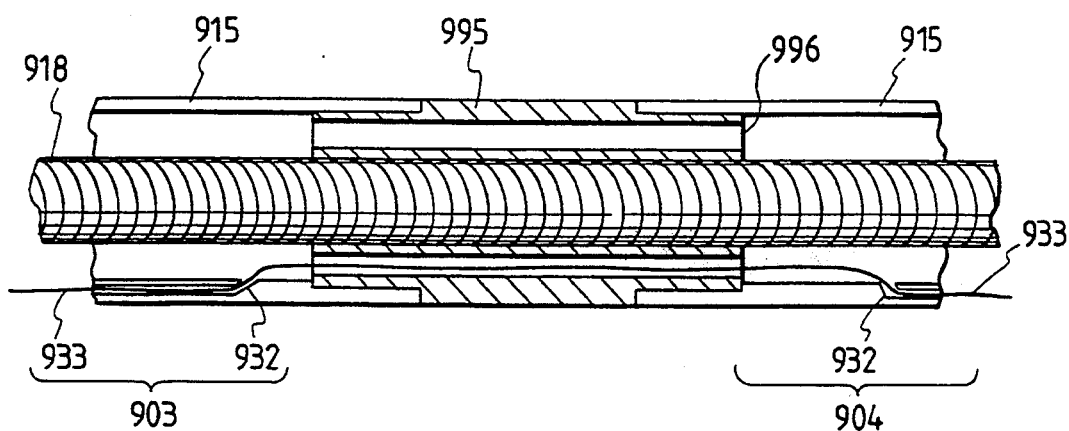
FIG. 58 is a partial cross-sectional view showing an arrangement of a torque transmission shaft to be used in an ultrasonic diagnostic apparatus according to a thirtieth embodiment of this invention.

A thirtieth embodiment of this invention will be described hereinbelow. FIG. 58 is a partial cross-sectional view showing an arrangement of a torque transmission shaft to be used in an ultrasonic diagnostic apparatus according to the thirtieth embodiment of this invention. In FIG. 58, numeral 915 represents a catheter, 918 designates a torque transmission shaft, 932 depicts a plurality of lumens provided in the catheter 915, 933 denotes a signal line which is inserted into the lumen 932 and which is for the electric connection between the forward direction ultrasonic transducer 918 and the forward direction transmission sand reception section 908, 995 indicates a cylindrical intermediate bearing, and 996 represents a plurality of microlumens provided in the intermediate bearing 995. The intermediate bearing 995 is made of a material such as a fluorine having a small frictional coefficient and fixedly provided between a tip portion side of the catheter 915 and a rear end portion side of the catheter 915. The signal line 933 passes through the lumen 932 of the catheter 915 of the rear end portion side 904 to reach the inner space of the catheter 915 at the vicinity of the intermediate bearing 995 and then passes through the lumen 996 of the intermediate bearing 995 to reach the inner space of the catheter 915 and further passes through the lumen 932 of the catheter 915 of the tip portion side 903. Further, the other lumens 996 are used as passages for the propagation medium whereby the propagation is lead to the tip portion side 903.

The quality of the ultrasonic image depends on the stability of the rotation of the torque transmission shaft 918. As one of the factors for lowing the stability of the rotation of the torque transmission shaft 918 there is the twisting or vibration of the torque transmission shaft 918 which occurs in the space portion between the catheter 915 and the torque transmission shaft 918. Thus, the twisting or vibration of the torque transmission shaft 918 can be reduced by reducing the space therebetween. However, in this case it is to be noted that the rotational stability is deteriorated due to the friction between the outer surface of the torque transmission shaft 918 and the inner surface of the catheter 915. This embodiment is constructed by taking into account this fact.

According to the torque transmission shaft thus arranged, the intermediate bearing 995 which is provided at the intermediate portion of the ultrasonic probe 901 and into which the torque transmission shaft 918 is inserted can suppress the twisting or vibration of the torque transmission shaft 918 concurrently with stably transferring the rotating force due to the drive section 905.

Figure 59:
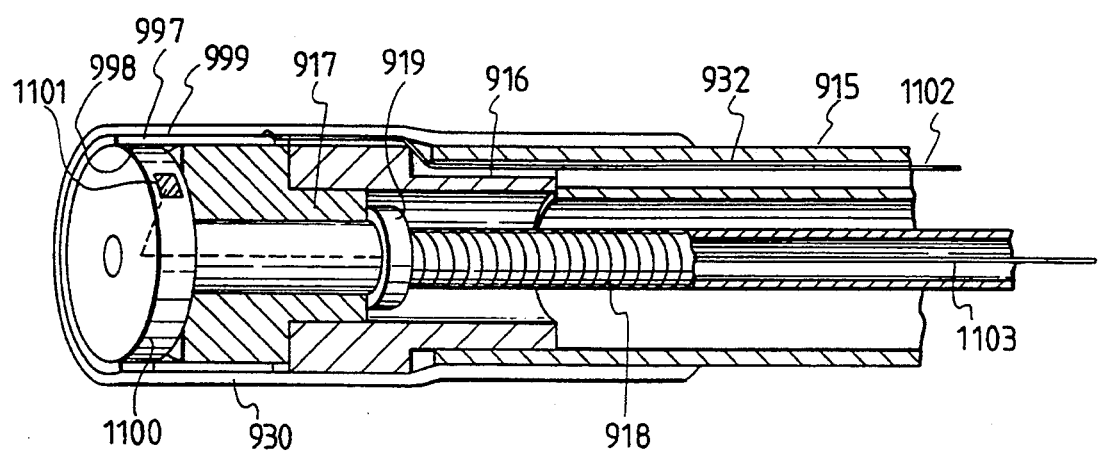
FIG. 59 is a cross-sectional view showing an arrangement of a tip portion of an ultrasonic probe of an ultrasonic diagnostic apparatus according to a thirty first embodiment of this invention.

A thirty first embodiment of this invention will be described hereinbelow. FIG. 59 is a cross-sectional view showing an arrangement of a tip portion of an ultrasonic probe of an ultrasonic diagnostic apparatus according to the thirty first embodiment of this invention. In FIG. 59, numeral 915 represents a catheter, 932 designates a lumen formed in the catheter 915, 916 depicts a shaft having a hollow structure and connected to the tip portion of the catheter 915, 917 denotes a bearing having an hollow structure and inserted into the hollow portion of the shaft 916, 918 indicates a torque transmission shaft for transferring the rotating force due to the drive section 905 to the tip portion of the ultrasonic probe 901, 919 is a rotating shaft fixed to the tip portion of the torque transmission shaft 918, 997 represents a high-polymer piezoelectric film provided at the tip portion of the ultrasonic probe 901, 998 designates a plurality of rectangular inside electrodes provided at the inside of the high-polymer piezoelectric film 997, 999 is an outside electrode provided at the outside of the high-polymer piezoelectric film 997, 1100 depicts a disc-like electrode connected to the rotating shaft 919 and made of an insulating material., 1101 depicts a conductive electrode provided at a portion of the side surface of the disc-like electrode 1100, 930 denotes a protective coat for covering the tip portion 903 of the ultrasonic probe 901, 102 is a signal line connected to the outside electrode 999, and 1103 is a signal line connected to the electrode 1101 and inserted from the inside of the disc-like electrode 1100 into the torque transmission shaft 918 and electrically connected to the main body 902.

Figure 60:
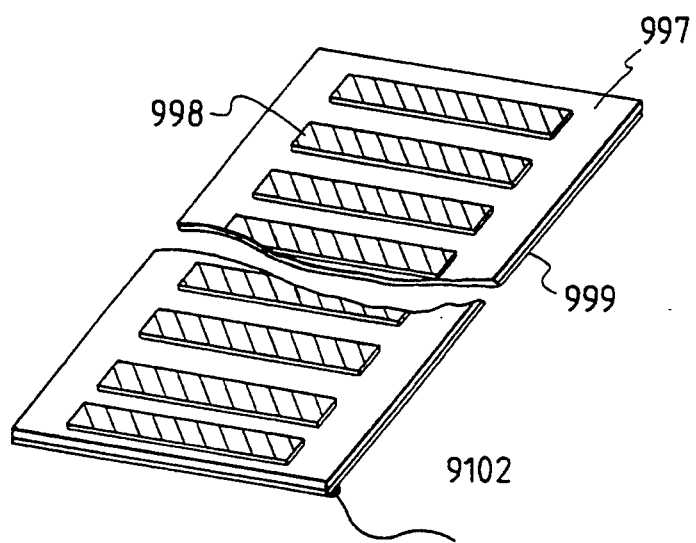
FIG. 60 shows an arrangement of a high-polymer piezoelectric film on the thirty first embodiment.
Figure 61:
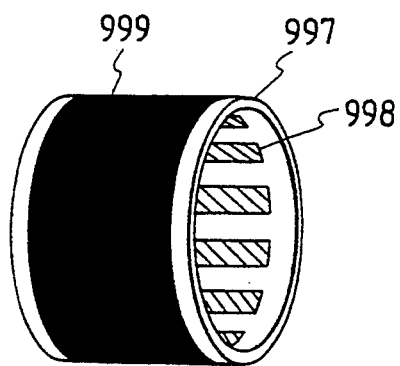
FIG. 61 is an illustration of an ultrasonic transducer to be constructed with the FIG. 60 high-polymer piezoelectric film.

FIG. 60 shows an arrangement of the high-polymer piezoelectric film 997. The high-polymer piezoelectric film 997 is constructed by polarization-processing a ferroelectric high polymer material such as polyvinylidene fluoride (PVDF) and a PVDF copolymer such as P(VDF-TrFe) to provide a piezoelectric characteristic. The outside electrode 999 is provided on one surface of the high-polymer piezoelectric film 997 by means of the sputter or deposition. On the other hand, on the other surface thereof there is provided the plurality of rectangular inside electrodes 998. Generally, the high-polymer piezoelectric film 997 has an excellent high-frequency characteristic. It is appropriate that the polarization process is effected with respect to the inside electrodes 998 and the outside electrode 999, or an electrode is provided on the inside electrode 998 surface and polarization-processed and then removed so as to construct the plurality of rectangular inside electrodes 998. This high-polymer piezoelectric film 997 is rounded as illustrated in FIG. 61 and disposed as the ultrasonic transducer at the tip portion side 903 of the ultrasonic probe 901.

FIG. 62 is an enlarged illustration of the disc-like electrode 1100. As illustrated in FIG. 62, the signal line 1103 is provided at the inside of the rotating shaft 919 and extends within the disc-like electrode 1100 to be electrically connected to the back surface of the electrode 1101. The disc-like electrode 1100 is disposed at the inside of the tip portion side 903 of the ultrasonic probe 901 so that its circumferential surface comes into contact with the inside electrode 998.

In operation, the torque transmission shaft 918 is rotated due to the rotating force generated by the drive section 905 and hence the rotating shaft 919 is rotated with respect to the bearing 917, and the disc-like electrode 1100 fixed to the tip portion of the rotating shaft 919 comes into contact with the inside electrodes 998 and rotated. The control section 913 of the main body 902 obtains, on the basis of the output of the position detecting section 941, the timing at which the electrode 1101 provided on the disc-like electrode 1100 just comes into contact with one of the inside electrodes 998 and causes the peripheral direction transmission and reception section 906 to generate the transmission electric signal with respect to the signal lines 1102 and 1103. Due to the characteristic of the high-polymer piezoelectric film 997 in which the lateral connection is weak, only the area interposed between the outside electrode 999 and the inside electrode 998 electrically connected through the electrode 1101 to the peripheral direction transmission and reception section 906 converts the transmission electric signal into an ultrasonic wave which in turn propagates within the object. The reflected ultrasonic waves are received at the time difference corresponding to the positional relation between various reflectors. The reflection signal is processed to be displayed on the monitor 911 as described above.

Here, the inside electrode 998 is weak in strength and the disc-like electrode 1100 is brought into contact with the inside electrode 998 in the state that it is rotating, and hence there is the possibility that the inside electrode 998 is removed. Thus, it is appropriate that, as illustrated in FIG. 63, a ring-like electrode 1104 is used so that the disc-like electrode 1100 is indirectly brought into contact with the inside electrode 998. In FIG. 63, the ring-like electrode 1104 is composed of insulating portions 1105, for example, made of a resin and conductive portions 1106 positioned in correspondence with the width or the interval of the inside electrodes 998 and, for example, made of a metal. The conductive portion 1106 is constructed to extends from the front surface of the insulating portion 1105 to the rear surface thereof. The high-polymer piezoelectric film 997 is provided so that the conductive portions 1106 are coincident in position with the inside electrodes 998. The disc-like electrode 1100 is brought into contact with the inside of the ring-like electrode 1104 and rotated.

Further, a thirty second embodiment of this invention will be described hereinbelow. FIG. 64A shows an arrangement of a disc-like electrode of an ultrasonic probe to be used for an ultrasonic diagnostic apparatus according to the thirty second embodiment of this invention. In FIG. 64A, numeral 1107 represents a disc-like electrode having the same function as the disc-like electrode in the aforementioned embodiment, 1108 designates a plurality of electrodes successively arranged on a portion of the circumferential surface of the disc-like electrode 1107 at a pitch indicated by 1109, 1103 depicts a signal line electrically connected to the electrode 1107. The other parts are the same as those in FIG. 62. The pitch 1109 corresponds to the interval between the inside electrodes 998 shown in FIG. 60. FIG. 64B is a block diagram showing an electric connection between the electrodes 1108 of the disc-like electrode 1107 and the signal line 1103. By taking into account the positions of the electrodes 1108 provided on the disc-like electrode 1107, the electrodes 1108 and the signal line 1103 are connected to each other through delay devices 1110 for focusing to a desired position the ultrasonic wave from the high-polymer piezoelectric film 997 relating to the plurality of the electrodes 1108 (so-called phased array method). In detail, the delay amount of the delay device 1110 connected to the central electrode 1108 of the plurality of the electrodes 1108 successively arranged is arranged to be greater as compared with the others delay devices. These delay devices 1110 are provided within the disc-like electrodes 1107. In FIGS. 64A and 64B three electrodes 1108 are illustrated, and in this case, one delay device 1110 is connected to only the electrode 1108 disposed at the central position. With this arrangement, the ultrasonic wave from the high-polymer piezoelectric film 997 is focused on a position determined in accordance with the delay device 1110.

According to this embodiment, the disc-like electrode 1107 connected to the rotating shaft 919 and the high-polymer piezoelectric film 997 having a plurality of rectangular inside electrodes 998 are provided and the electrodes 1108 are provided on the disc-like electrode 1107 to have a pitch corresponding to the interval of the inside electrodes 998, and the plurality of inside electrodes 998 are driven to focus the ultrasonic wave on the position due to the delay device 1110 and perform the scanning operation in the peripheral direction. Thus, it is possible to obtain the peripheral direction ultrasonic image with a high resolution due to the focusing effect without injecting the propagation medium into the inside of the ultrasonic probe 901.

Figure 65:
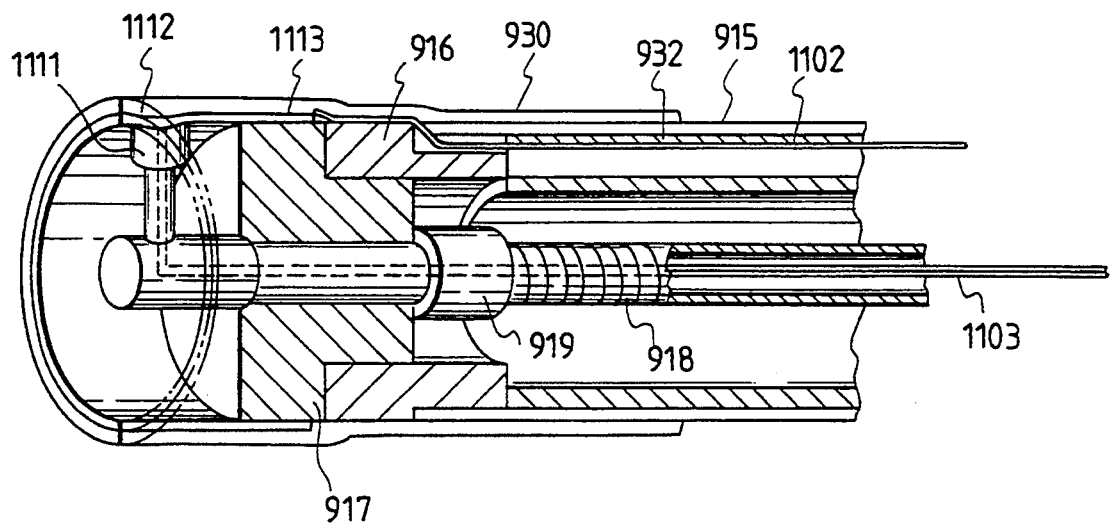
FIG. 65 is a cross-sectional view showing an arrangement of a tip portion of an ultrasonic probe of an ultrasonic diagnostic apparatus according to a thirty third embodiment of this invention.

Moreover, a thirty third embodiment of this invention will be described hereinbelow. FIG. 65 is a cross-sectional view showing an arrangement of a tip portion of an ultrasonic probe of an ultrasonic diagnostic apparatus according to the thirty third embodiment of this invention. In FIG. 65, numeral 915 represents a catheter, 932 designates a lumen formed in the catheter 915, 916 depicts a shaft having and hollow structure and fixed to the tip portion side of the catheter 915, 917 denotes a bearing having a hollow structure and inserted into the hollow portion of the shaft 916, 918 indicates a torque transmission shaft for transferring the rotating force due to the drive section 906 to the tip portion side of the ultrasonic probe 901, 919 is a rotating shaft fixed to the tip portion side of the torque transmission shaft 918, and 1111 represents a rotating electrode portion fixed to the tip portion side of the rotating shaft 919. The rotating electrode portion 1111 has a flat or concave surface configuration and directs toward the circumference of the ultrasonic probe 901 (in the peripheral direction). Further, numeral 1112 represents a high-polymer piezoelectric film provided at the circumferential portion of the tip portion of the ultrasonic probe 901, 1113 designates an electrode provided at the outside of the high-polymer piezoelectric film 1112, 930 depicts a protective coat for covering the tip portion side 903 of the ultrasonic probe 901, 1102 is a signal line inserted into the lumen 932 and connected to the electrode 1113, and 1103 represents connected to the rotating electrode portion 1111 and inserted into the hollow portions of the rotating shaft 919 and the torque transmission shaft 918.

Figure 66:
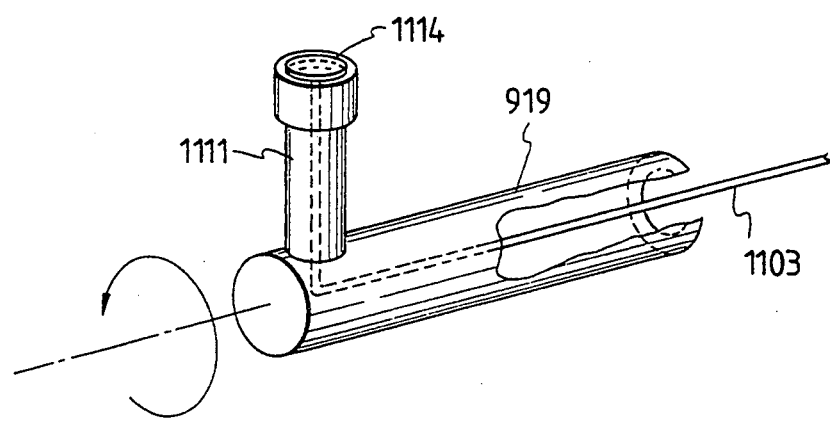
FIG. 66 is a perspective view showing the arrangement of a rotatable electrode portion of the FIG. 65 ultrasonic probe.

FIG. 66 is a perspective view showing the arrangement of the rotating electrode portion 1111. The surface 1114 of the rotating electrode portion 1111 is arranged to have a flat or concave configuration, and the surface 1114 portion or the entire rotating electrode portion 1111 is made of a conductive material and connected to the signal line 1103. In the case that the surface 1114 is arranged to have a concave configuration, the ultrasonic wave from the high-polymer piezoelectric film 1112 is focused on the position within the object which is determined in accordance with the configuration. It is appropriate that the rotating electrode portion 1111 is made of a material having a characteristic to function as a backing load material for the high-polymer piezoelectric film 1112.

Figure 67:
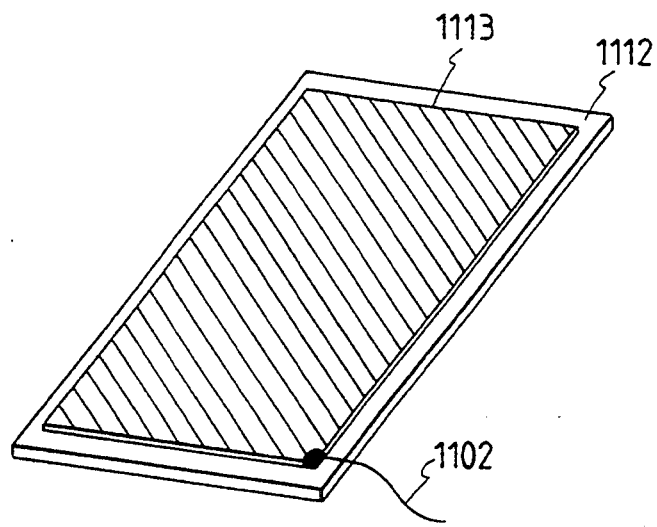
FIG. 67 shows an arrangement of a high-polymer piezoelectric film of the FIG. 65 ultrasonic probe.

FIG. 67 shows an arrangement of the high-polymer piezoelectric film 1112. The high-polymer piezoelectric film 1112 is constructed by polarization-processing a ferroelectric high polymer material such as polyvinylidene fluoride (PVDF) and a PVDF copolymer such as P(VDF-TrFe) to provide a piezoelectric characteristic. On one surface of the high-polymer piezoelectric film 1112 there is provided the electrode 1113. In the polarization process for the high-polymer piezoelectric film 1112, an electrode is provided on a surface opposite to the surface on which the electrode 1113 is disposed and removed after the completion of the polarization process. The high-polymer piezoelectric film 1112 is rounded to form a cylindrical configuration so that the electrode 1113 is positioned at the outer side of the cylindrical configuration, and disposed at the tip portion side 903 of the ultrasonic probe 901.

In operation, the rotating force due to the drive section 905 rotates the torque transmission shaft 918 and further rotates the rotating shaft 919 with respect to the bearing 917. The rotating electrode portion 1111 fixedly connected to the rotating shaft 919 is rotated in the state that its surface 1114 comes into contact with the high-polymer piezoelectric film 1112. During this rotating operation, the peripheral direction transmission and reception section 906 generates the transmission electric signal with respect to the signal lines 1102 and 1103. Only the area interposed between the electrode 1113 and the surface 1114 of the rotating electrode portion 1111 which is the contact surface with the high-polymer piezoelectric film 1112 transmits an ultrasonic wave in response to the transmission electric signal. According to this embodiment, it is possible to obtain a peripheral direction ultrasonic image with a high resolution without injecting the propagation medium into the ultrasonic probe 901.

Further a description will be made hereinbelow in terms of a thirty fourth embodiment of this invention.

Figure 68:
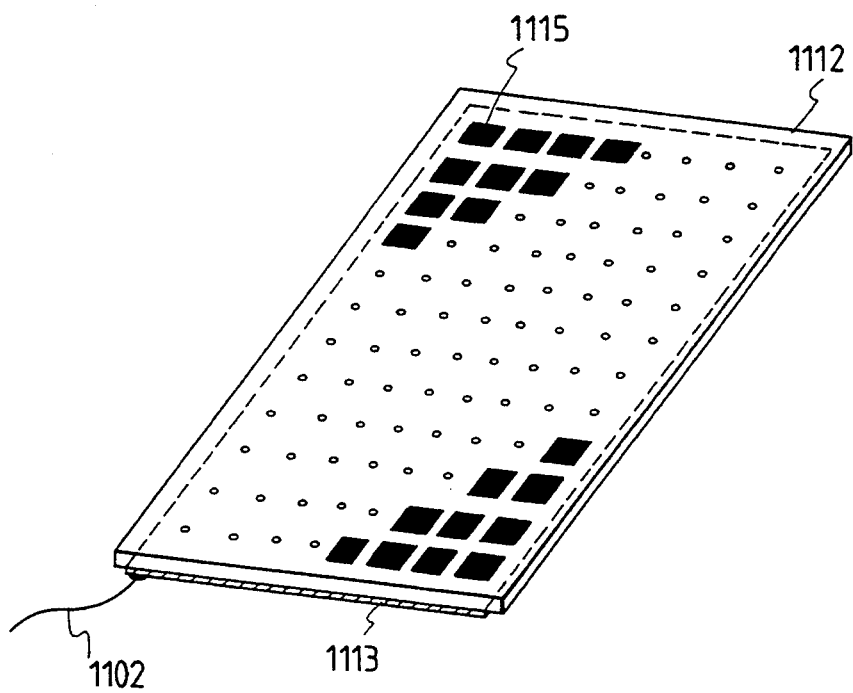
FIG. 68 is a perspective view showing an arrangement of a high-polymer piezoelectric film of an ultrasonic probe of an ultrasonic diagnostic apparatus according to a thirty fourth embodiment of this invention.

FIG. 68 is a perspective view showing an arrangement of a high-polymer piezoelectric film of an ultrasonic probe of an ultrasonic diagnostic apparatus according to the thirty fourth embodiment of this invention. The other arrangements are the same as the aforementioned embodiment. In FIG. 68, numeral 1112 represents a high-polymer piezoelectric film, 1113 designates an electrode provided on one surface of the high-polymer piezoelectric film 1112, and 1115 denotes a plurality of microelectrodes which are electrically insulated from each other. Each of the microelectrodes 1115 has an area extremely smaller than the surface 1114 of the rotating electrode portion 1111. Further, the microelectrodes 1115 are arranged to have rectangular configurations whereby the rate of the total area of the microelectrodes 1115 to the surface of the high-polymer piezoelectric film 1112 becomes great. After the polarization process, the microelectrodes 1115 may be constructed by using a mask. According to this embodiment, it is possible to reduce the contact resistance between the high-polymer piezoelectric film 1112 and the surface 1114 of the rotatable electrode portion 1111, thereby effectively inputting the electric energy to the high-polymer piezoelectric film 1112.

Figure 69:
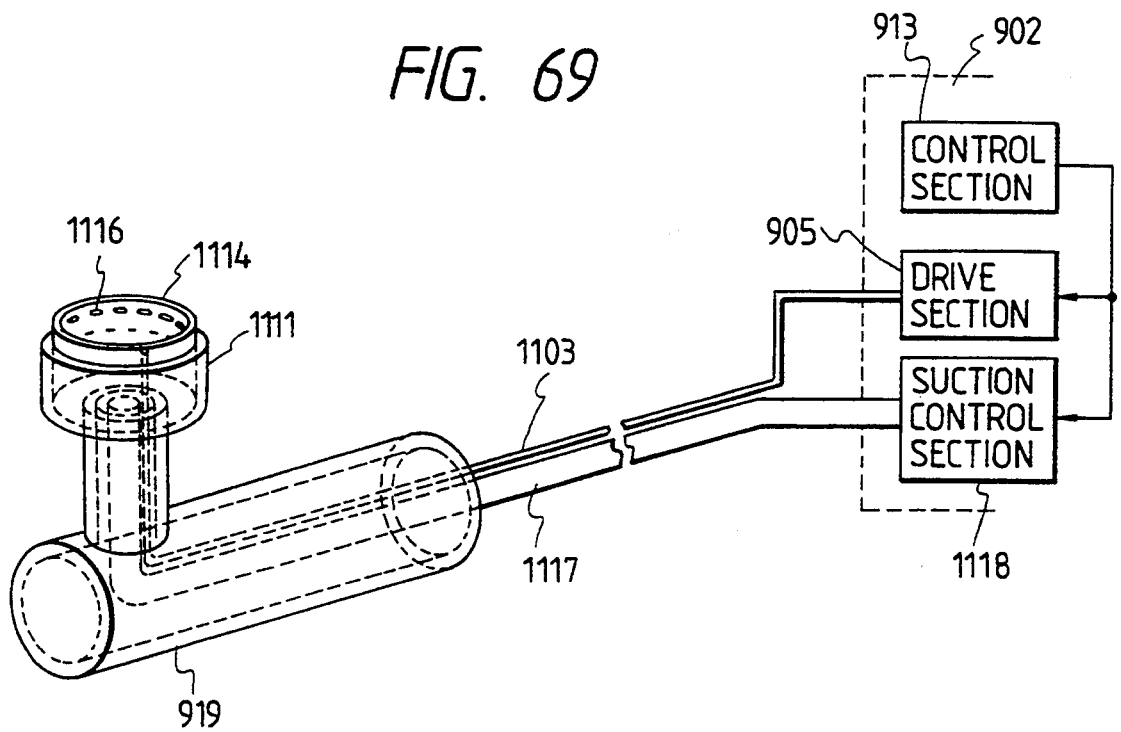
FIG. 69 shows a rotatable electrode portion of an ultrasonic probe of an ultrasonic diagnostic apparatus according to a thirty fifth embodiment of this invention.

Further, a description will be described hereinbelow in terms of a thirty fifth embodiment of this invention. FIG. 69 shows a rotating electrode portion of an ultrasonic probe of an ultrasonic diagnostic apparatus according to the thirty fifth embodiment of this invention. In FIG. 69, numeral 1111 represents a rotating electrode portion, 1103 designates a signal line connected to the rotating electrode portion 1111, 1114 depicts is a surface of the rotating electrode portion 1111 which is the contact surface with the high-polymer piezoelectric film 1112, and 1116 denotes a plurality of microholes formed in the surface 1114 and united together within the rotating electrode portion 1111. Further, 1117 represents a micropipe coupled to the microholes 1116 united within the rotating electrode portion 111, and 1118 designates a suction control section provided in the main body 902 and connected to the micropipe 1117.

In operation, during the rotating operation of the rotating electrode portion 1111, the suction control section 1118 performs a suction operation through the micropipe 1117. Due to this suction operation, the microholes 1116 connected to the micropipe 1117 lightly draw the high-polymer piezoelectric film 1112 so that the adhesion between the surface 1114 and the high-polymer piezoelectric film 1112 is improved. According to this embodiment, it is possible to reduce the contact resistance concurrently improving the adhesion therebetween, and hence it is possible to effectively input the electric signal from the rotating electrode portion 1111 to the high-polymer piezoelectric film 1112.

Figure 70:
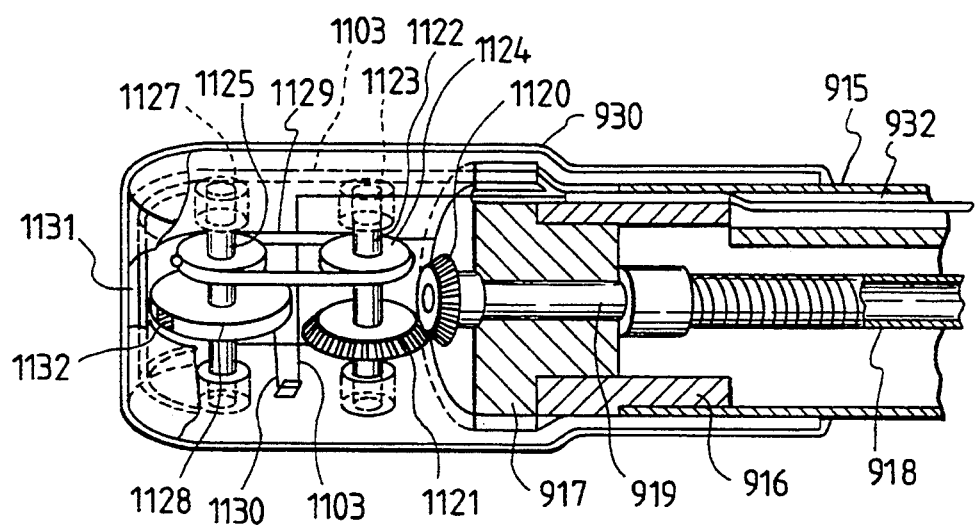
FIG. 70 is a cross-sectional view showing an arrangement of a tip portion of an ultrasonic probe of an ultrasonic diagnostic apparatus according to a thirty sixth embodiment of this invention.

Moreover, a description will be made hereinbelow in terms of a thirty sixth embodiment of this invention. FIG. 70 is a cross-sectional view showing an arrangement of the tip portion 903 of an ultrasonic probe 901 of an ultrasonic diagnostic apparatus according to the thirty sixth embodiment of this invention. In FIG. 70, numeral 915 represents a catheter made of a high-polymer material and arranged to have a flexible hollow structure, 932 designates a lumen formed in the catheter 915, 916 depicts a shaft fixed to the tip portion side of the catheter 915, 917 denotes a bearing fixed to the shaft 916, 918 indicates a flexible torque transmission shaft for transferring the rotating force of the drive section 905 to the tip portion side 903 of the ultrasonic probe 901, and 919 is a rotating shaft fixed to the torque transmission shaft 918 and inserted into the bearing 917. Further, numeral 1119 represents a cap fixed to the tip portion side of the bearing 917, 1120 designates a first bevel gear fixed to the rotating shaft 919, 1121 depicts a second bevel gear engaged with the first bevel gear 1120, 1122 denotes a rotating shaft which is the central shaft of the second bevel gear 121, and 123 indicates two bearings for the rotating shaft 1122 which are provided at the inside of the cap 925. Still further, numeral 1124 is a first pulley provided on the rotating shaft 1122, 1125 represents a rotating shaft, 1126 designates a pulley provided on the rotating shaft 1125, 1127 depicts two bearings for the rotating shaft 1126 which are disposed at the inside of the cap 925, 1128 denotes a rotating electrode portion disposed on the center portion of the rotating shaft 1125, 1129 indicates a drive belt for transferring the rotation of the pulley 1124 to the pulley 1126, and 1130 is a blush made of a conductive material and brought into contact with a ring-like electrode 1133 provided on the rotating electrode portion 1128. Moreover, numeral 113 1 is an ultrasonic transducer made of a high-polymer piezoelectric material and having a structure as illustrated in FIGS. 67 and 68, and 930 is a protective coat for covering the tip portion side 903 of the ultrasonic probe 901. The electrode 1113 of the ultrasonic transducer 1131 is disposed to face the outside. the signal line 1102 is connected to the electrode 1113 and the signal line 1103 is connected to the brush 1139.

Figure 71:
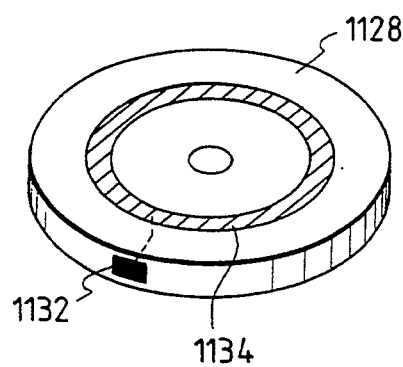
FIG. 71 is a perspective view showing an arrangement of a rotatable portion of the FIG. 70 ultrasonic probe.
Figure 72:
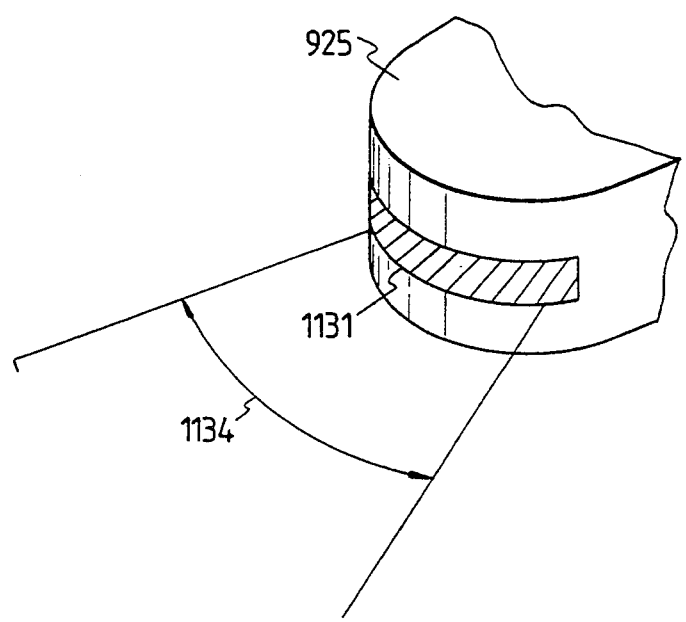
FIG. 72 is a perspective view showing a tip portion of the FIG. 70 ultrasonic probe.

FIG. 71 is a perspective view showing an arrangement of a rotatable portion 1128. The rotating electrode portion 1128 is made of an insulating material, and on a portion of the circumferential surface thereof there is provided a conductive electrode 1132. Further, on a side surface of the rotating electrode portion 1128 there is provided a circular ring-like electrode 1133. Within the rotating electrode portion 1128, the electrode 1132 and the ring-like electrode 1135 are connected to each other. The ring-like electrode 1133 always comes into contact with the brush 1130 during the rotation of the rotating electrode portion 1128 and acts as the so-called slip ring to cause the signal line 1103 to be connected to the electrode 1132 without being twisted. According to this embodiment, the rotating direction of the rotating electrode portion 111 in the above-described embodiment is arranged to be changed by 90° so as to allow the forward direction scanning. As illustrated in FIG. 72, the cap 925 is configured so as not to obstruct the operation of the rotating electrode portion 1128.

In operation, due to the rotating force of the drive section 905, the torque transmission shaft 918, rotating shaft 919 and bevel gear 1120 are rotated. Due to the rotation of the bevel gear 1120, the bevel gear 1121, rotating shaft 1122 and pulley 1124 are rotated. Here, it is appropriate that the engaging portion between the bevel gears 1120 and 1121 is made of a rubber material to provide a great friction. The rotation of the pulley 1124 rotates, through the drive belt 1129, the pulley 1126, rotating shaft 1125 and rotating electrode portion 1128. The electrode 1132 on the rotating electrode portion 1128 comes into contact with the back surface of the ultrasonic transducer 1131. During these operations, the main body section 902 performs the transmission and reception of an ultrasonic wave in a manner as described above, and hence an ultrasonic image corresponding to a sectral scanning area indicated by numeral 1134 in FIG. 72 is formed on the basis of the forward direction reflection signal of the reflection signals due to the rotation of the rotating electrode portion 1128 to be displayed on the monitor 911.

Figure 73A:
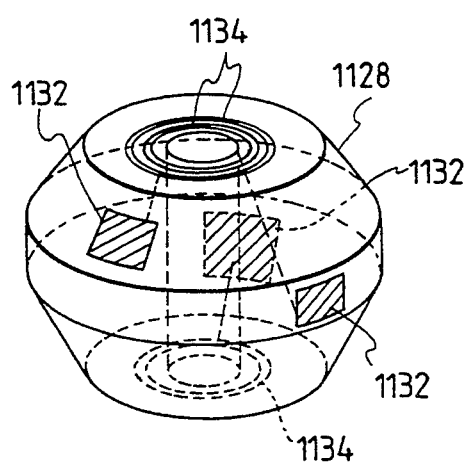
FIG. 73A shows a different arrangement of the rotatable electrode portion.
Figure 73B:
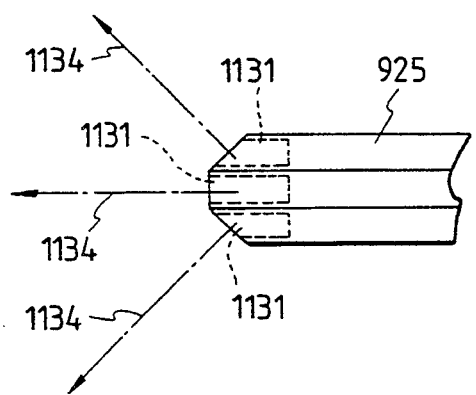
FIG. 73B shows a scanning state of the FIG. 73A rotatable electrode portion.

FIG. 73A shows a different arrangement of the rotating electrode portion 1128. The plurality of electrodes 1132 are disposed at different circumferential surfaces in different directions with respect to the central axis. For example, as illustrated in FIG. 73A, three electrodes 1132 are disposed at an angular interval of 120°. The three ring-like electrodes 1133 for the three electrodes 1132 are disposed at one side surface or both side surfaces. With the three electrodes 1132 being successively switched and the ultrasonic wave transmission reception operation being effected, as illustrated in FIG. 73B, the sectral scanning operation is effected with respect to a plurality of areas (directions) 1134 at different angles. Since the electrodes 1132 are disposed in different directions with respect to the central axis, the ultrasonic wave transmission and reception operation can be effected in sequence. In addition, it is possible to prevent the reception of the ultrasonic reflection signal due to the other electrode. According to this embodiment, it is possible to obtain an ultrasonic image with a high resolution without injecting the propagation medium into the ultrasonic probe 901.

Figure 74:
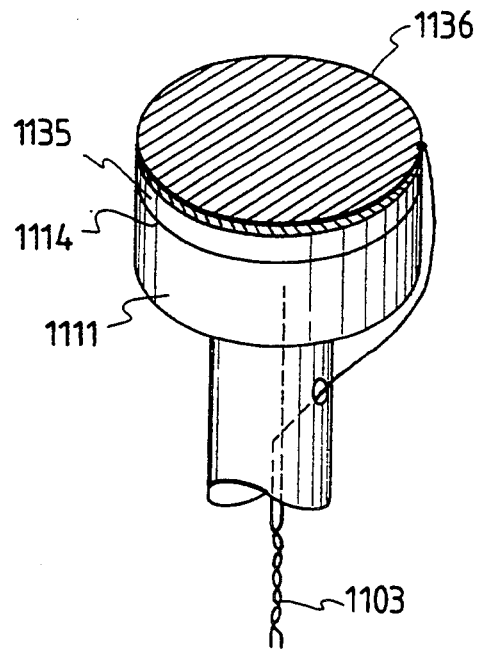
FIG. 74 shows a rotatable electrode portion of an ultrasonic probe to be used in an ultrasonic diagnostic apparatus according to a thirty seventh embodiment of this invention.
Figure 75:
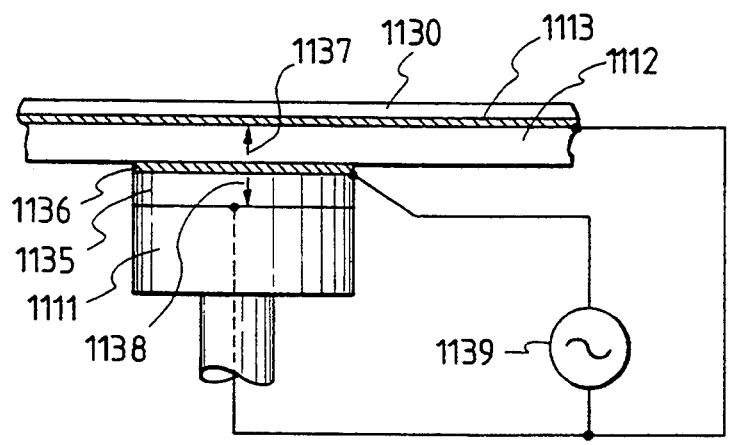
FIG. 75 shows an electric connection between a rotating electrode portion and a high-polymer piezoelectric film in the FIG. 74 ultrasonic probe.

In addition, a description will be described hereinbelow in terms of a thirty seventh embodiment of this invention. FIG. 74 shows a rotating electrode portion of an ultrasonic probe to be used in an ultrasonic diagnostic apparatus according to the thirty seventh embodiment of this invention. In FIG. 74, numeral 1111 represents a rotating electrode portion, 1114 designates a surface of the rotating electrode 1111, 1135 depicts a high-polymer piezoelectric film provided on the surface 1114, and 1136 is an electrode provided on the high-polymer piezoelectric film 1135. FIG. 75 shows an electric connection between the rotating electrode portion and a high-polymer piezoelectric film. In FIG. 75, numeral 1112 represents a high-polymer piezoelectric film, 1113 designates an electrode provided at the outer surface of the high-polymer piezoelectric film 1112, 1137 represents an arrow indicating the polarization direction of the high-polymer piezoelectric film 1112, 1138 depicts an arrow indicating the polarization direction of the high-polymer piezoelectric film 1135, 1139 denotes a drive circuit, 930 is a protective coat. It is appropriate that microelectrodes 1115 as illustrated in FIG. 68 are provided at a surface of the high-polymer piezoelectric film 1112 which is the opposite to the surface facing the electrode 1113. The electrode 1113 and the surface 1114 of the rotating electrode portion 1111 are electrically connected to each other and connected to one terminal of the drive circuit 1139. The other terminal of the drive circuit 1139 is connected to the electrode 1136.

Generally, the frequency-lowering or area-reducing of a high-polymer piezoelectric film causes increase in the electric impedance so as to obstruct an effective energy supply because of non-matching with respect to the impedance of the drive circuit 1139, thereby deteriorating the quality of the ultrasonic image. The ultrasonic probe according to this invention is arranged to be inserted into a narrow object such as a coronary artery, and hence the rotating electrode portion 1111 is limited to have a small area. According to this embodiment, for removing this problem, two high-polymer piezoelectric films are provided, thereby equivalently reducing the electric impedance. Here, since the electrode 1136 and the surface of the high-polymer piezoelectric film 1112 which contacts with the electrode 1136 becomes equal in potential to each other, the polarization directions of the two high-polymer piezoelectric films 1112 and 1135 are arranged to be opposite to each other as indicated by the arrows 11137 and 11138. Thus, irrespective of opposite drive voltages being applied to the high-polymer piezoelectric films 1112 and 1135, the vibrating operations can be effected in the same direction.

Figure 76:
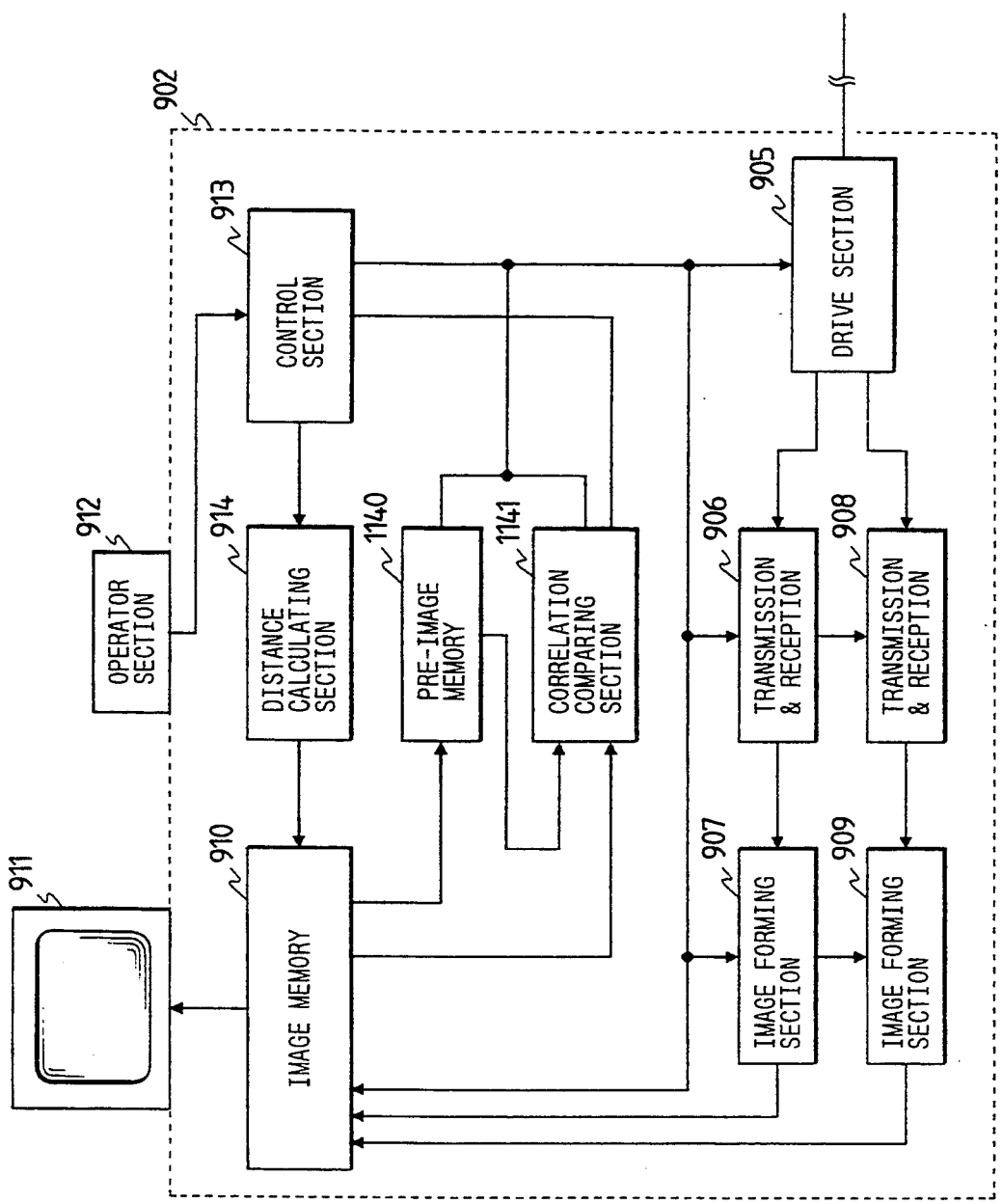
FIG. 76 is a block diagram showing an arrangement of an main body of an ultrasonic diagnostic apparatus according to a thirty eighth embodiment of this invention.

A thirty eighth embodiment of this invention will be described hereinbelow. FIG. 76 is a block diagram showing an arrangement of an main body 902. In FIG. 76, numeral 905 represents a drive section comprising a motor for generating a driving force and an angle detector, 906 designates a peripheral direction transmission and reception section, 907 depicts a peripheral direction image forming section connected to the peripheral direction transmission and reception section 906, 908 depicts a forward direction transmission and reception section connected to the drive section 905, 909 denotes a forward direction image forming section connected to the forward direction transmission and reception section 908, 910 indicates an image memory section connected to the peripheral direction image forming section 907 and the forward direction image forming section 909, 911 is a monitor connected to the image memory section 910 for displaying ultrasonic image, 912 represents an operator section for inputting various control instructions, 913 designates a control section connected to the operator section 912, and 914 depicts a distance calculating section connected to the control section 913. Further, number 1140 is a pre-image memory section connected to the image memory section 910, and 1141 designates a correlation comparing section connected to the image memory section 910 and the pre-image memory section 1140. The output of the correlation comparing section 1141 is coupled to the control section 913. The ultrasonic probe 901 can be used as an ultrasonic probe in this emobodiment which is not illustrated.

In operation, all or a portion of the peripheral direction ultrasonic image inputted to the image memory section 910 is transferred to the pre-image memory section 1140 and the correlation comparing section 1141 one time per n revolutions. The character n depends on the scanning rotating speed in the peripheral direction. For example, in the case of a rotational speed of 30 rps, it is preferable that n is set to 1 to 30 (1/30 second to 1 second). The pre-image memory section 1140 transfers the stored ultrasonic image to the correlation comparing section 1141 in synchronism with the transferring timing of the image from the image memory section 910. That is, to the correlation comparing section 1141, there are inputted the ultrasonic image transferred from the image memory section 910 and the ultrasonic image of n frames before the transfer of the ultrasonic image from the image memory section 910 which is transferred from the pre-image memory section 140.

The correlation comparing section 1141 performs the correlation calculation on the basis of these two ultrasonic images to compare the correlation calculation result with a threshold value set in advance. the comparison result is inputted to the control section. In the case that the calculation result shows that the two ultrasonic images are not coincident with each other, the control section 913 disregards this instruction until the correlation result shows that the two ultrasonic images become coincident with each other even if the image standstill instruction (freege instruction) is transferred from the operator section 912. Here, the image standstill function is for setting the obtained image to a still picture to obtain a quantitative value for diagnosis on the still picture in the distance calculating section 914.

According to this embodiment, the correlation relation between the two ultrasonic images which are different in time from each other is obtained, and hence it is possible to limit the image standstill function, for example, in the case that the rotating force due to the drive section 905 cannot stably be transferred to the tip portion of the ultrasonic probe, thus reducing the error diagnosis.

Figure 77:
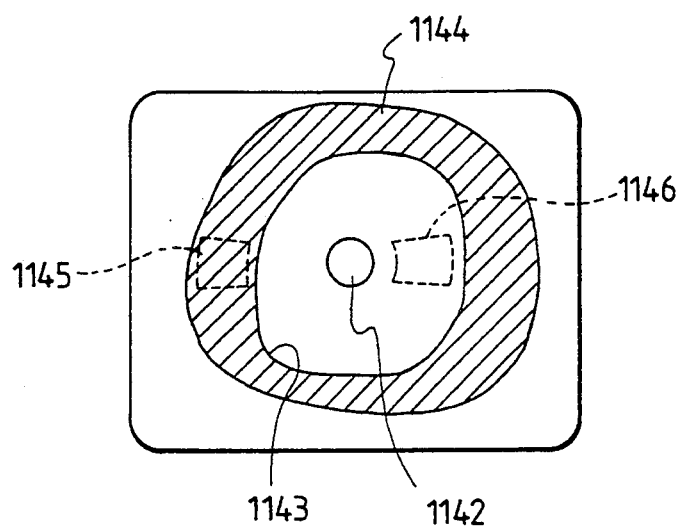
FIG. 77 shows a peripheral ultrasonic image.

FIG. 77 shows a peripheral ultrasonic image. In FIG. 77, numeral 1142 represents the center of the rotation, 1143 designates a wall of a blood vessel, 1144 depicts a speckle pattern which is the inside structure of the blood vessel, and 1145 and 1146 indicate areas. As the image area to be compared in the correlation comparing section 1141, there is used the entire peripheral direction ultrasonic image or the limited area, for example, the area 1145. The use of the limited area can reduce the calculation amount. The speckle pattern 1144 within the blood vessel is preferable to be used as the calculation area. Thus, for example, the correlation comparing section 1141 is in advance arranged so that the area 1145 is the comparing area.

Figure 78:
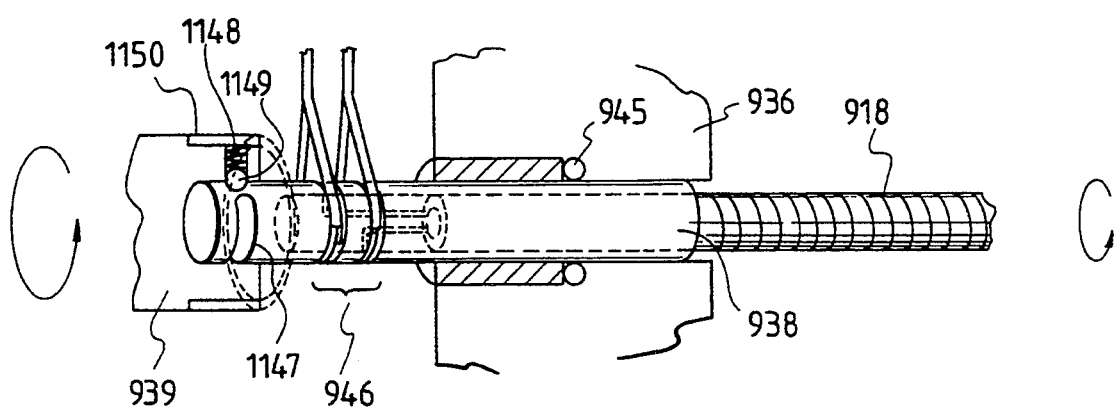
FIG. 78 is a perspective view showing an arrangement of the rear portion of an ultrasonic probe to be used in an ultrasonic diagnostic apparatus according to a thirty ninth embodiment of this invention.

A thirty ninth embodiment of this invention will be described hereinbelow. FIG. 78 is a perspective view showing an arrangement of the rear portion of an ultrasonic probe to be used in an ultrasonic diagnostic apparatus according to the thirty ninth embodiment of this invention. In FIG. 78, numeral 918 represents a torque transmission shaft, 938 designate a probe side connector, 945 depicts an oil sealing member, 946 denotes a signal contact portion, 939 indicates a main body side connector, 1147 is a groove formed in the tip portion of the probe side connector 938, 1148 represents a spring, 1149 designates a ball, 1150 denotes a spring pressing member.

Figure 79:
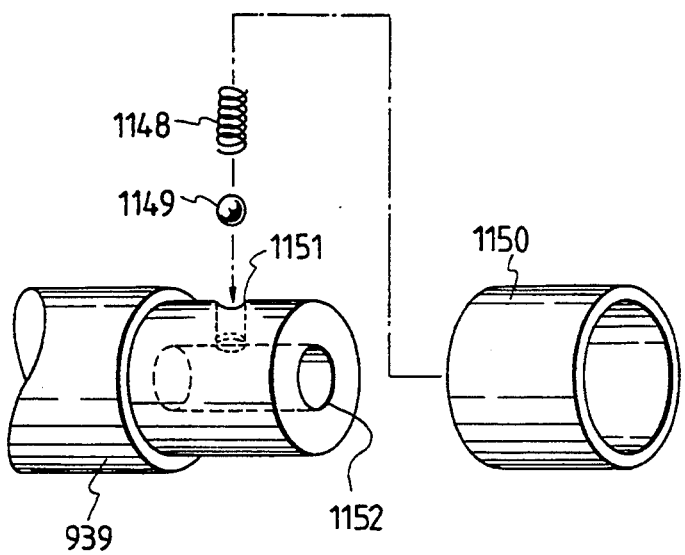
FIG. 79 shows an arrangement of a main body side connector to be used in the FIG. 78 ultrasonic probe.
Figure 80:
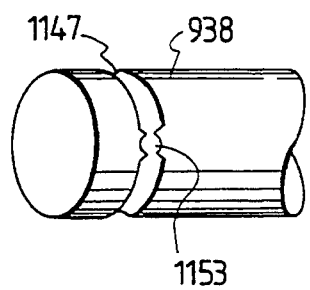
FIG. 80 shows an arrangement of a tip portion of a probe side connector to be used in the FIG. 78 ultrasonic probe

FIG. 79 shows an arrangement of the main body side connector 939. In FIG. 79, numeral 1151 represents a hole formed in the main body side connector 939, and 1152 designates a hollow portion of the main body side connector 939. The probe side connector 938 is inserted into the hollow portion of the main body side connector 939. The ball 1149 and the spring 1148 are inserted into the hole 1151 and pressed by the spring pressing member 1150. Further, FIG. 80 shows an arrangement of a tip portion of the probe side connector 938. The groove 1147 formed in the circumference of the probe side connector 938 is arranged to have a concave portion 1153 for the ball 1149.

The connection between the rear end portion side of the ultrasonic probe and the main body side is performed through a probe side fitting portion 936 and a main body side fitting portion 937. The connection of the torque transmission shaft 918 is effected such that the probe side connector 938 is inserted into the hollow portion 1152 of the main body side connector 939 in the state that the ball 1149 is coincident in position with the concave portion 1153. The rotating force of the drive section 905 rotates the main body side connector 939 and further rotates the probe side connector 938 and the torque transmission shaft 918 by the engagement between the ball 1149 and the concave portion 1153. In the case that a stress above the stress corresponding to the pressing force of the spring 1148 is required for the rotation of the torque transmission shaft 918, the ball 1149 is disconnected from the concave portion 1153 and rotated along the groove 1147. Accordingly, the rotation of the main body side is not transferred to the torque transmission shaft 918. This arrangement can prevent a trouble which occurs by any causes.

Figure 81:
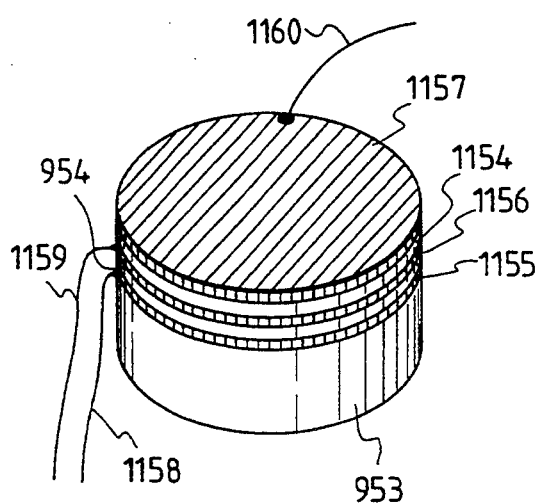
FIG. 81 is a perspective view showing an arrangement of an ultrasonic transducer of an ultrasonic probe to be used in an ultrasonic diagnostic apparatus according to the fortieth embodiment of this invention.
Figure 82:
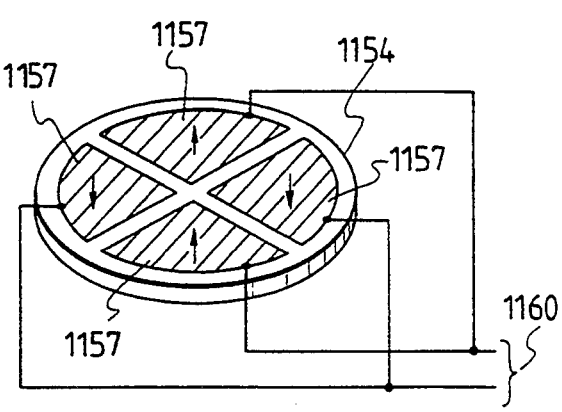
FIG. 82 shows an arrangement of a high-polymer piezoelectric film.

Still further, a fortieth embodiment of this invention will be described hereinbelow. FIG. 81 is a perspective view showing an arrangement of an ultrasonic transducer of an ultrasonic probe to be used in an ultrasonic diagnostic apparatus according to the fortieth embodiment of this invention. In FIG. 81, numeral 953 represents a backing load member, 1155 designates an electrode, 954 depicts a piezoelectric device, 1156 denotes an electrode, 1154 is a high-polymer piezoelectric film, 1157 is an electrode, 1158 represents a signal line connected to the electrode 1156, and 1160 designates a signal line connected to the electrode 1157. As illustrated in FIG. 82, the polarization process of the high-polymer piezoelectric film 1154 is effected symmetrically with respect to the central axis in opposite directions indicated by arrows, and the electrode 1157 is divided in correspondence with the polarization. At the time of the ultrasonic wave transmission and reception operation, a drive electric signal is supplied through the signal lines 1158 and 1159 to the piezoelectric device 954. The piezoelectric device 954 is constructed with a piezoelectric ceramic or a piezoelectric member having an excellent transmission characteristic. The high-polymer piezoelectric film 1154 on the piezoelectric device 954 surface acts as an acoustic matching layer to effectively transmit the ultrasonic wave from the piezoelectric device 954 into the propagation medium. At the time of the ultrasonic wave reception, the electric signal corresponding to the stress variation of the high-polymer piezoelectric film 1154 is derived through the signal lines 1160 and 1159. In addition, as illustrated in FIG. 82, the signals corresponding to the polarization directions of the high-polymer piezoelectric film 1154 are respectively derived. The respective output signals obtained in correspondence with opposite polarization directions have characteristics reverse to each other. If the two reception signals are obtained in accordance with the so-called differential amplification reception technique, it is possible to cancel the electric noises to compensate for the sensitivity deterioration due to the small area.

It should be understood that the foregoing relates to only preferred embodiments of the present invention, and that it is intended to cover all changes and modifications of the embodiments of the invention herein used for the purposes of the disclosure, which do not constitute departures from the spirit and scope of the invention.

What is claimed is:

1. An ultrasonic diagnostic apparatus comprising:
   a catheter having a flexible hollow structure and having a plurality of microlumens;
   a shaft having a hollow structure and fixed to a tip portion of said catheter;
   a bearing having a hollow structure and made of a material having a small frictional coefficient;
   a rotating shaft inserted into the hollow portions of said shaft and said bearing;
   a rotator which is fixed to a tip portion of said rotating shaft and in which a peripheral direction ultrasonic transducer and an ultrasonic wave reflecting mirror are disposed in opposed relation to each other, said rotator having a tubing structure and having an opening for emitting, in a direction substantially perpendicular to a longitudinal axis of the apparatus, an ultrasonic wave generated by said peripheral direction ultrasonic transducer and reflected by said reflecting mirror;
   an eccentric shaft fixed to a tip portion side of said rotator;
   a transducer holder rotatably supported by a pivot shaft and having at its rear end portion a groove engaged with said eccentric shaft so as to be sectorally movable about said pivot shaft;
   a forward direction ultrasonic transducer provided within said transducer holder for emitting an ultrasonic wave in a forward longitudinal direction of the apparatus;
   a cap fixed to said bearing, said pivot shaft being fixed to said cap;
   a torque transmission shaft fixed to a rear end portion of said rotating shaft and having a flexible multi-layered structure for transferring a rotating force;
   a first signal line passing through said lumen of said catheter and electrically connected to said forward direction ultrasonic transducer;
   a second signal line passing through the inside of said torque transmission shaft and electrically connected to said peripheral direction ultrasonic transducer; and
   a probe side connector fixed to a rear end portion of said torque transmission shaft;
   a main body side connector engageable with said probe side connector;
   a signal contact portion electrically connected to said second signal line disposed within said torque transmission shaft;
   a second rotating shaft connected to said main body side connector;
   a motor for rotating said second rotating shaft;
   a position detector for detecting a rotating state of said motor; and
   an image forming section for forming ultrasonic images, corresponding to ultrasonic wave generated from said ultrasonic transducers and returned to said ultrasonic transducers, on the basis of an output signal of said position detector.

2. An ultrasonic diagnostic apparatus as claimed in claim 1, wherein a rotatable, spherical, bearing made of a fluorine resin is rotatably provided on a portion of said eccentric shaft which is engaged with said groove of said transducer holder.

3. An ultrasonic diagnostic apparatus as claimed in claim 1, wherein said transducer holder has a contact portion having a spherical configuration, further comprising spring biasing means for biasing said contact portion so that said contact portion is brought into contact with said eccentric shaft.

4. An ultrasonic diagnostic apparatus as claimed in claim 1, further comprising a ferroelectric polymer film interposed between electrodes, said polymer film polarization-processed to show a piezoelectric characteristic, said piezoelectric polymer film being provided within said cap and positioned to come into contact with said transducer holder so as to generate a signal in response to the contact with said transducer holder, and wherein said position detector comprises a position signal generating section for generating a position signal indicative of said transducer holder on the basis of the signal generated by said piezoelectric polymer film.

5. An ultrasonic diagnostic apparatus as claimed in claim 4, further comprising a transmission and reception section coupled to said electrodes of said piezoelectric polymer film, a timing signal generating section for outputting a timing signal to said transmission and reception section for outputting a timing signal to said transmission and reception section so that said transmission and reception section outputs a transmission signal to said piezoelectric polymer film and inputs an output signal from said piezoelectric polymer film, a pulse generating section for generating pulses on the basis of an output signal of said transmission and reception section, a counter section for counting the pulses from said pulse generating section, and a comparing section for comparing the count value of said counter section with a reference value.

6. An ultrasonic diagnostic apparatus as claimed in claim 1, wherein the number of the layers of a tip portion of said torque transmission shaft is smaller than the number of the layers of a rear end portion of said torque transmission shaft.

7. An ultrasonic diagnostic apparatus as claimed in claim 1, wherein an outer diameter of a tip portion of said torque transmission shaft is smaller than an outer diameter of a rear end portion of said torque transmission shaft.

8. An ultrasonic diagnostic apparatus as claimed in claim 1, wherein the outermost layer of said torque transmission shaft is constructed with an element wire having a rectangular cross section, said element wire having projecting portions or notch portions at a predetermined interval so that said projecting portions or said notch portions are disposed between turns when being coiled.

9. An ultrasonic diagnostic apparatus as claimed in claim 1, further comprising an intermediate bearing provided within said catheter, said torque transmission shaft being inserted into said intermediate bearing so as to be rotatably supported by said intermediate bearing.

10. An ultrasonic diagnostic apparatus as claimed in claim 1, wherein said main body side connector has on its side surface a hole into which a ball and a spring are inserted, and said probe side connector has a groove having a ball-engaged portion which is engaged with said ball, a rotating force of said main body side connector is transferred through said ball and said spring to said probe side connector.

11. An ultrasonic diagnostic apparatus as claimed in claim 1, wherein at least one of said ultrasonic transducers comprises a first electrode, a high-polymer piezoelectric film, a second electrode, a piezoelectric film, a third electrode and a backing load member which are successively piled up, said high-polymer piezoelectric film being divided symmetrically with respect to a rotating axis of said ultrasonic transducer into portions, and polarization directions of a first group of the divided portions are arranged to be reverse to polarization directions of a second group of the divided portions.

12. An ultrasonic probe comprising:
a catheter having a flexible hollow structure and inserted into an object;
an ultrasonic transducer provided in a tip portion of said catheter for transmission and reception of an ultrasonic wave;
rotationally scanning means for two-dimensionally scanning the ultrasonic wave from said ultrasonic transducer;
a torque transmission shaft inserted into said catheter and at its one end portion connected to said rotationally scanning portion, said torque transmission shaft being constructed with an element wire so as to have a coil spring-like structure,
said element wire being transversely curved and having a transversely convex surface,
said element wire mounted around said torque transmission shaft with said transversely convex surface radially outwardly positioned relative to said torque transmission shaft, so that an external surface of said torque transmission shaft becomes flat; and
a drive section connected to the other end portion of said torque transmission shaft for transferring a rotating force through said torque transmission shaft to said rotationally scanning portion.

13. An ultrasonic diagnostic apparatus as claimed in claim 12, wherein an inner wall of said catheter comprises a plurality of grooves formed therein so as to reduce contact areas between the external surface of the torque transmission shaft and an inner surface of the catheter so as to ensure smooth rotation of the torque transmission shaft in the catheter.

14. An ultrasonic diagnostic apparatus as claimed in claim 13, wherein said grooves are oriented in a longitudinal direction of said catheter.

15. An ultrasonic diagnostic apparatus as claimed in claim 13, wherein said grooves have a spiral formation along a longitudinal direction of said catheter, said spiral formation being opposite along said longitudinal direction to a direction of rotation of the torque transmission shaft in said catheter.

16. An ultrasonic diagnostic apparatus as claimed in claim 13, wherein said grooves have a spiral formation along a longitudinal direction of said catheter, said spiral formation corresponding along said longitudinal direction to a direction of rotation of the torque transmission shaft in said catheter.

17. An ultrasonic diagnostic apparatus as claimed in claim 12, wherein said element wire further comprises a transversely concave surface opposing said convex surface,
said element wire mounted around said torque transmission shaft with said transversely convex surface radially outwardly positioned relative to said transversely concave surface.

18. An ultrasonic probe comprising:
a catheter having a flexible hollow structure and inserted into an object;
an ultrasonic transducer provided in a tip portion of said catheter for transmission and reception of an ultrasonic wave;
rotationally scanning means for two-dimensionally scanning the ultrasonic wave from said ultrasonic transducer;
a torque transmission shaft inserted into said catheter and at its one end portion connected to said rotationally scanning portion, said torque transmission shaft being constructed with an element wire so as to have a coil spring-like structure,
said element wire being substantially flat with a substantially rectangular cross section, one flat surface at one elongated side of the rectangular cross section having a pair of rounded edges for connecting by shorter sides of the rectangular cross section to another flat surface at the other elongated side of the rectangular cross section, said element wire mounted around said torque transmission shaft with said one flat surface radially outwardly positioned relative to said another flat surface, so that sharply protruding portions are eliminated from an external surface of said torque transmission shaft; and a drive section connected to the other end portion of said torque transmission shaft for transferring a rotating force through said torque transmission shaft to said rotationally scanning portion.

* * * * *